United States Patent
Nagashima

(10) Patent No.: US 12,064,296 B2
(45) Date of Patent: Aug. 20, 2024

(54) MEMORY DEVICE

(71) Applicant: KIOXIA CORPORATION, Tokyo (JP)

(72) Inventor: Satoshi Nagashima, Yokkaichi Mie (JP)

(73) Assignee: Kioxia Corporation, Tokyo (JP)

( * ) Notice: Subject to any disclaimer, the term of this patent is extended or adjusted under 35 U.S.C. 154(b) by 612 days.

(21) Appl. No.: 17/324,413

(22) Filed: May 19, 2021

(65) Prior Publication Data

US 2021/0280598 A1 Sep. 9, 2021

Related U.S. Application Data

(63) Continuation of application No. PCT/JP2019/035206, filed on Sep. 6, 2019.

(51) Int. Cl.
*H10B 41/10* (2023.01)
*A61B 90/00* (2016.01)
(Continued)

(52) U.S. Cl.
CPC ............ *A61B 90/361* (2016.02); *A61B 90/25* (2016.02); *G03B 17/561* (2013.01); *H04N 23/54* (2023.01);
(Continued)

(58) Field of Classification Search
CPC ............... H01L 27/115; H01L 27/1156; H01L 27/1157; H01L 27/11519; H01L 27/11524;
(Continued)

(56) References Cited

U.S. PATENT DOCUMENTS 9,147,468 B1 9/2015 Lue
9,666,594 B2 5/2017 Mizuno
(Continued)

FOREIGN PATENT DOCUMENTS

JP 2013-016781 A 1/2013
JP 2015-228484 A 12/2015
(Continued)

OTHER PUBLICATIONS

International Search Report issued in corresponding application No. PCT/JP2019/035206 dated Nov. 12, 2019.

*Primary Examiner* — Chuong A Luu
(74) *Attorney, Agent, or Firm* — Foley & Lardner LLP

(57) ABSTRACT

A memory device includes a first and second conductor respectively included in a first and second layer stack stacked in a first direction and separated from each other; a first and second portion of a semiconductor extending in the first direction between the first and the second layer stack, and separated from each other in same layer; a first film between the first conductor and the first portion; a second film between the second conductor and the second portion; a first insulator between the first conductor and the first film; a second insulator between the second conductor and the second film; a third insulator between the first insulator and the first film; and a fourth insulator between the second insulator and the second film. The third and fourth insulator have a higher dielectric constant than the first and second insulator.

14 Claims, 37 Drawing Sheets

(51) Int. Cl.
| | |
|---|---|
| *A61B 90/25* | (2016.01) |
| *G03B 17/56* | (2021.01) |
| *H04N 23/54* | (2023.01) |
| *H04N 23/695* | (2023.01) |
| *H10B 41/20* | (2023.01) |
| *H10B 41/35* | (2023.01) |
| *H10B 43/10* | (2023.01) |
| *H10B 43/20* | (2023.01) |
| *H10B 43/35* | (2023.01) |
| *A61B 90/50* | (2016.01) |

(52) U.S. Cl.
CPC ........... *H04N 23/695* (2023.01); *H10B 41/10* (2023.02); *H10B 41/20* (2023.02); *H10B 41/35* (2023.02); *H10B 43/10* (2023.02); *H10B 43/20* (2023.02); *H10B 43/35* (2023.02); *A61B 2090/506* (2016.02)

(58) Field of Classification Search
CPC ......... H01L 27/11521; H01L 27/11551; H01L 27/11565; H01L 27/11578; H01L 27/11556; H01L 27/11573; H01L 27/11541; H01L 27/11582; H01L 27/11548; H01L 27/11575; H10B 41/10; H10B 41/20; H10B 41/35; H10B 43/10; H10B 43/20; H10B 43/35

USPC .................................................. 257/314, 326
See application file for complete search history.

(56) References Cited

U.S. PATENT DOCUMENTS

| | | |
|---|---|---|
| 10,020,315 B1 | 7/2018 | Kato |
| 10,340,013 B2 | 7/2019 | Futatsuyama |
| 2011/0049615 A1* | 3/2011 | Saito .................... H01L 29/7843 |
| | | 257/329 |
| 2012/0327714 A1 | 12/2012 | Lue |
| 2014/0008714 A1 | 1/2014 | Makala et al. |
| 2015/0249010 A1* | 9/2015 | Kubota .................. H10B 43/40 |
| | | 438/763 |
| 2016/0260733 A1 | 9/2016 | Lue |
| 2017/0263613 A1* | 9/2017 | Murakoshi ............. H10B 43/20 |
| 2017/0263615 A1 | 9/2017 | Sakaike |
| 2017/0263780 A1 | 9/2017 | Sawa |
| 2018/0269218 A1 | 9/2018 | Kato |

FOREIGN PATENT DOCUMENTS

| | | |
|---|---|---|
| JP | 2017-163044 A | 9/2017 |
| JP | 2017-168163 A | 9/2017 |
| JP | 2018-160634 A | 10/2018 |

* cited by examiner

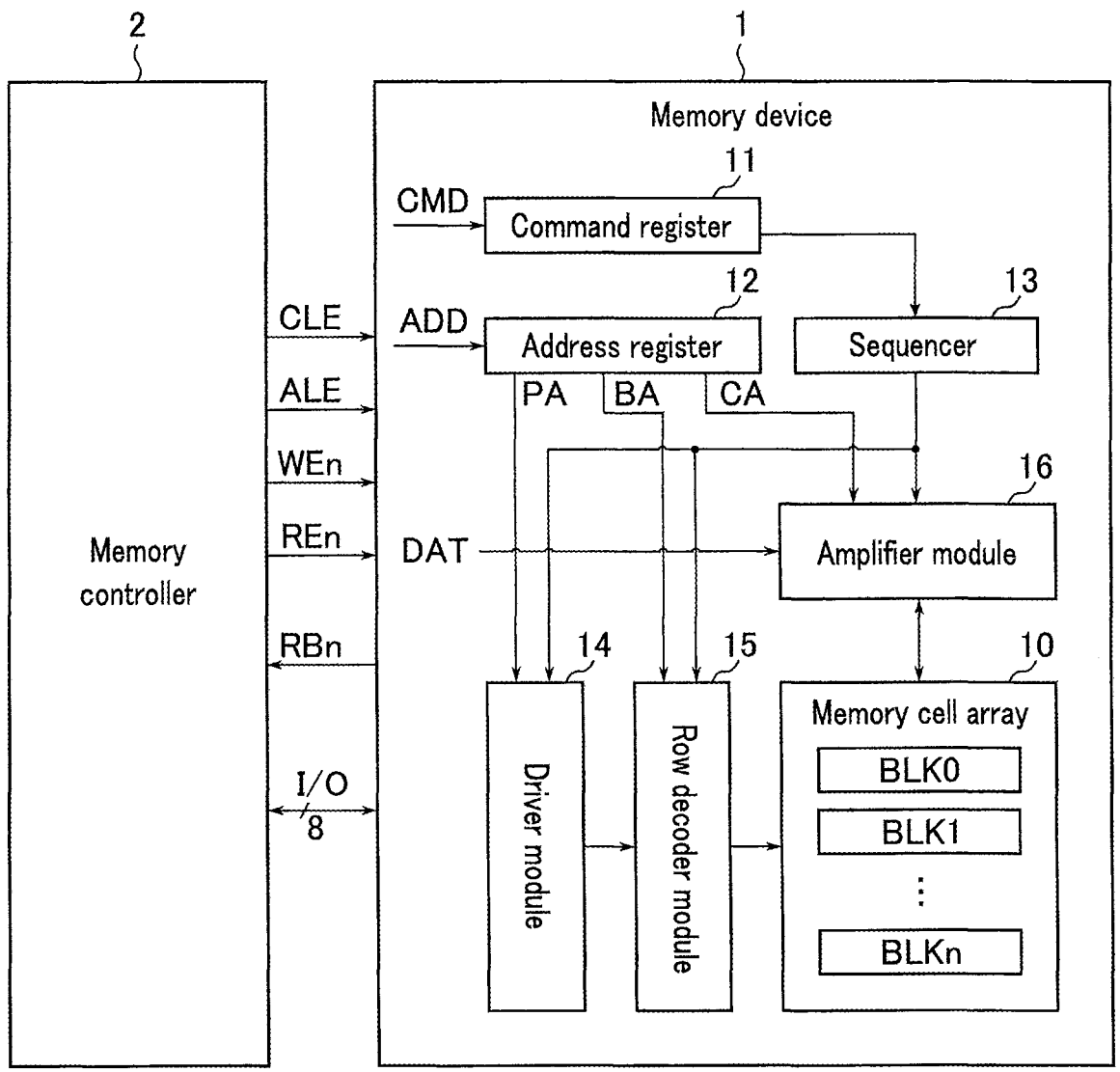
F I G. 1

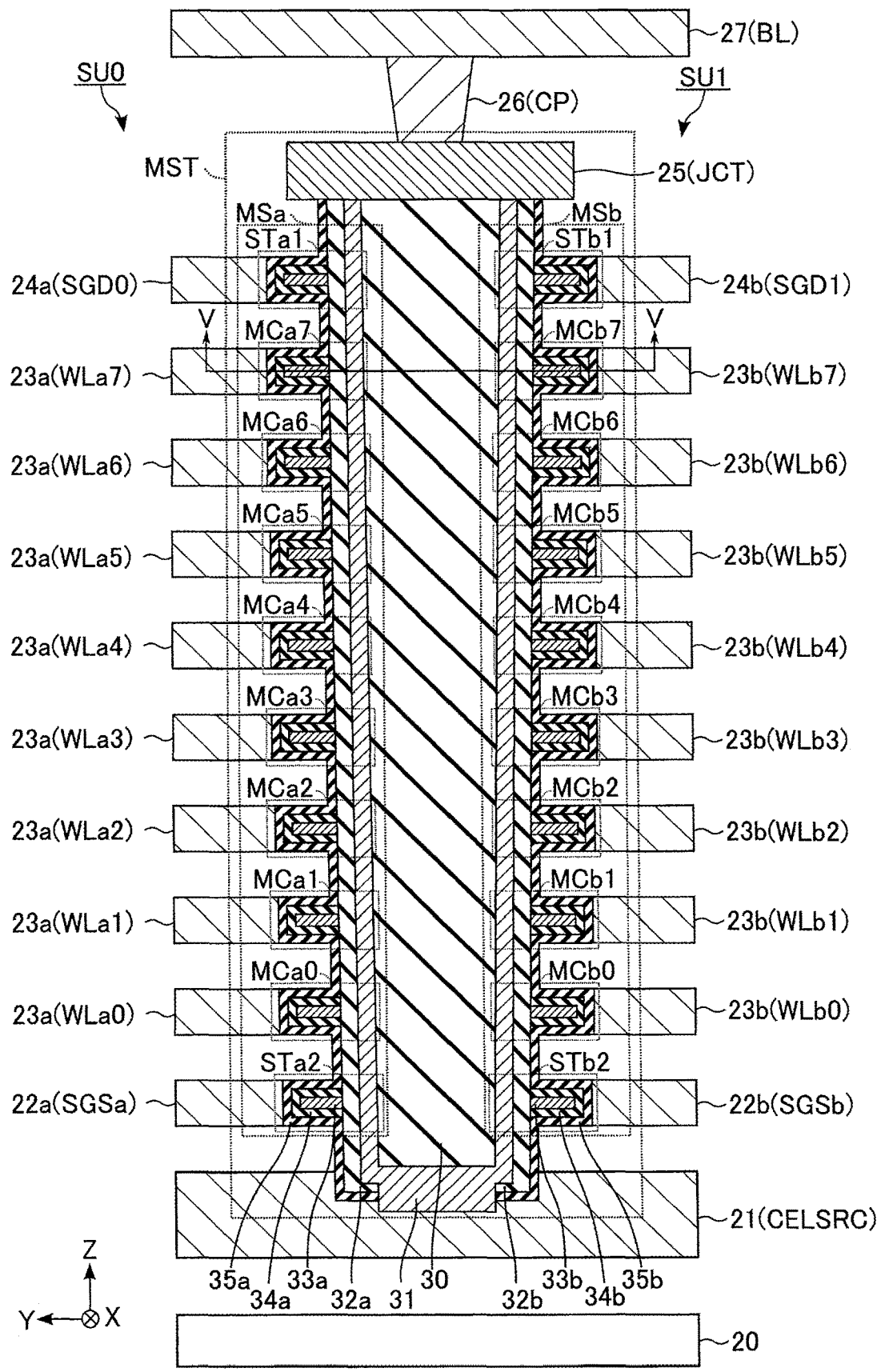
F I G. 4

MEMORY DEVICE

CROSS-REFERENCE TO RELATED APPLICATIONS

This application is a Continuation Application of PCT Application No. PCT/JP2019/035206, filed Sep. 6, 2019, the entire contents of which are incorporated herein by reference.

FIELD

Embodiments described herein relate generally to a memory device.

BACKGROUND

A memory device capable of storing data non-volatilely has been known. With regard to this type of memory device, a three-dimensional memory structure with high integration and large capacity has been considered.

BRIEF DESCRIPTION OF THE DRAWINGS

FIG. 1 is a block diagram showing a configuration of a memory system including a memory device according to a first embodiment.

FIG. 4 is a vertical cross-sectional view of the memory cell array taken along line IV-IV in FIG. 3.

DETAILED DESCRIPTION

Figure 2:
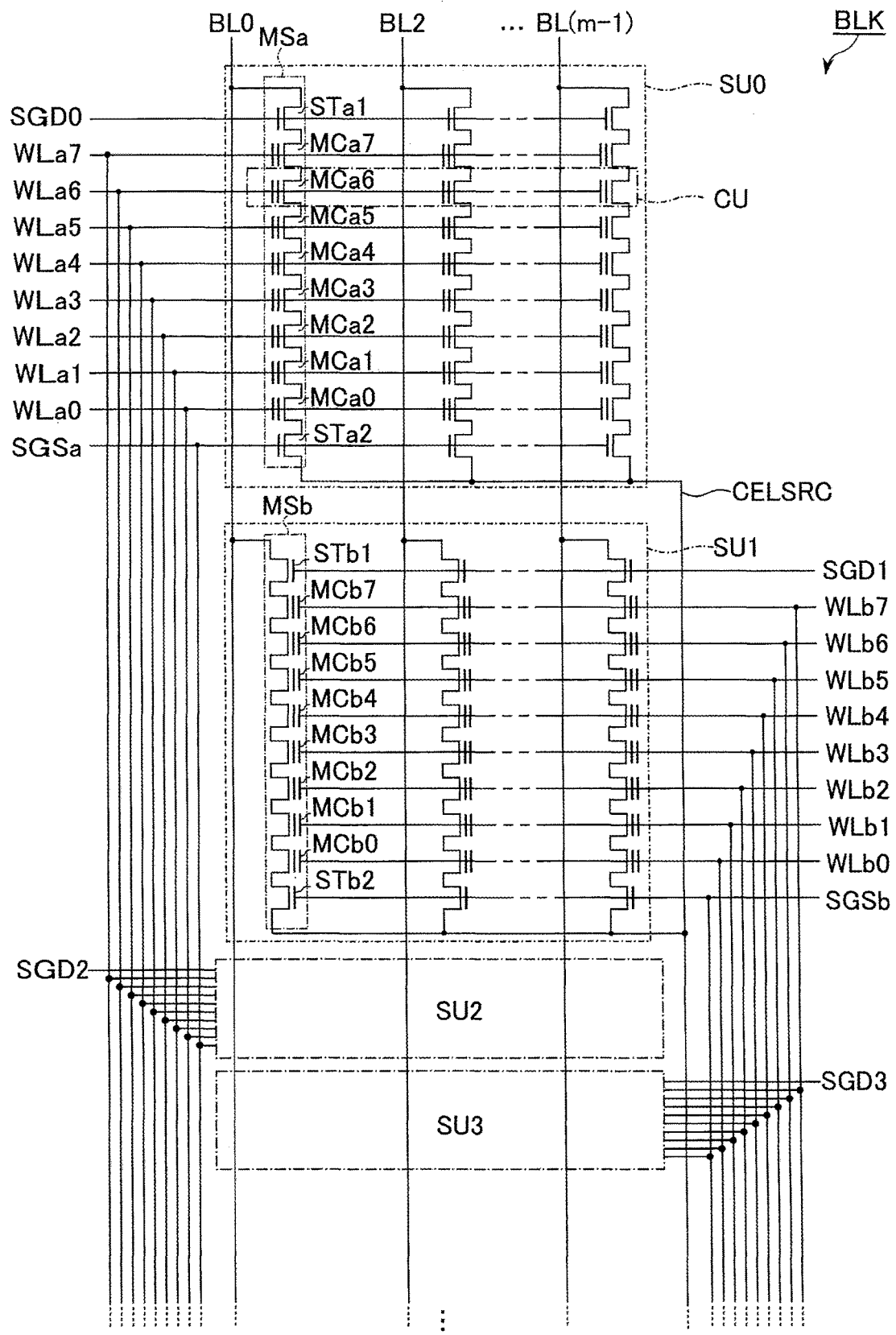
FIG. 2 is a circuit configuration diagram showing a memory cell array in the memory device according to the first embodiment.

In general, according to one embodiment, a memory device includes a first conductor, a second conductor, a first semiconductor, a first charge storage film, a second charge storage film, a first insulator, a second insulator, a third insulator, and a fourth insulator. The first conductor is included in a first layer stack that is stacked in a first direction. The second conductor is included in a second layer stack that is stacked in the first direction and included in a layer that includes the first conductor. The second layer stack is separated from the first layer stack. The first semiconductor is between the first layer stack and the second layer stack and includes a first portion, a second portion, and a third portion. The first portion and a second portion each extends in the first direction, and are separated from each other in same layer. The third portion electrically couples the first portion and the second portion below the first conductor and the second conductor. The first charge storage film is between the first conductor and the first portion of the first semiconductor. The second charge storage film is between the second conductor and the second portion of the first semiconductor. The first insulator is between the first conductor and the first charge storage film. The second insulator is between the second conductor and the second charge storage film. The third insulator is between the first insulator and the first charge storage film. The fourth insulator is between the second insulator and the second charge storage film. The third insulator and the fourth insulator have a dielectric constant higher than that of the first insulator and the second insulator.

Hereinafter, embodiments will be described with reference to the accompanying drawings. Each embodiment is an example of a device or method that embodies a technical idea of the invention. It should be noted that the drawings are schematic or conceptual, and that the dimensions and scales of the drawings are not necessarily the same as those of the actual products. The technical idea of the present invention is not specified by the shape, structure, arrangement, etc. of structural elements.

The description will use the same reference symbols for the structural elements having the same or substantially the same functions and configurations. The numbers after the letters constituting the reference symbols are used to discriminate elements denoted by reference symbols including the same letters and that have similar configurations. If elements represented by reference symbols that have the same letters need not be distinguished, those elements are assigned reference symbols that have only the same letters.

In the following description, a cross section parallel to a stack surface of a structure stacked on a substrate may be referred to as "a transverse cross section", and a cross section that intersects the stack surface may be referred to as "a vertical cross section".

The term "diameter" refers to a diameter of a structural element in a transverse cross section, and the term "thickness" refers to a thickness of a structural element in a transverse or vertical cross section.

1. First Embodiment

A memory device according to the first embodiment will be described.

1.1 Configuration

First, a configuration of the memory device according to the first embodiment will be described.

1.1.1 Memory Device

FIG. 1 is a block diagram for explaining a configuration of a memory system including the memory device according to the first embodiment. The memory device 1 is a NAND flash memory, which can store data in a non-voltile manner, and is controlled by an external memory controller 2. Communications between the memory device 1 and the memory controller 2 conform to a NAND interface standard, for example.

As shown in FIG. 1, the memory device 1 includes, for example, a memory cell array 10, a command register 11, an address register 12, a sequencer 13, a driver module 14, a row decoder module 15, and a sense amplifier module 16.

The memory cell array 10 includes a plurality of blocks BLK0 to BLKn (where n is an integer greater than or equal to 1). The block BLK is a set including a plurality of memory cells each can store data non-volatilely, and is used as, for example, a data erase unit. A plurality of bit lines and a plurality of word lines are provided in the memory cell array 10. Each memory cell is associated with, for example, a single bit line and a single word line. A detailed configuration of the memory cell array 10 will be described later.

The command register 11 stores a command CMD received by the memory device 1 from the memory controller 2. The command CMD includes an instruction to instruct, for example, the sequencer 13 to perform a read operation, a write operation, an erase operation, or the like.

The address register 12 stores address information ADD received by the memory device 1 from the memory controller 2. The address information ADD includes, for example, a block address BA, a page address PA, and a column address CA. For example, the block address BA, the page address PA, and the column address CA are used to select a block BLK, a word line, and a bit line, respectively.

The sequencer 13 controls the operation of the entire memory device 1. For example, the sequencer 13 controls the driver module 14, the row decoder module 15, and the sense amplifier module 16, etc., based on the command CMD stored in the command register 11, to perform a read operation, a write operation, an erase operation, etc.

The driver module 14 generates voltages for use in a read operation, a write operation, an erase operation, etc. Then, the driver module 14 applies a generated voltage to a signal line corresponding to a selected word line based on, for example, a page address PA stored in the address register 12.

Based on the block address BA stored in the address register 12, the row decoder module 15 selects one corresponding block BLK in the memory cell array 10. The row decoder module 15 transfers, for example, the voltage applied to the signal line, corresponding to the selected word line, to the selected word line in the selected block BLK.

The sense amplifier module 16, in a write operation, applies a certain voltage to each bit line in accordance with write data DAT received from the memory controller 2. In a read operation, the sense amplifier module 16 determines data stored in a memory cell based on the voltage of the bit line, and transfers the determination result to the memory controller 2 as the data DAT.

The memory device 1 and the memory controller 2 described above may be combined to constitute a single memory system. Examples of such a memory system include a memory card such as an SD™ card, and a solid state drive (SSD).

1.1.2 Circuit Configuration of Memory Cell Array

Next, a configuration of the memory cell array 10 according to the first embodiment will be described, with reference to FIG. 2. FIG. 2 is an equivalent circuit diagram of a block BLK.

As shown in FIG. 2, the block BLK includes, for example, eight string units SU (SU0, SU1, SU2, SU3, . . . SU7). In FIG. 2, four string units (SU0 to SU3) of the eight string units SU0 to SU7 are shown as an example.

Each of the string units SU includes a plurality of memory strings MS. In the following, the memory string MS in the string units SUa (SU0, SU2, SU4 and SU6) will be referred to as the memory string MSa, and the memory string MS in the string units SUb (SU1, SU3, SU5, and SU7) will be referred to as the memory string MSb, when it is necessary to distinguish the memory strings from each other. As for the other configurations and interconnects, etc., those belonging to the string units SUa will be indicated by "a" added to the reference symbols, and those belonging to the string units SUb will be indicated by "b" added to the reference symbols, for the sake of distinction.

Each memory string MS includes, for example, eight memory cell transistors MC (MC0 to MC7) and select transistors ST1 and ST2. Each memory cell transistor MC is provided with a control gate and a charge storage film, and stores data non-volatilely. The eight memory cell transistors MC are coupled in series between the source of the select transistor ST1 and the drain of the select transistor ST2.

The gates of select transistors STa1 included in the string units SUa (SU0, SU2, SU4, and SU6) are coupled to select gate lines SGDa (SGD0, SGD2, SGD4, and SGD6), respectively. The gates of select transistors STb1 included in the string units SUb (SU1, SU3, SU5, and SU7) are coupled to select gate lines SGDb (SGD1, SGD3, SGD5, and SGD7), respectively. Voltages applied to the select gate lines SGD0 to SGD7 are independently controlled by the row decoder module 15.

In addition, the gates of the select transistors STa2 included in the string units SUa in the same block BLK are coupled in common to, for example, a select gate line SGSa, and the gates of the select transistors STb2 included in the string units SUb in the same block BLK are coupled in common to, for example, a select gate line SGSb. Voltages applied to the select gate lines SGSa and SGSb may be the same, or may each be independently controllable.

The control gates of the memory cell transistors MCa (MCa0 to MCa7) included in the string units SUa within the same block BLK are respectively coupled in common to word lines WLa (WLa0 to WLa7). On the other hand, the control gates of memory cell transistors MCb (MCb0 to MCb7) included in the string units SUb are respectively coupled in common to word lines WLb (WLb0 to WLb7). Voltages applied to the word lines WLa and WLb are independently controlled by the the row decoder module 15.

A block BLK is a unit of data erasure for example. In other words, data stored in the memory cell transistors MC included in the same block BLK is erased in a batch.

Moreover, the drains of the select transistors ST1 of the memory strings MS in the same column in the memory cell array 10 are coupled in common to a bit line BL (BL0 to BL (m−1), where m is a natural number). In other words, the bit line BL is coupled in common to a single memory string MSa in each of the string units SUa and a single memory string MSb in each of the string units SUb. Moreover, the sources of a plurality of select transistors ST2 are coupled in common to a source line CELSRC.

In other words, a string unit SU is a set including a plurality of memory strings MS respective coupled to different bit lines BL and coupled to the same select gate line SGD. In a string unit SU, a set of memory cell transistors MC coupled in common to the same word line WL may be also called "a cell unit CU". In addition, a block BLK is a set of a plurality of string units SUa sharing the same word lines WLa0 to WLa7 and a plurality of string units SUb sharing the same word lines WLb0 to WLb7. Moreover, the memory cell array 10 is a set including a plurality of blocks BLK sharing a plurality of bit lines BL.

In the memory cell array 10, the select gate line SGS, the word lines WL, and the select gate line SGD are sequentially stacked above a semiconductor substrate, thereby constituting a three-dimensional stack of the memory cell transistors MC and the select transistors ST1 and ST2.

1.1.3 Layout of Memory Cell Array

Next, a layout of the memory cell array according to the first embodiment will be described with reference to FIG. 3.

Figure 3:
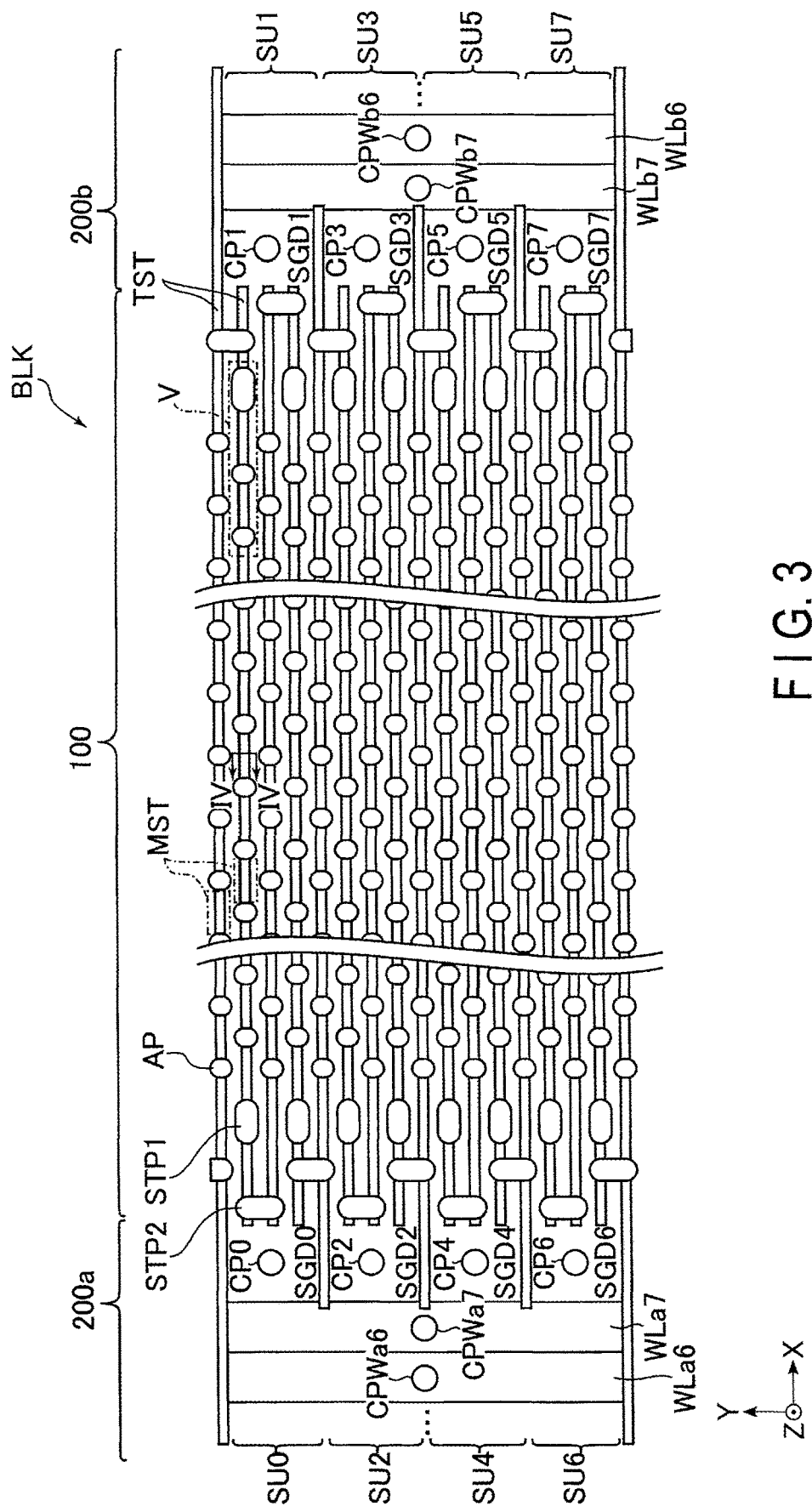
FIG. 3 is a planar layout of the memory cell array in the memory device according to the first embodiment, as viewed from above.

FIG. 3 is an example of a planer layout of a portion corresponding to one block of the memory cell array in the memory device according to the first embodiment. In FIG. 3, components such as inter-layer insulating films and wiring are omitted where not necessary, for improved visibility. In FIG. 3 and the subsequent drawings, two directions parallel to the surface of the semiconductor substrate and orthogonal to each other are defined as an X direction and a Y direction, and the direction orthogonal to a surface defined by the X and Y directions (XY plane) is defined as a Z direction (stacking direction).

The memory cell array 10 includes a cell area 100 and hookup areas 200 (200a and 200b), as shown in FIG. 3. The hookup areas 200a and 200b are located on both sides of the cell area 100 in the X direction so as to sandwich the cell area 100. In other words, the hookup area 200a is located at one end of the cell area 100 in the X direction, and the hookup area 200b is located at the other end of the cell area 100 in the X direction.

Over the cell area 100 and the hookup areas 200, the select gate lines SGSa and SGSb (not shown), the word lines WLa0 to WLa7 and WLb0 to WLb7 (partly not shown), and the select gate lines SGD0 to SGD7 are stacked in the Z direction. For example, the select gate lines SGSa and SGSb are provided on the same layer, the word lines WLai and WLbi ($0 \leq i \leq 7$) are provided on the same layer, and the select gate lines SGD0 to SGD7 are formed on the same layer. The word lines WLa0 and WLb0 are provided on a layer above the select gate lines SGSa and SGSb, the word lines WLaj and WLbj ($1 \leq j \leq 7$) are provided on a layer above the word lines WLa (j−1) and WLb (j−1), and the select gate lines SGD0 to SGD7 are provided on a layer above the word lines WLa7 and WLb7. In the following description, the select gate lines SGD and SGS and the word lines WL are collectively referred to as "stacked wiring".

First, the cell area 100 is described.

The cell area 100 includes a plurality of trench structures TST, a plurality of pillars AP for cell separation, a plurality of pillars STP1 for stacked wiring replacement, and a plurality of pillars STP2 for stacked wiring division, all of which pass through all the stacked wiring. For example, the pillars AP are located in a central portion of the cell area 100, the pillars STP1 are located nearer to both sides of the cell area 100 than the pillars AP, and the pillars STP2 are located nearer to both sides of the cell area 100 than the pillars STP1.

The trench structures TST extend in the X direction and are arranged alongside in the Y direction. Each of the trench structures TST is separated into a plurality of memory structures MST by the pillars AP arranged at regular intervals in the X direction. The pillars AP are arranged in a staggered manner on the trench structures TST. Accordingly, the memory structures MST separated by the pillars AP are also arranged in a staggered manner. In other words, the memory structures MST included in one of the two trench structures TST adjacent to each other in the Y direction are respectively located in positions half-pitch shifted from the memory structures MST included in the other of the two trench structures in X direction.

The pillars STP1 are provided at the end portions of every other trench structure TST of the trench structures TST arranged alongside in the Y direction, so as to divide the trench structure TST. As a result, every other trench structure TST of the trench structures TST arranged alongside in the Y direction is separated by the two pillars STP1 into three portions of a central portion including the memory structures MST, and two end portions including no memory structures MST. In the example shown in FIG. 3, two trench structures TST adjacent to the trench structure TST divided by the pillar STP1 are not provided with a pillar STP1; however, a pillar STP1 may also be provided in both end portions of the two trench structures TST.

Of the stacked wiring, a portion sandwiched between any one of the trench structures TST arranged alongside in the Y direction and one of the two trench structures TST adjacent to the one of the trench structures TST is separated by one pillar STP2 at one of the two end portions (for example, on the hookup area 200a side) of the cell area 100. Furthermore, of the stacked wiring, a portion sandwiched between the one of the trench structures TST and the other one of the two trench structures TST adjacent to the one of the trench structures TST is separated by one pillar STP2 at the other of the two end portions (for example, on the hookup area 200b side) of the cell area 100.

Due to the configuration described above, in the cell area 100, the stacked wiring is separated into a comb tooth shape portion extending from the hookup area 200a (the select gate line SGSa, the word lines WLa0 to WLa7, and the select gate lines SGDa) and a comb tooth shape portion extending from the hookup area 200b (the select gate line SGSb, the word lines WLb0 to WLb7, and the select gate lines SGDb). The comb tooth shape portions of the stacked wiring are in contact with the memory structures MST at both side surfaces.

Next, the hookup area 200 will be described.

In the hookup area 200, the stacked wiring is formed as a step shape. Specifically, the interconnects in lower layers of the stacked wiring extend longer in the X direction, and every interconnect in the stacked wiring has a terrace area that does not overlap any other wire of upper layers of the stacked wiring.

In the hookup area 200a, an interconnect formed in a layer corresponding to the select gate lines SGDa in the stacked wiring is separated into four select gate lines SGD0, SGD2, SGD4, and SGD6 by the trench structures TST. The select gate lines SGD0, SGD2, SGD4, and SGD6 respectively include contacts CP0, CP2, CP4, and CP6 on the corresponding terrace areas.

The word lines WLa0 to WLa7 (partly not shown) respectively include contacts CPWa0 to CPWa7 (partly not shown) on the corresponding terrace areas.

The select gate line SGSa also includes a contact (not shown) on the corresponding terrace area (not shown).

In the hookup area 200b, an interconnect formed in a layer corresponding to the select gate lines SGDb in the stacked wiring is separated into four select gate lines SGD1, SGD3, SGD5, and SGD7 by the trench structures TST. The select gate lines SGD1, SGD3, SGD5, and SGD7 respectively include contacts CP1, CP3, CP5, and CP7 on the corresponding terrace areas.

The word lines WLb0 to WLb7 (partly not shown) respectively include contacts CPWb0 to CPWb7 (partly not shown) on the corresponding terrace areas.

The select gate line SGSb also includes a contact (not shown) on the corresponding terrace area (not shown).

Due to the configuration described above, all interconnects in the stacked wiring can be hooked up above the memory cell array 10 from the hookup area 200.

FIG. 3 shows only one block BLK of the memory cell array 10, while the other blocks BLK are omitted. However, a plurality of blocks BLK0 to BLKn having a configuration similar to that shown in FIG. 3 are arranged in sequence, for example, in the Y direction.

1.1.4 Memory Structure

Hereinafter, an example of a configuration of the memory structure of the memory device according to the first embodiment is described. FIG. 4 is a cross-sectional view taken along line IV-IV in FIG. 3. In FIG. 4, components such as inter-layer insulating films are omitted where not necessary, for improved visibility.

First, a configuration of a cross section along a YZ plane of the memory structure MST will be described with reference to FIG. 4. FIG. 4 shows a configuration including a memory structure MST in the trench structures TST that belong to the string units SU0 and SU1, and a plurality of conductors that function as various interconnects coupled to the memory structure MST.

As shown in FIG. 4, a conductor 21 functioning as a source line CELSRC is provided above the semiconductor substrate 20. The conductor 21 is made of an electrically conductive material. For example, an n-type semiconductor doped with impurities or a metal material may be used. The conductor 21 may be a stacked structure of a semiconductor and a metal. A circuit, such as the row decoder module 15 and the sense amplifier module 16, may be provided between the semiconductor substrate 20 and the conductor 21.

A conductor 22a functioning as the select gate line SGSa and a conductor 22b functioning as the select gate line SGSb, which are provided in the same layer, are stacked above the conductor 21 along the Z direction with an insulator (not shown) interposed therebetween. Above the conductor 22a, eight layers of conductors 23a functioning as the word lines WLa0 to WLa7 are stacked along the Z direction, with an insulator (not shown) interposed between layers. Similarly, above the conductor 22b, eight layers of conductors 23b functioning as the word lines WLb0 to WLb7 are stacked along the Z direction, with an insulator (not shown) interposed between layers. Above each of the conductors 23a and 23b, a conductor 24a functioning as the select gate line SGD0 and a conductor 24b functioning as the select gate line SGD1 are respectively stacked along the Z direction, with an insulator (not shown) interposed therebetween.

The conductors 22a to 24a and 22b to 24b are made of an electrically conductive material. For example, an n-type semiconductor or a p-type semiconductor doped with impurities, or a metal material may be used. For example, as the conductors 22a to 24a and 22b to 24b, a structure in which tungsten (W) is covered with titanium nitride (TiN) is used. Titanium nitride functions as a barrier layer to prevent reaction between tungsten and silicon oxide ($SiO_2$) or as a layer to improve adhesion of tungsten, when tungsten is deposited by a chemical vapor deposition (CVD). Furthermore, the conductors 22a to 24a and 22b to 24b may be obtained by further covering the aforementioned electrically conductive material with aluminum oxide (AlO).

A conductor 27 is provided above the conductors 24a and 24b with an insulator (not shown) interposed therebetween. The conductor 27 extends in the Y direction, and a plurality of conductors 27 are arranged alongside each other in lines in the X direction, which are used as bit lines BL. The conductor 27 includes, for example, copper (Cu).

The memory structure MST extends in the Z direction between the conductors 22a to 24a and the conductors 22b to 24b, and its bottom surface reaches the conductor 21. The conductors 22a to 24a are separated from the conductors 22b to 24b by the trench structures TST including the memory structures MST and extending in the X direction.

The memory structure MST includes a core member 30, a semiconductor 31, tunnel insulating films 32a and 32b, a plurality of charge storage films 33a, a plurality of block insulating films 34a, a block insulating film 35a, a plurality of charge storage film 33b, a plurality of block insulating films 34b, a block insulating film 35b, and a semiconductor 25. Each of the charge storage films 33a and the block insulating films 34a is provided in each layer of the conductors 22a to 24a. Each of the charge storage films 33b and the block insulating films 34b is provided in each layer of the conductors 22b to 24b.

The core member 30 extends in the Z direction, its upper end is included a layer above the conductors 24a and 24b, and its bottom end is included in the layers below the conductors 22a and 22b. The core member 30 includes, for example, silicon oxide.

The semiconductor 31 covers the bottom surface of the core member 30, and two side surfaces thereof that face each other in the Y direction (namely, along the XZ plane). The upper end of the semiconductor 31 reaches a position equivalent to the upper end of the core member 30, and the bottom end of the semiconductor 31 is in contact with the conductor 21 below the lower bottom of the core member 30. The semiconductor 31 includes, for example, polysilicon.

The tunnel insulating film 32a covers one of the two side surfaces along the XZ plane of the semiconductor 31, and the tunnel insulating film 32b covers the other of the two side surfaces along the XZ plane of the semiconductor 31. The tunnel insulating films 32a and 32b have upper ends that reach a position equivalent to the upper ends of the core member 30 and the semiconductor 31, and include, for example, silicon oxide.

In each of the layers provided with the conductors 22a to 24a, the charge storage film 33a is provided on the side surface along the XZ plane of the tunnel insulating film 32a. In each of the layers provided with the conductors 22a to 24a, the block insulating film 34a covers the charge storage film 33a. The block insulating film 35a is provided as a continuous film covering the block insulating films 34a. Each of the conductors 22a to 24a is in contact with the block insulating film 34a in the corresponding layer.

In each of the layers provided with the conductors 22b to 24b, the charge storage film 33b is provided on the side surface along the XZ plane of the tunnel insulating film 32b. In each of the layers provided with the conductors 22b to 24b, the block insulating film 34b covers the charge storage film 33b. The block insulating film 35b is provided as a continuous film covering the block insulating films 34b. Each of the conductors 22b to 24b is in contact with the block insulating film 34b in the corresponding layer.

The charge storage films 33a and 33b include, for example, polysilicon or a metal including at least one selected from titanium (Ti), tungsten (W), and ruthenium (Ru). The block insulating films 34a and 34b are formed of a high dielectric constant (high-k) material having a dielectric constant higher than that of the block insulating films 35a and 35b, and include, for example, hafnium silicate (HfSiO) or zirconium silicate (ZrSiO). The block insulating films 35a and 35b include, for example, silicon oxide ($SiO_2$).

The semiconductor 25 includes, for example, polysilicon, and covers the top surface of the core member 30, the top surface of the semiconductor 31, and the top surfaces of the tunnel insulating films 32a and 32b. Thus, the semiconductor 31 can form two parallel current paths between the semiconductor 25 and the conductor 21, the current paths being located alongside each other in the Y direction with the core member 30 interposed therebetween. Thus, the semiconductor 25 functions as a joint portion JCT of the current paths.

A conductor 26 functioning as a pillar-shaped contact CP is provided on the top surface of the semiconductor 25. The top surface of the conductor 26 is in contact with and electrically coupled to the one corresponding conductor 27.

In the memory structure MST described above, the part where the memory structure MST intersects with the conductor 22a functions as the select transistor STa2, and the part where the memory structure MST intersects with the conductor 22b functions as the select transistor STb2. The part where the memory structure MST intersects with the conductor 23a functions as the memory cell transistor MCa, and the part where the memory structure MST intersects with the conductor 23b functions as the memory cell transistor MCb. The part where the memory structure MST intersects the conductor 24a functions as the select transistor STa1, and the part where the memory structure MST intersects with the conductor 24b functions as the select transistor STb1.

Thus, the semiconductor 31 is used as the channels and well regions of the select transistors STa1 and STb1, the memory cell transistors MCa and MCb, and the select transistors STa2 and STb2. The charge storage films 33a are used as the floating gates of the memory cell transistors MCa and the select transistors STa1 and STa2, and the charge storage films 33b are used as the floating gates of the memory cell transistors MCb and the select transistors STb1 and STb2. Thus, the memory structure MST functions as a set including, for example, two memory strings MSa and MSb.

The configuration of the memory structure MST described above is a mere example, and the memory structure MST may have other configurations. For example, the number of the conductors 23 is determined based on the number of the word lines WL that can be designed to be of any number. To the select gate lines SGS and SGD, the discretionally determined number of conductors 22 and 24 may be respectively allocated. If a plurality of layers of the conductors 22 are allocated to the select gate line SGS, different conductors may be used for the respective layers of the conductors 22. A discretionally determined number of conductors functioning as a dummy word line (not shown) may be provided between the lowermost word line WL and the select gate line SGS, and between the uppermost word line WL and the select gate line SGD. The semiconductor 25 and the conductor 27 may be electrically coupled via two or more contacts, or via another interconnect.

1.1.5 Trench Structure

Next, a configuration of a cross section along an XY plane of the trench structure TST will be described with reference to FIG. 5.

Figure 5:
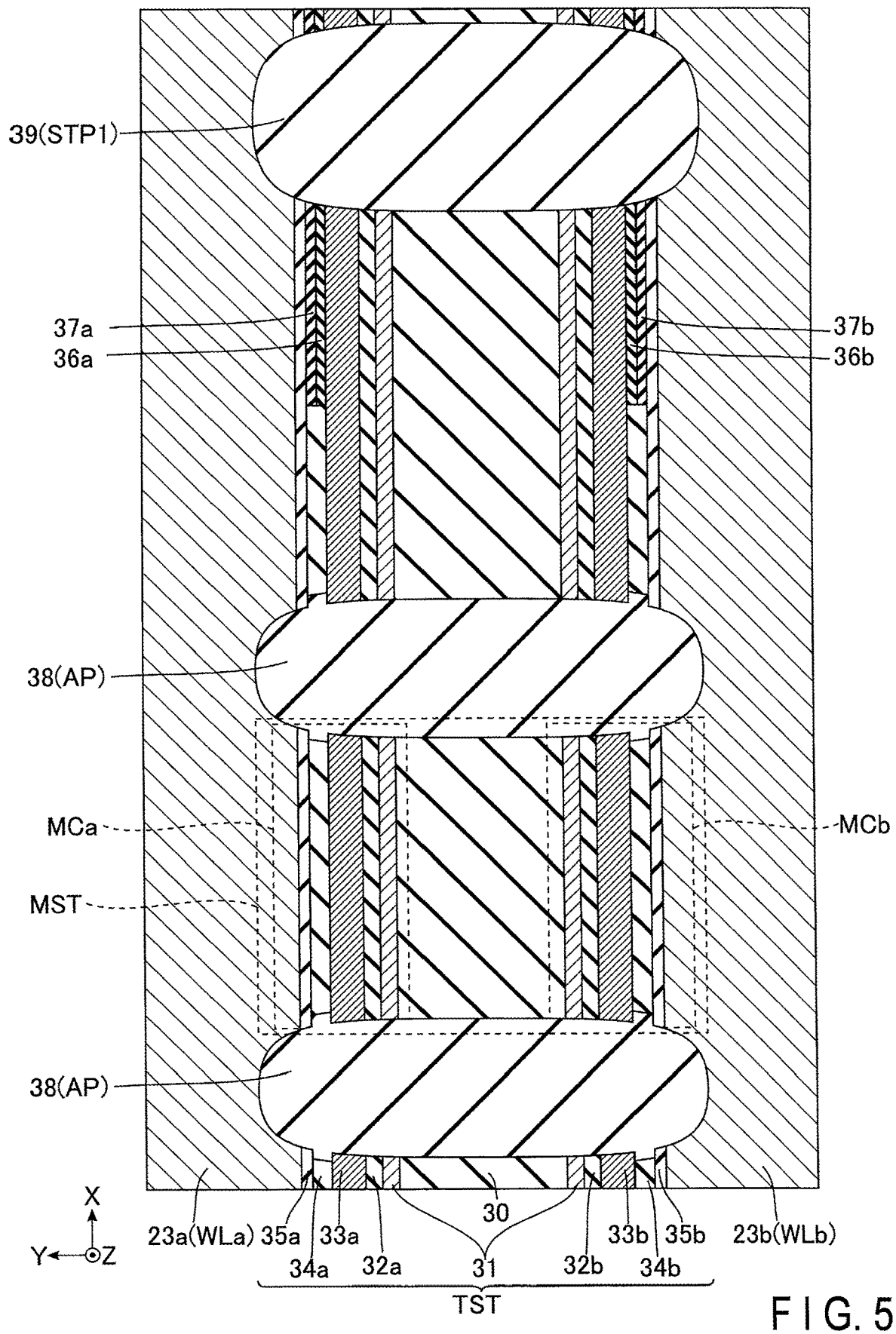
FIG. 5 is a transverse cross-sectional view of a region V shown in FIG. 3 of the transverse cross-sectional view of the memory cell array, taken along line V-V in FIG. 4.

FIG. 5 is a transverse cross-sectional view of a region V shown in FIG. 3 of the transverse cross-sectional view of the memory cell array taken along line V-V in FIG. 4. FIG. 5 shows a configuration including the trench structure TST that includes the memory structure MST shown in FIG. 4, two pillars AP sandwiching the memory structure MST, and a pillar STP1, and conductors 23a and 23b that sandwich the trench structure TST.

As shown in FIG. 5, the trench structure TST is provided between the conductor 23a and the conductor 23b arranged alongside each other in the Y direction. The trench structure TST is separated by a plurality of pillars AP and at least one pillar STP1 arranged alongside each other in the X direction.

Insulators 38 functioning as the pillars AP and the insulator 39 functioning as the pillar STP1 include, for example, silicon oxide, and have an elliptical shape in a plan view.

Of the trench structure TST, the part sandwiched between the two insulators 38 includes the core member 30, the semiconductor 31, the tunnel insulating films 32a and 32b, the charge storage films 33a and 33b, the block insulating films 34a and 34b, and the block insulating films 35a and 35b, which extend in the X direction. Of the memory structure MST, the part that is in contact with the conductor 23a functions as the memory cell transistor MCa, and the part that is in contact with the conductor 23b functions as the memory cell transistor MCb.

Of the trench structure TST, the part sandwiched between the insulator 38 and the insulator 39 includes the core member 30, the semiconductor 31, the tunnel insulating films 32a and 32b, the charge storage films 33a and 33b, the block insulating films 34a and 34b, the block insulating films 35a and 35b, sacrificial members 36a and 36b, and sacrificial members 37a and 37b. Of these members, the core member 30, the semiconductor 31, the tunnel insulating films 32a and 32b, the charge storage films 33a and 33b, and the block insulating films 35a and 35b extend in the X direction from the insulator 38 to reach the insulator 39. On the other hand, the block insulating films 34a and 34b extend in the X direction from the insulator 38, but terminate before they reach the insulator 39. On an extension of the block insulating film 34a, from the termination of the block insulating film 34a to the insulator 39, the sacrificial member 36a is provided in contact with the charge storage film 33a, and the sacrificial member 37a is provided in contact with the block insulating film 35a. On an extension of the block insulating film 34b, from the termination of the block insulating film 34b to the insulator 39, the sacrificial member 36b is provided in contact with the charge storage film 33b, and the sacrificial member 37b is provided in contact with the block insulating film 35b. Thus, of the trench structure TST sandwiched between the insulator 38 and the insulator 39, on the insulator 38 side, the block insulating film 35a, the block insulating film 34a, the charge storage film 33a, the tunnel insulating film 32a, the semiconductor 31, the core member 30, the semiconductor 31, the tunnel insulating film 32b, the charge storage film 33b, the block insulating film 34b, and the block insulating film 35b are arranged in this order in the Y direction. On the insulator 39 side, the block insulating film 35a, the sacrificial member 37a, the sacrificial member 36a, the charge storage film 33a, the tunnel insulating film 32a, the semiconductor 31, the core member 30, the semiconductor 31, the tunnel insulating film 32b, the charge storage film 33b, the sacrificial members 36b, the sacrificial members 37b, and the block insulating film 35b are arranged in this order in the Y direction.

Although not shown in FIG. 5, in a cross section along the YZ plane of a portion including the sacrificial members 36a and 37a of the trench structure TST, the sacrificial member 36a covers the charge storage film 33a, the sacrificial member 37a covers the sacrificial member 36a, and the block insulating film 35a covers the sacrificial member 37a in each of the layers provided with the conductors 22a to 24a. In a cross section along the YZ plane of a portion including the sacrificial members 36b and 37b of the trench structure TST, the sacrificial member 36b covers the charge storage film 33b, the sacrificial member 37b covers the sacrificial member 36b, and the block insulating film 35b covers the sacrificial member 37b in each of the layers provided with the conductors 22b to 24b.

The sacrificial members 36a and 36b include, for example, silicon oxide doped with boron (B) or phosphorus (P), and the sacrificial members 37a and 37b include, for example, silicon nitride (SiN). During etching that can selectively remove silicon oxide, the sacrificial members 37a and 37b, if doped with boron or phosphorus, exhibit a higher etching rate than a silicon oxide (non-doped) not doped with boron or phosphorus.

1.2 Method of Manufacturing Memory Device

An example of steps of manufacturing the memory array of the memory device according to the first embodiment will be described. Each of FIG. 6 to FIG. 27 shows an example of a cross-sectional structure including a structure corresponding to the memory cell array in the manufacturing process of the memory device according to the first embodiment. The cross-sectional views showing the manufacturing steps referred to below include cross-sections perpendicular to the surface of the semiconductor substrate 20. The regions shown in the cross-sectional views of the respective manufacturing steps, except that shown in FIG. 27, correspond to the region shown in FIG. 4 or FIG. 5.

Figure 6:
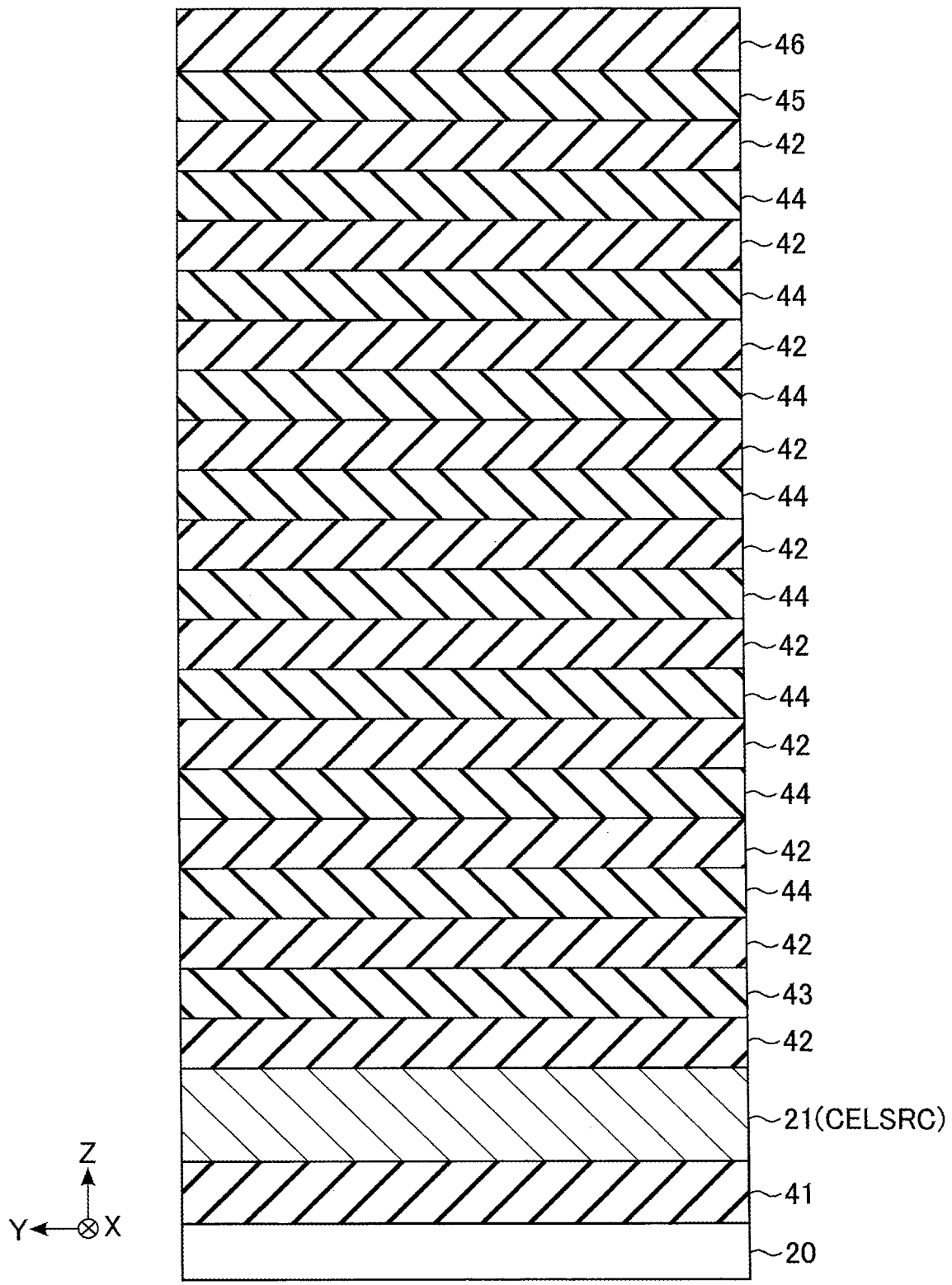
FIG. 6 is a vertical cross-sectional view of the memory cell array for explaining a step of manufacturing the memory device according to the first embodiment.

First, as shown in FIG. 6, a sacrificial member 43, eight sacrificial members 44, and a sacrificial member 45 respectively corresponding to the select gate line SGS, the word lines WL0 to WL7, and the select gate line SGD are stacked. Specifically, first, an insulator 41 and the conductor 21 are stacked in sequence on the semiconductor substrate 20. An insulator 42 and a sacrificial member 43 are stacked in sequence on the conductor 21. Insulators 42 and sacrificial members 44 are alternately stacked on the sacrificial member 43 a plurality of times (eight times in the example of FIG. 6). An insulator 42 and a sacrificial member 45 are stacked in sequence on the sacrificial member 44. Then, an insulator 46 is further stacked on the sacrificial member 45. The insulator 46 corresponds to a portion in which the joint portion JCT is formed.

The insulators 41, 42, and 46 include, for example, silicon oxide, and the sacrificial members 43, 44, and 45 include, for example, silicon nitride. The number of layers in which the sacrificial members 43, 44, and 45 are formed corresponds to the number of select gate lines SGS, word lines WL, and select gate lines SGD that are stacked.

Figure 7:
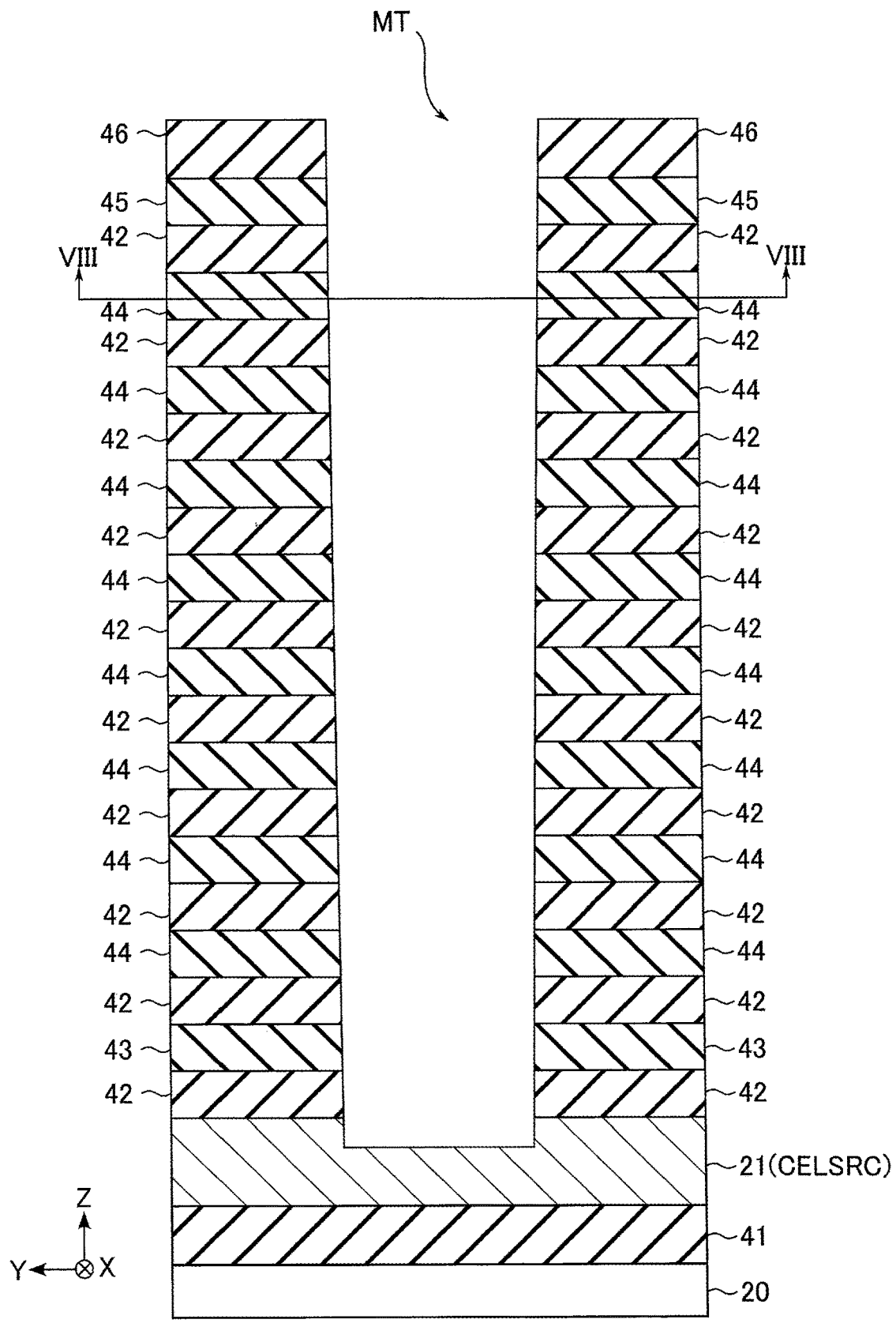
FIG. 7 is a vertical cross-sectional view of the memory cell array for explaining a step of manufacturing the memory device according to the first embodiment.

Next, as shown in FIG. 7, a region where the trench structure TST is to be formed is removed from a layer stack formed in the step shown in FIG. 6, thereby forming a trench MT. Specifically, first, a mask in which regions corresponding to the trench structure TST are opened is formed by lithography. The trenches MT are formed by anisotropic etching using the formed mask. The bottom end of the trench MT reaches the conductor 21, for example. The anisotropic etching in this step is, for example, reactive ion etching (RIE).

Figure 8:
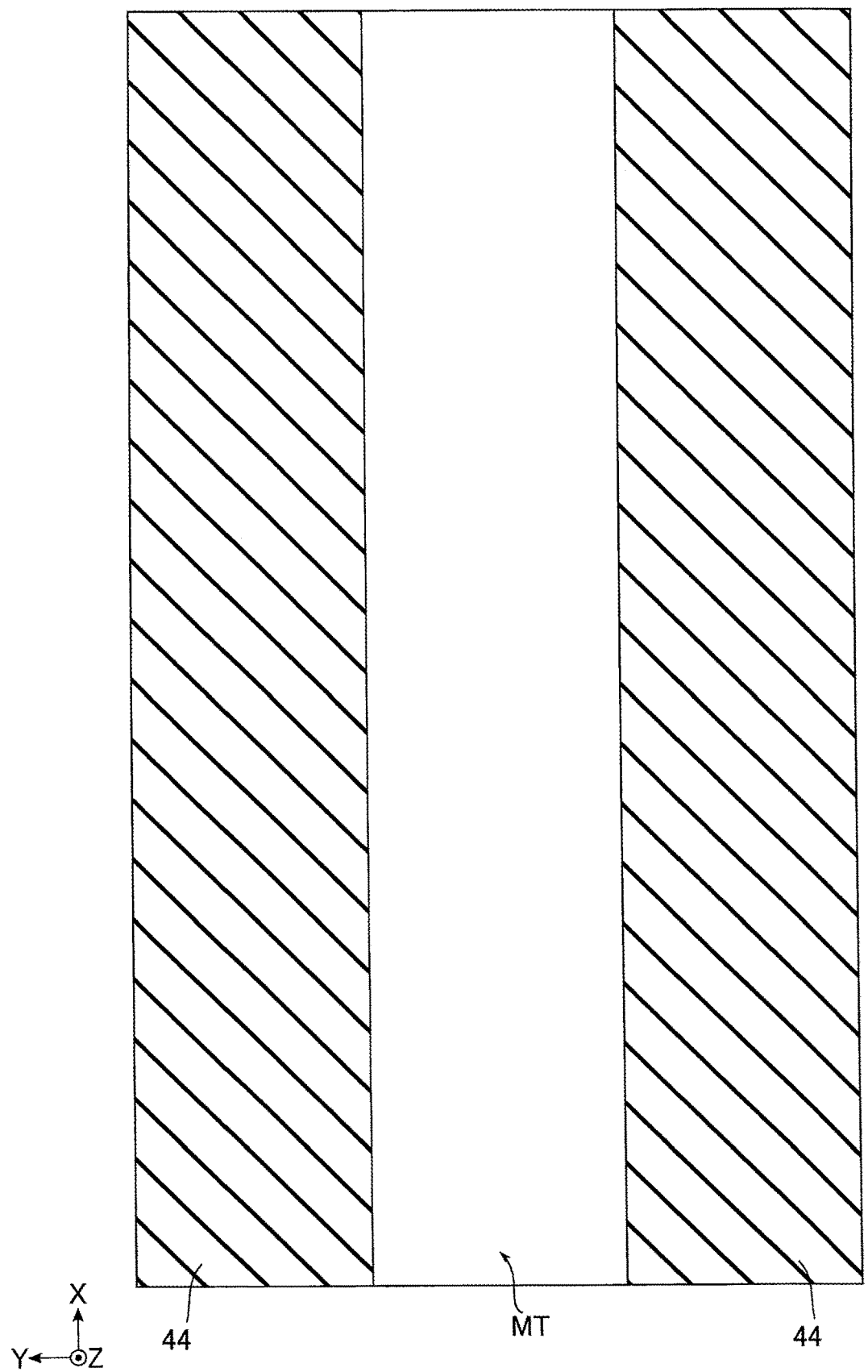
FIG. 8 is a transverse cross-sectional view of the memory cell array, taken along line VIII-VIII in FIG. 7.

FIG. 8 is a cross-sectional view of the memory cell array 10, taken along line VIII-VIII in FIG. 7. As shown in FIG. 8, through this step, a line-and-space shape is formed in which a part of the layer stack including the sacrificial members 44 and the trenches MT are arranged alternately alongside in the Y direction. As shown in FIG. 3, the stacked wiring extends longer than the trench structures TST in the X direction, and the part of the layer stack including the sacrificial members 44 is not separated by the trench MT.

Figure 9:
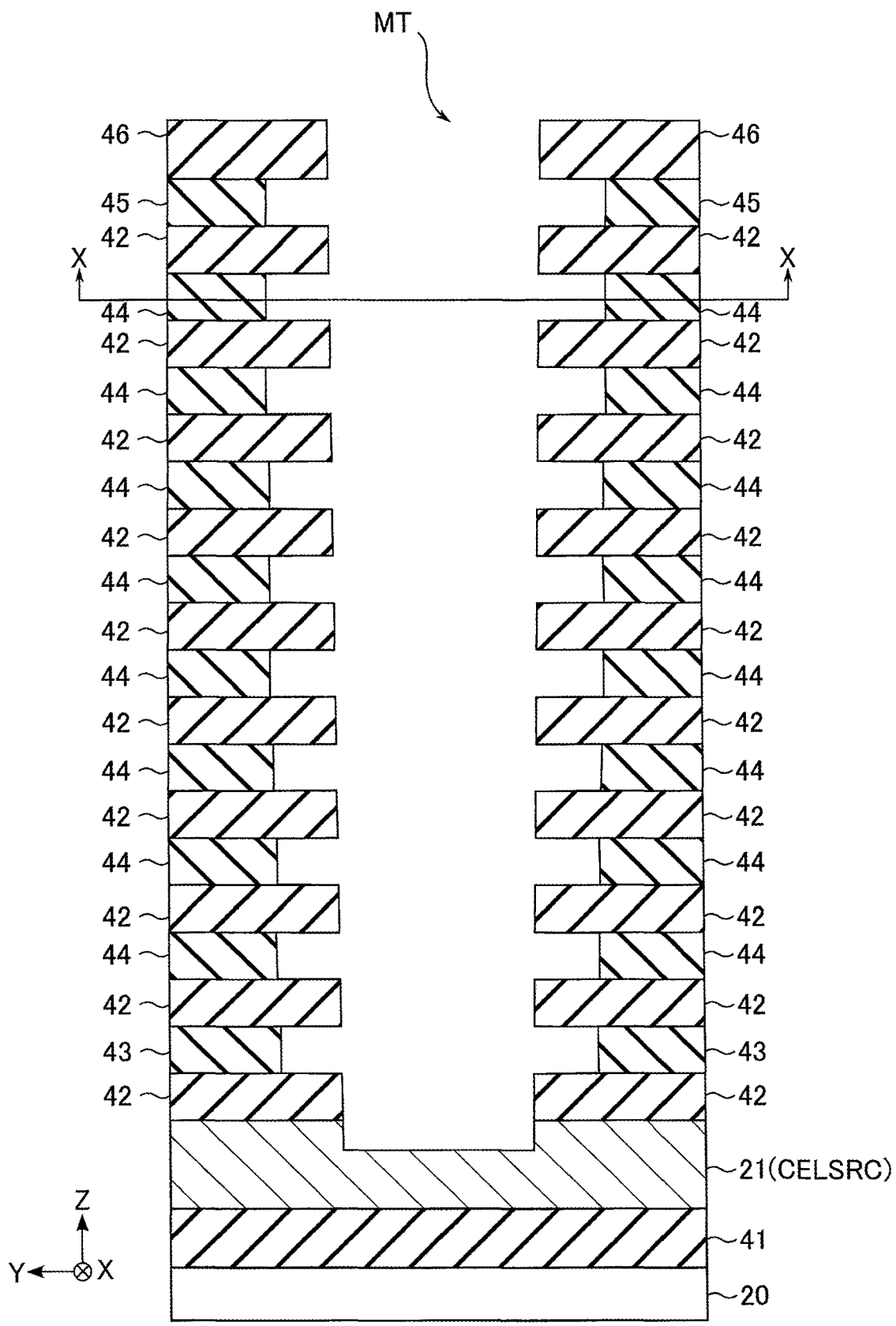
FIG. 9 is a vertical cross-sectional view of the memory cell array for explaining a step of manufacturing the memory device according to the first embodiment.

Next, as shown in FIG. 9, parts of the sacrificial members 43, 44, and 45 exposed in the trench MT are selectively removed via the trench MT by, for example, wet etching. Through the etching in this step, recesses extending the Y direction that expose an upper surface of the lowermost insulator 42, upper and lower surfaces of all insulators 42 except for the lowermost insulator 42, and a lower surface of the insulator 46 are formed in the layers provided with the sacrificial members 43, 44, and 45 in the trench MT.

Figure 10:
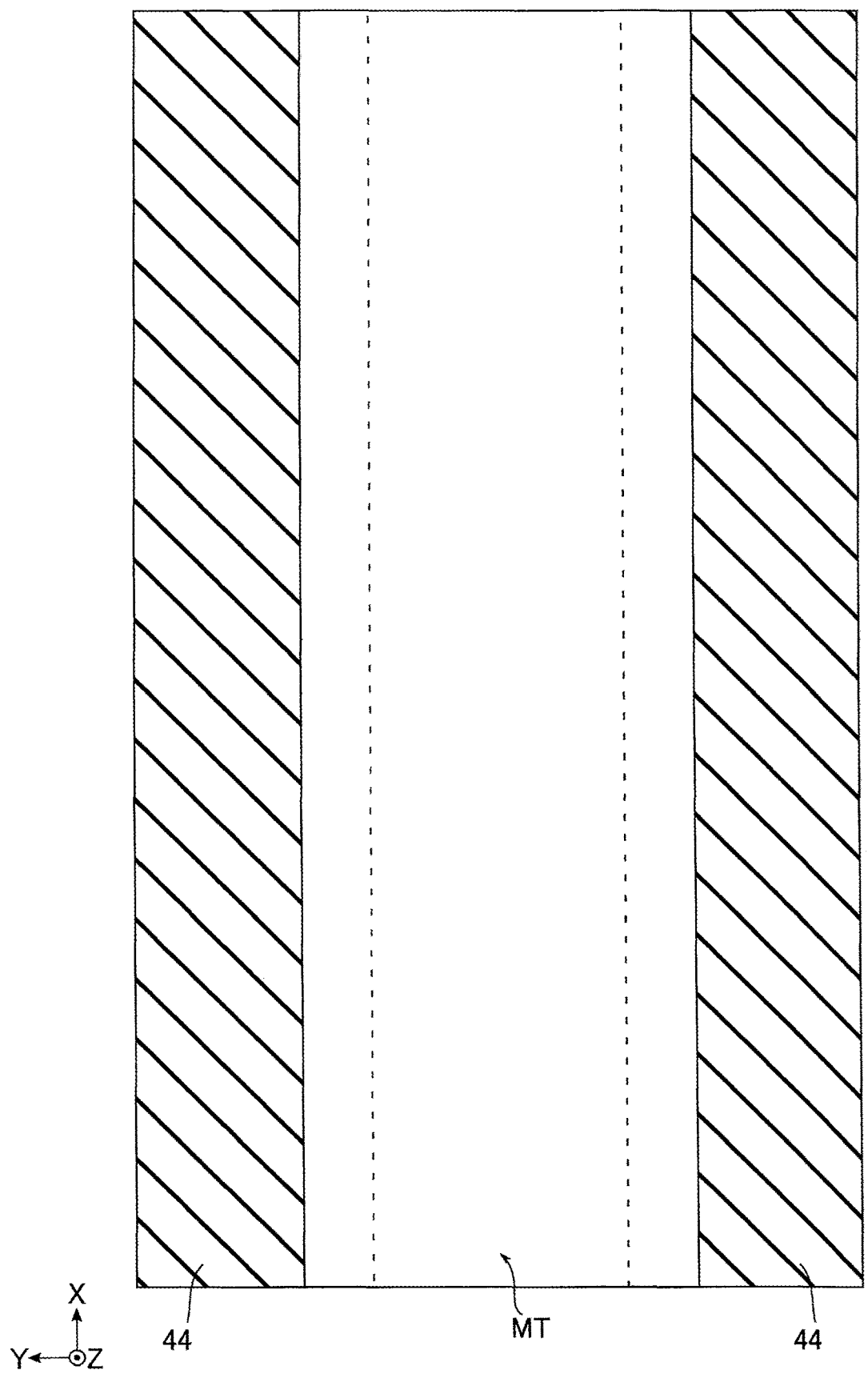
FIG. 10 is a transverse cross cross-sectional view of the memory cell array, taken along line X-X in FIG. 9.

FIG. 10 is a cross-sectional view of the memory cell array 10, taken along line X-X in FIG. 9. In FIG. 10, an opening diameter of the insulators 42 and 46 is indicated by broken lines. As shown in FIG. 10, through this step, the opening diameters of the sacrificial members 43, 44, and 45 in the trench MT become wider than those of the insulators 42 and 46.

Figure 11:
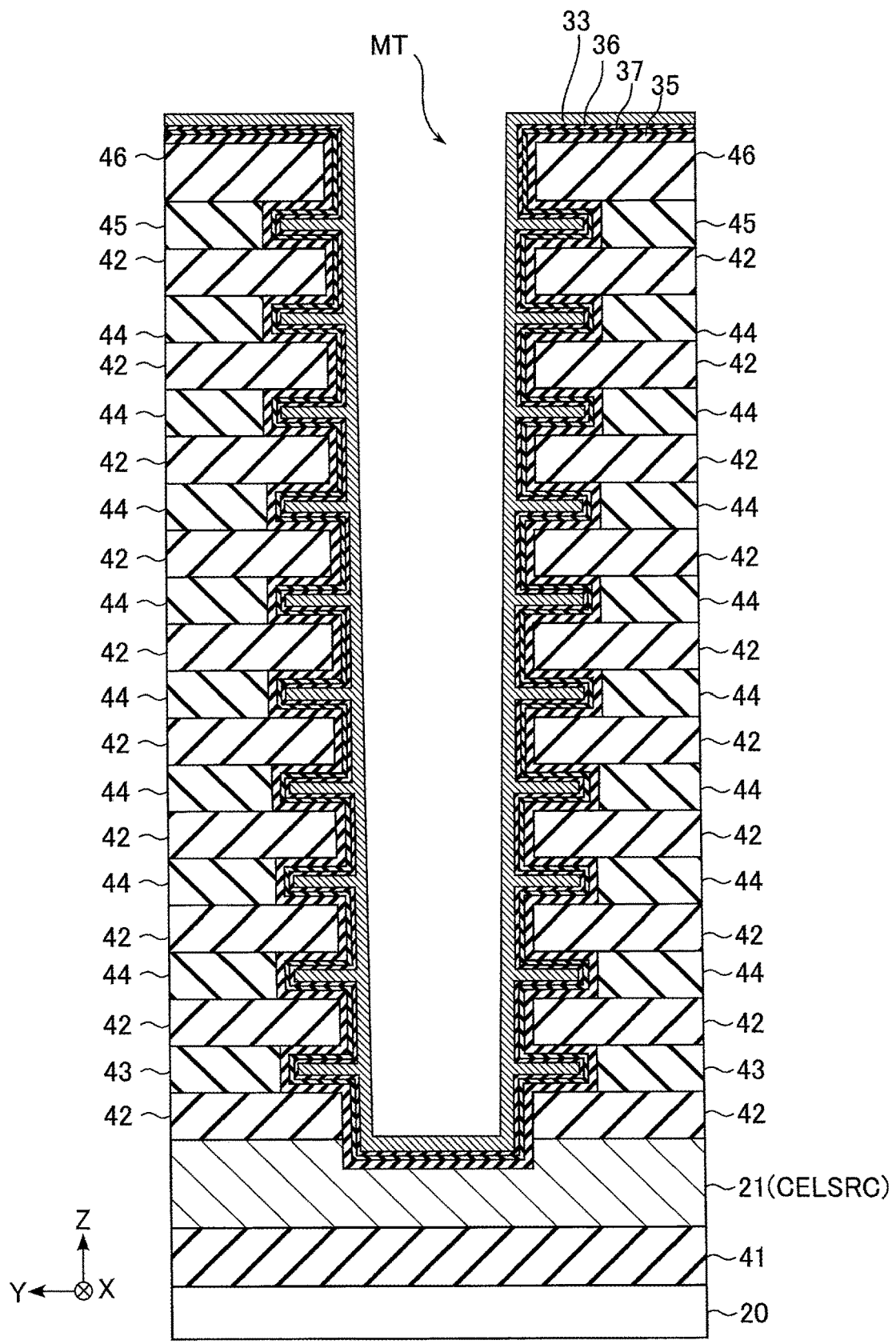
FIG. 11 is a vertical cross-sectional view of the memory cell array for explaining a step of manufacturing the memory device according to the first embodiment.

Next, as shown in FIG. 11, the block insulating film 35, the sacrificial member 37, the sacrificial member 36, and the charge storage film 33 are formed on the overall surface including the interior of the trench MT. The thicknesses of these films are adjusted so that the block insulating film 35, the sacrificial member 37, and the sacrificial member 36 do not fill the recesses formed in the trench MT by the step shown in FIG. 9, while the charge storage film 33 fills the recesses.

Figure 12:
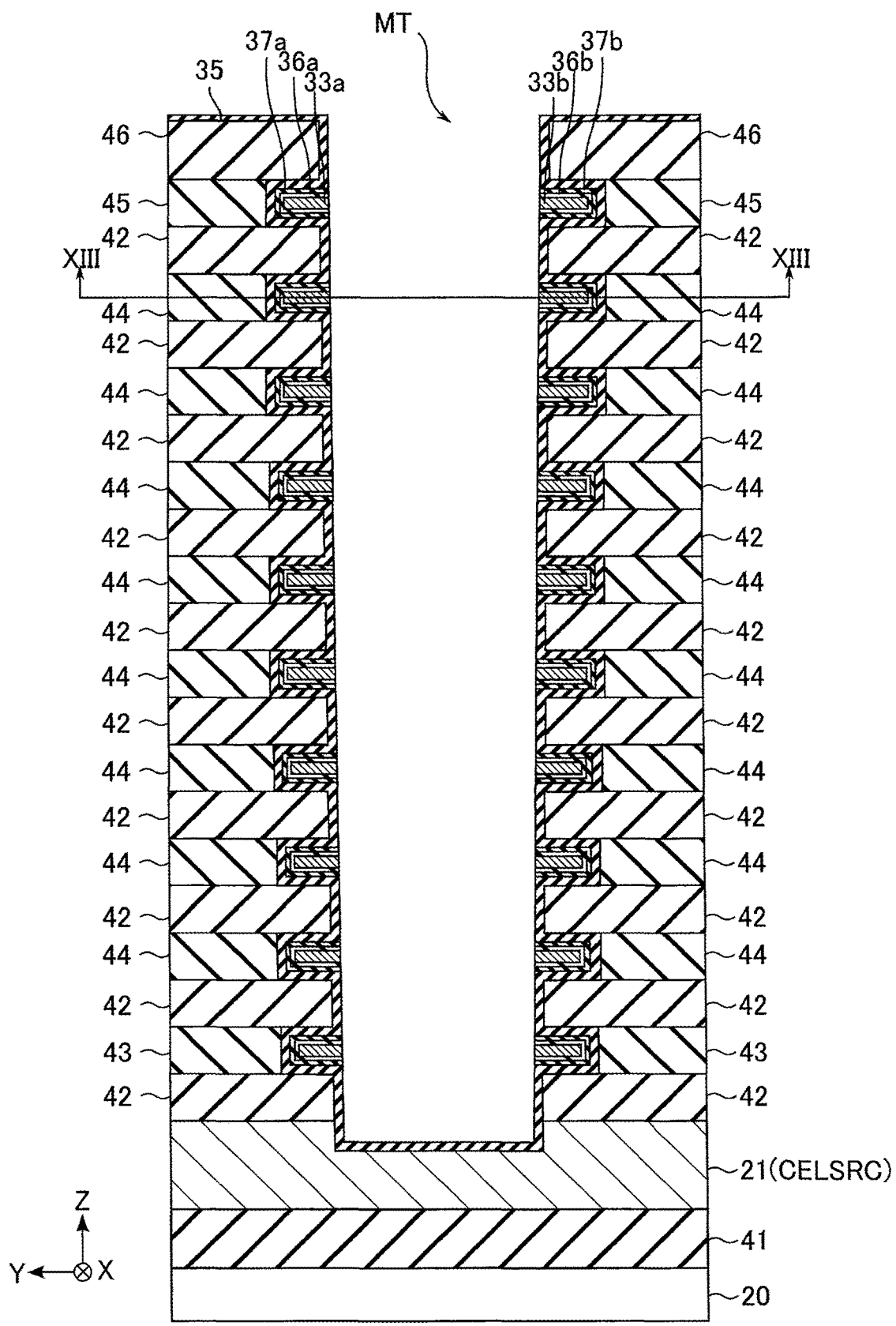
FIG. 12 is a vertical cross-sectional view of the memory cell array for explaining a step of manufacturing the memory device according to the first embodiment.

Next, as shown in FIG. 12, parts of the charge storage film 33, parts of the sacrificial member 37, and parts of the sacrificial member 36 are sequentially removed.

More specifically, first, isotropic etching that can selectively remove the charge storage film 33 is executed. The selective etching of the charge storage film 33 is executed until the sacrificial member 37 becomes exposed in the layers where the insulators 42 and 46 are formed in the trench MT. As a result, the charge storage film 33 is divided to remain in the trench MT in the layers where the sacrificial members 43, 44, and 45 are respectively formed, so that portions 33a and 33b remain in the recesses formed by the step shown in FIG. 9.

Subsequently, isotropic etching that can selectively remove the sacrificial member 37 is executed. The selective etching of the sacrificial member 37 is executed until the sacrificial member 36 becomes exposed in the layers where the insulators 42 and 46 are formed in the trench MT. As a result, the sacrificial member 37 is divided to remain in the trench MT in the layers where the sacrificial members 43, 44, and 45 are respectively formed, so that portions 37a and 37b remain in the recesses formed by the step shown in FIG. 9.

Subsequently, isotropic etching that can selectively remove the sacrificial member 36 is executed. The selective etching of the sacrificial member 36 is executed until the block insulating film 35 becomes exposed in the layers where the insulators 42 and 46 are formed in the trench MT. As a result, the sacrificial member 36 is divided to remain in the trench MT in the layers where the sacrificial members 43, 44, and 45 are respectively formed, so that portions 36a and 36b remain in the recesses formed by the step shown in FIG. 9.

Figure 13:
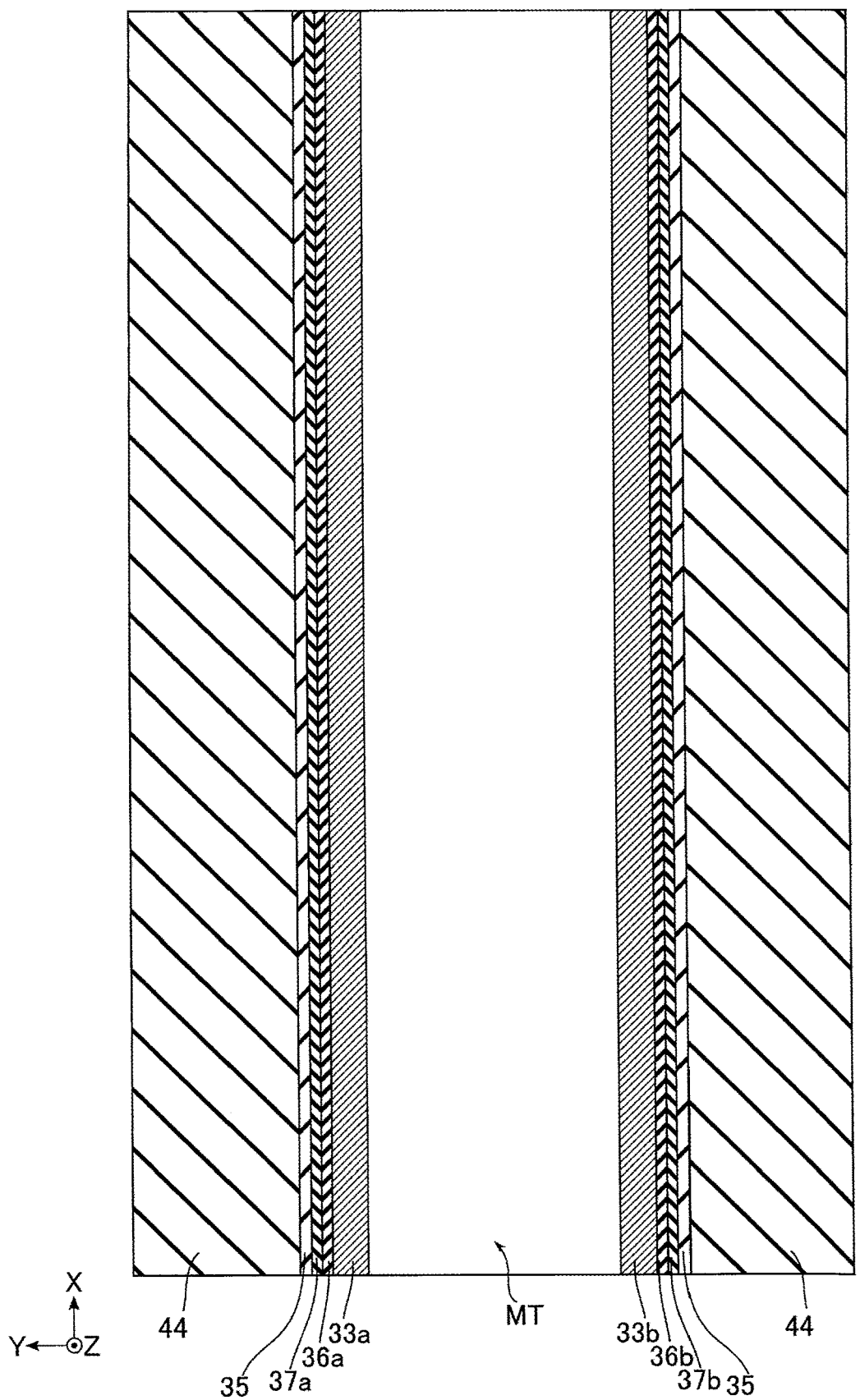
FIG. 13 is a transverse cross-sectional view of the memory cell array, taken along line XIII-XIII in FIG. 12.

FIG. 13 is a cross-sectional view of the memory cell array 10, taken along line XIII-XIII in FIG. 12. As shown in FIG. 13, through this step, in the layers in which the sacrificial members 43, 44, and 45 are formed in the trench MT, the block insulating film 35, the sacrificial member 37a (37b), the sacrificial member 36a (36b), and the charge storage film 33a (33b) are sequentially formed alongside each other in the Y direction between the sacrificial member 44 and the trench MT.

Figure 14:
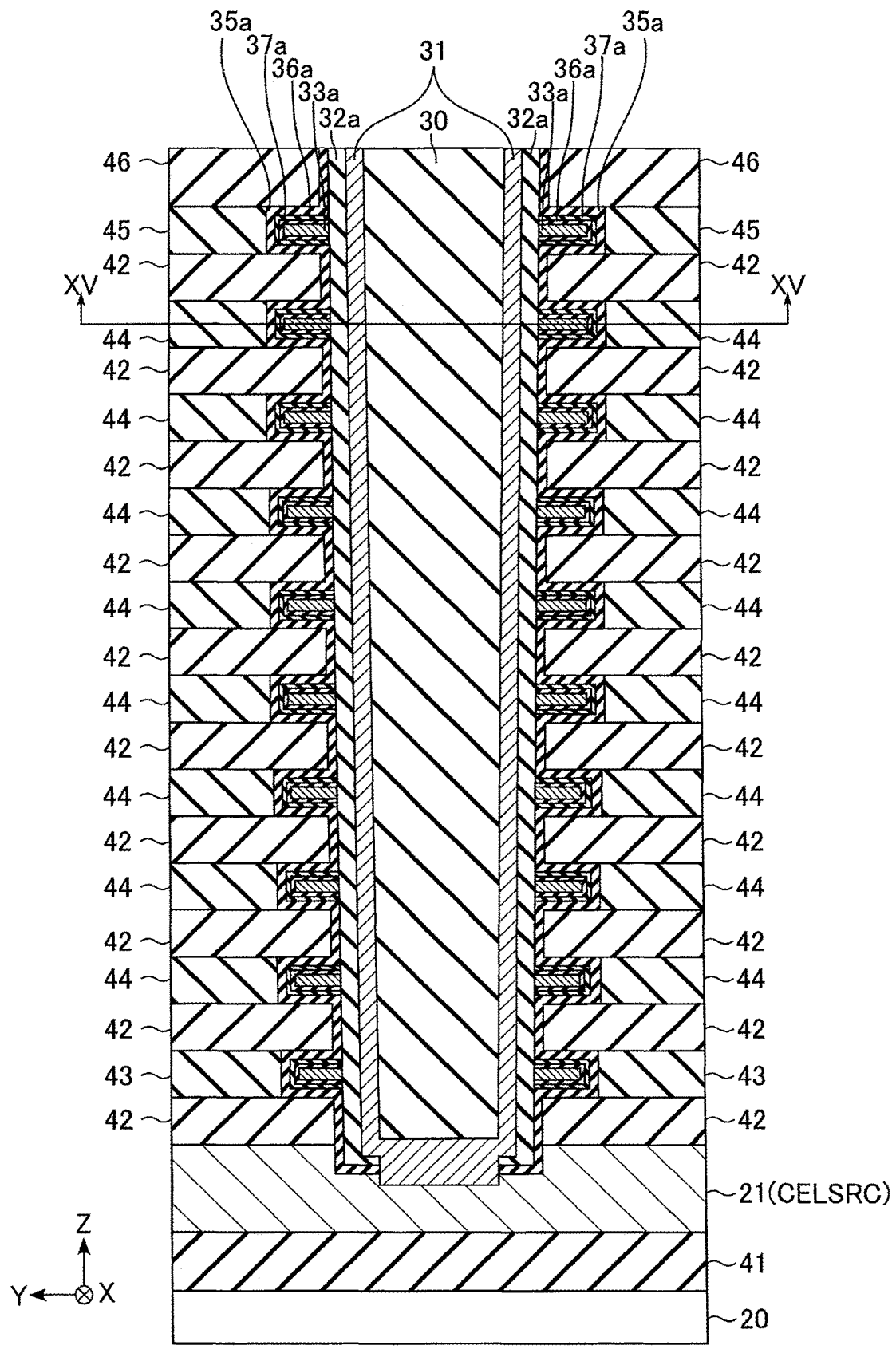
FIG. 14 is a vertical cross-sectional view of the memory cell array for explaining a step of manufacturing the memory device according to the first embodiment.

Subsequently, as shown in FIG. 14, the tunnel insulating films 32a and 32b, the semiconductor 31, and the core member 30 are further formed to fill the trench MT. Specifically, after a continuous film including the tunnel insulating films 32a and 32b is formed, the continuous film formed on the bottom end of the trench MT and the block insulating film 35 are removed to expose the conductor 21. As a result, the block insulating film 35 is divided into a part 35a, which is in contact with the sacrificial members 37a, and a part 35b, which is in contact with the sacrificial members 37b. In addition, the continuous film including the tunnel insulating films 32a and 32b is divided into a part 32a, which is in contact with the charge storage films 33a, and a part 32b, which is in contact with the charge storage films 33b. The etching in this step is, for example, RIE.

Subsequently, the semiconductor 31 is formed in the trench MT. Accordingly, the semiconductor 31 is in contact with a plurality of conductors 21 while maintaining a portion sandwiching the tunnel insulating film 32a between the semiconductor 31 and the charge storage films 33a and a portion sandwiching the tunnel insulating film 32b between the semiconductor 31 and the charge storage films 33b.

Subsequently, after the core member 30 is formed to fill the trench MT, the structure is flattened by chemical mechanical polishing (CMP) or the like, thereby removing the portion above the insulator 46.

Figure 15:
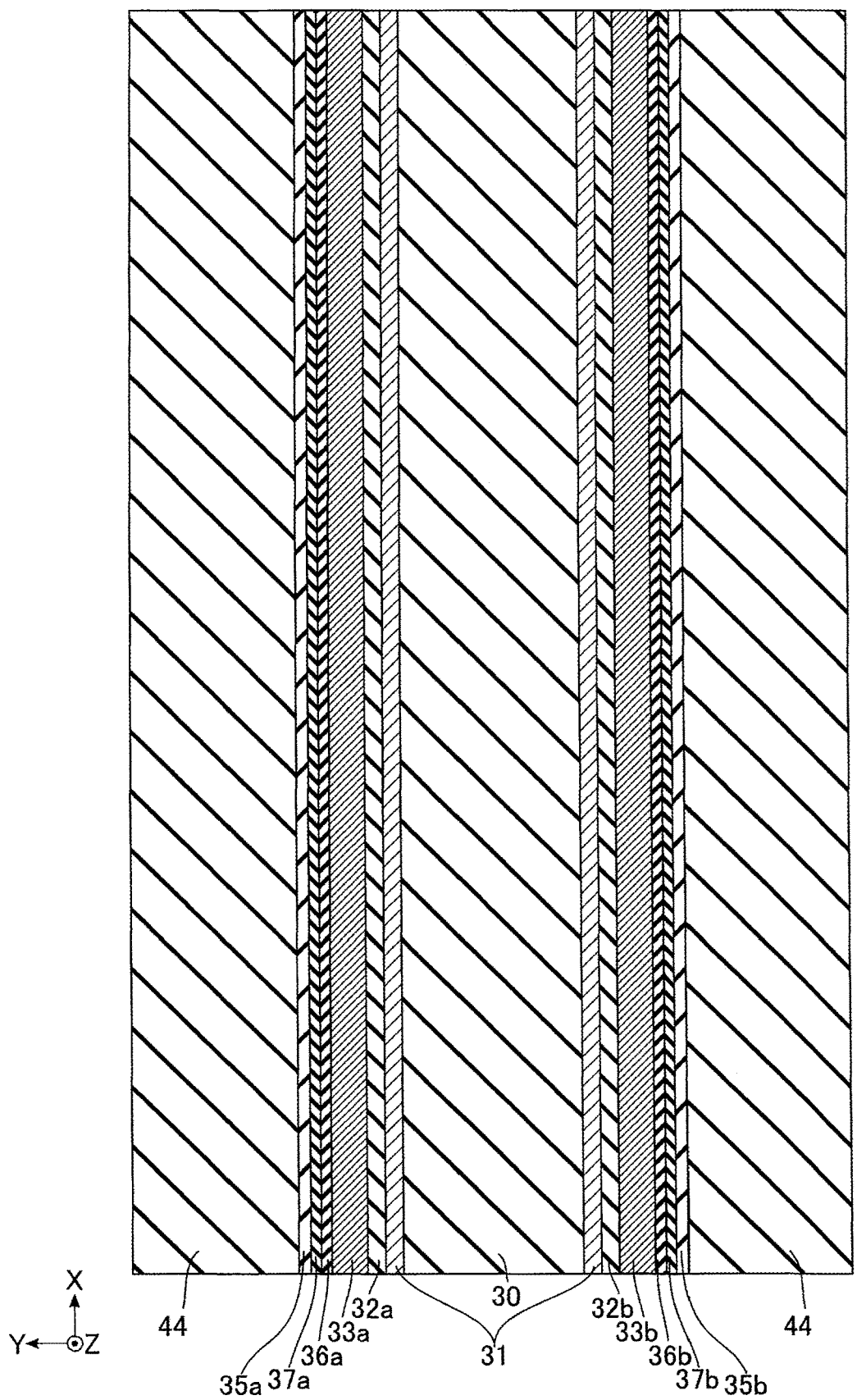
FIG. 15 is a transverse cross-sectional view of the memory cell array, taken along line XV-XV in FIG. 14.

FIG. 15 is a cross-sectional view of the memory cell array 10, taken along line XV-XV in FIG. 14. As shown in FIG. 15, through the step described above, the block insulating film 35a, the sacrificial member 37a, the sacrificial member 36a, the charge storage film 33a, the tunnel insulating film 32a, the semiconductor 31, the core member 30, the semiconductor 31, the tunnel insulating film 32b, the charge storage film 33b, the sacrificial member 36b, the sacrificial member 37b, and the block insulating film 35b are formed in sequence alongside in the Y direction in a space in the sacrificial member 44.

Figure 16:
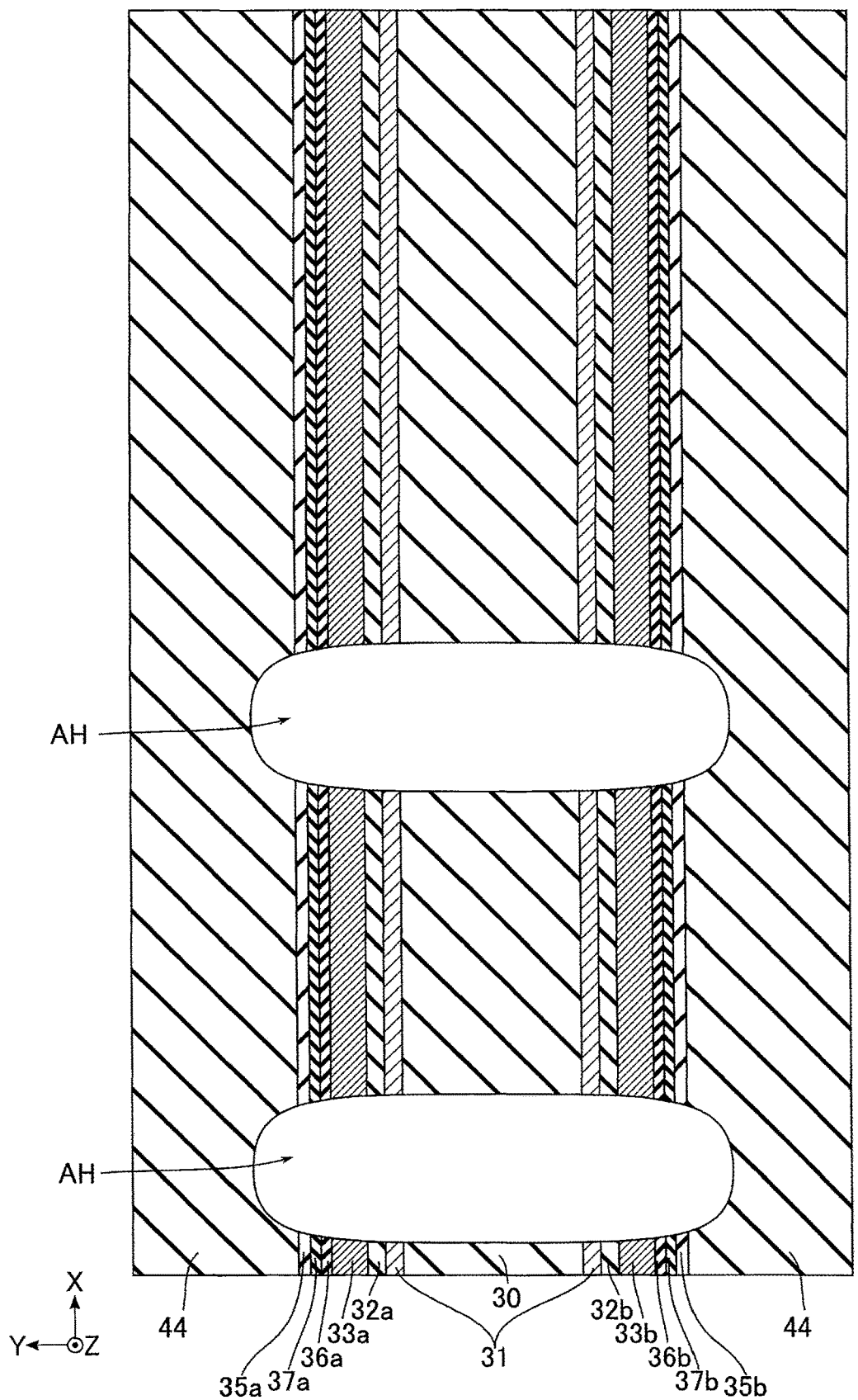
FIG. 16 is a transverse cross-sectional view of the memory cell array for explaining a step of manufacturing the memory device according to the first embodiment.

Next, as shown in FIG. 16, a plurality of holes AH are formed to separate the structure that fills the trench MT in the X direction. In each of the holes AH, ends of the sacrificial members 36a, 37a, 36b, and 37b extending in the X direction are exposed. The etching in this step is anisotropic etching, such as RIE, in which all materials of the structure filling the trench MT are etched at a similar rate.

Figure 17:
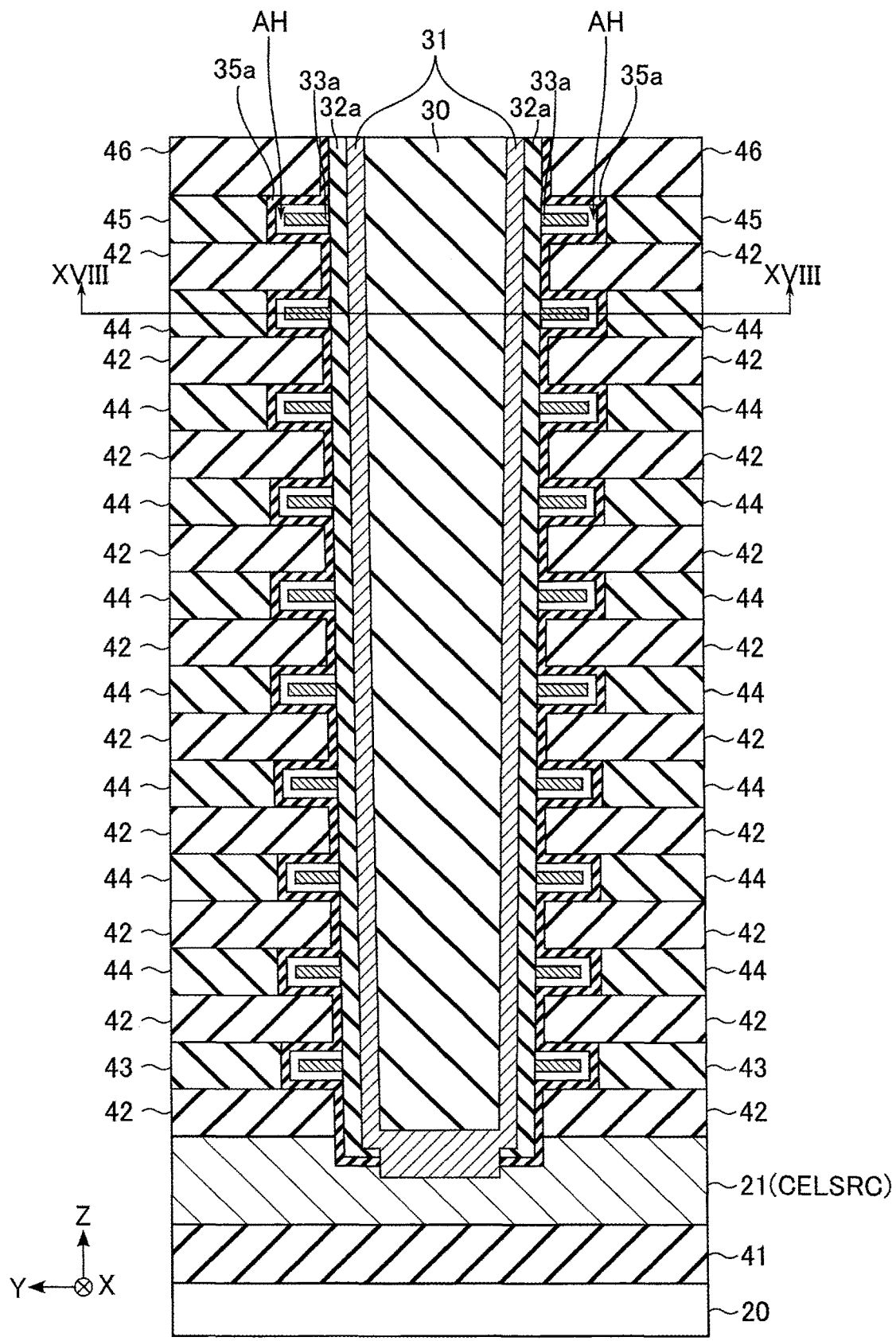
FIG. 17 is a vertical cross-sectional view of the memory cell array for explaining a step of manufacturing the memory device according to the first embodiment.

Next, as shown in FIG. 17, the sacrificial members 36a and 36b are selectively removed by either wet etching or dry etching via the holes AH. Since the sacrificial members 36a and 36b are formed of silicon oxide doped with boron or phosphorus as described above, the etching rate for selective removal of silicon dioxide is higher than that in non-doped silicon oxide. Accordingly, the sacrificial members 36a and 36b can be selectively removed before the insulators 42 and 46, the block insulating films 35a and 35b, and the tunnel insulating films 32a and 32b exposed in the holes AH are entirely removed.

Subsequently, the sacrificial members 37a and 37b are selectively removed by wet etching via the holes AH. Not only the sacrificial members 37a and 37b but also the sacrificial members 43, 44, and 45 are exposed in the holes AH; therefore, the sacrificial members 43, 44, and 45 are also removed in part by the etching in this step. However, since the sacrificial members 37a and 37b are have a thinness of around, for example, 1 nanometer (nm), the sacrificial members 37a and 37b can be selectively removed without substantially impairing the sacrificial members 43, 44, and 45.

Figure 18:
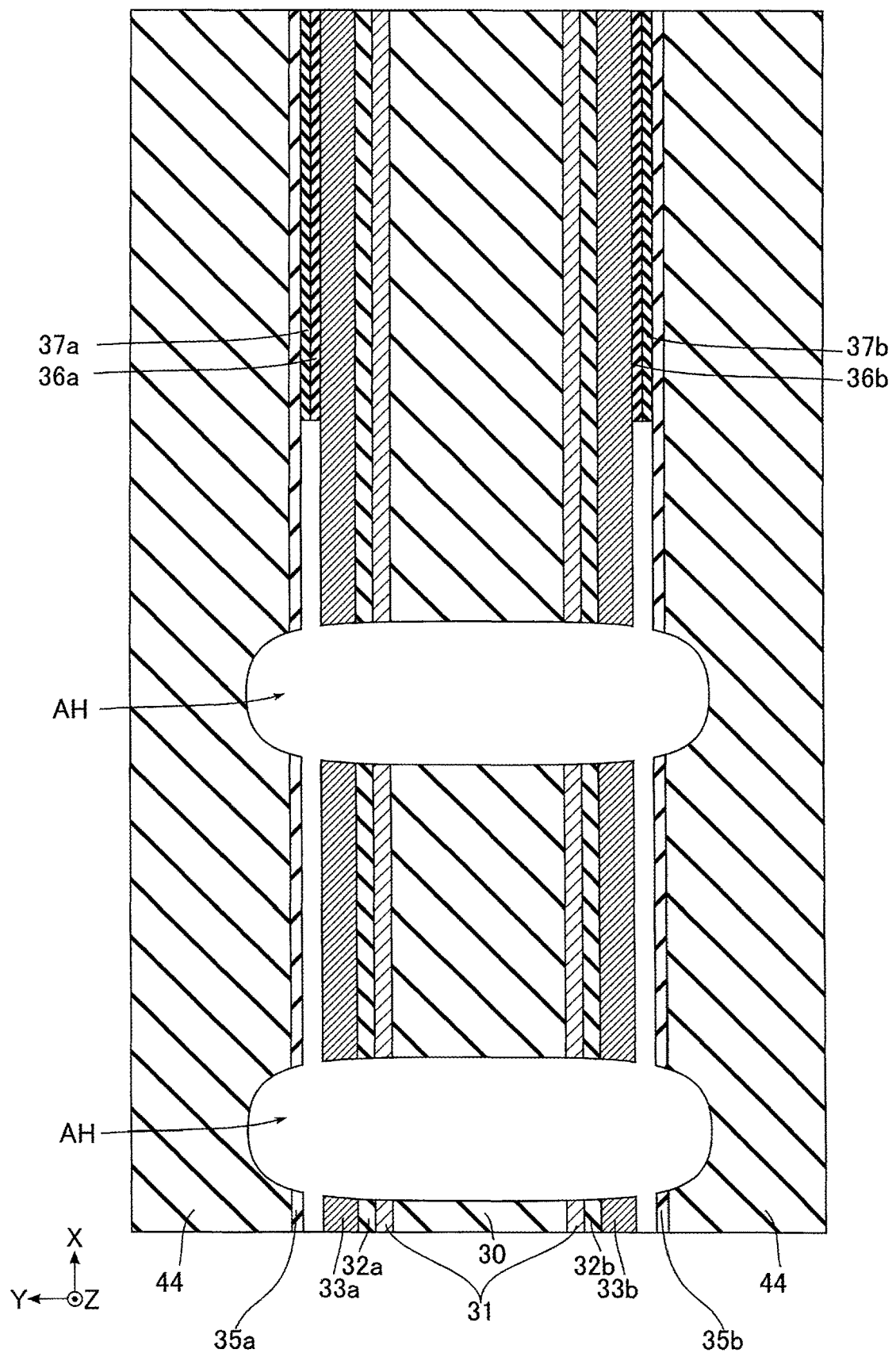
FIG. 18 is a transverse cross-sectional view of the memory cell array, taken along line XVIII-XVIII in FIG. 17.

FIG. 18 is a cross-sectional view of the memory cell array 10, taken along line XVIII-XVIII in FIG. 17. As shown in FIG. 18, through this step, the parts of the sacrificial members 36a, 36b, 37a, and 37b that are sandwiched between the two holes AH are completely removed. On the other hand, in the parts that are not sandwiched between the two holes AH, namely, a presumptive part to be sandwiched between a pillar AP and a pillar STP1, the sacrificial members 36a, 36b, 37a, and 37b are not removed from parts near the presumptive part where the pillar STP1 is to be formed.

Figure 19:
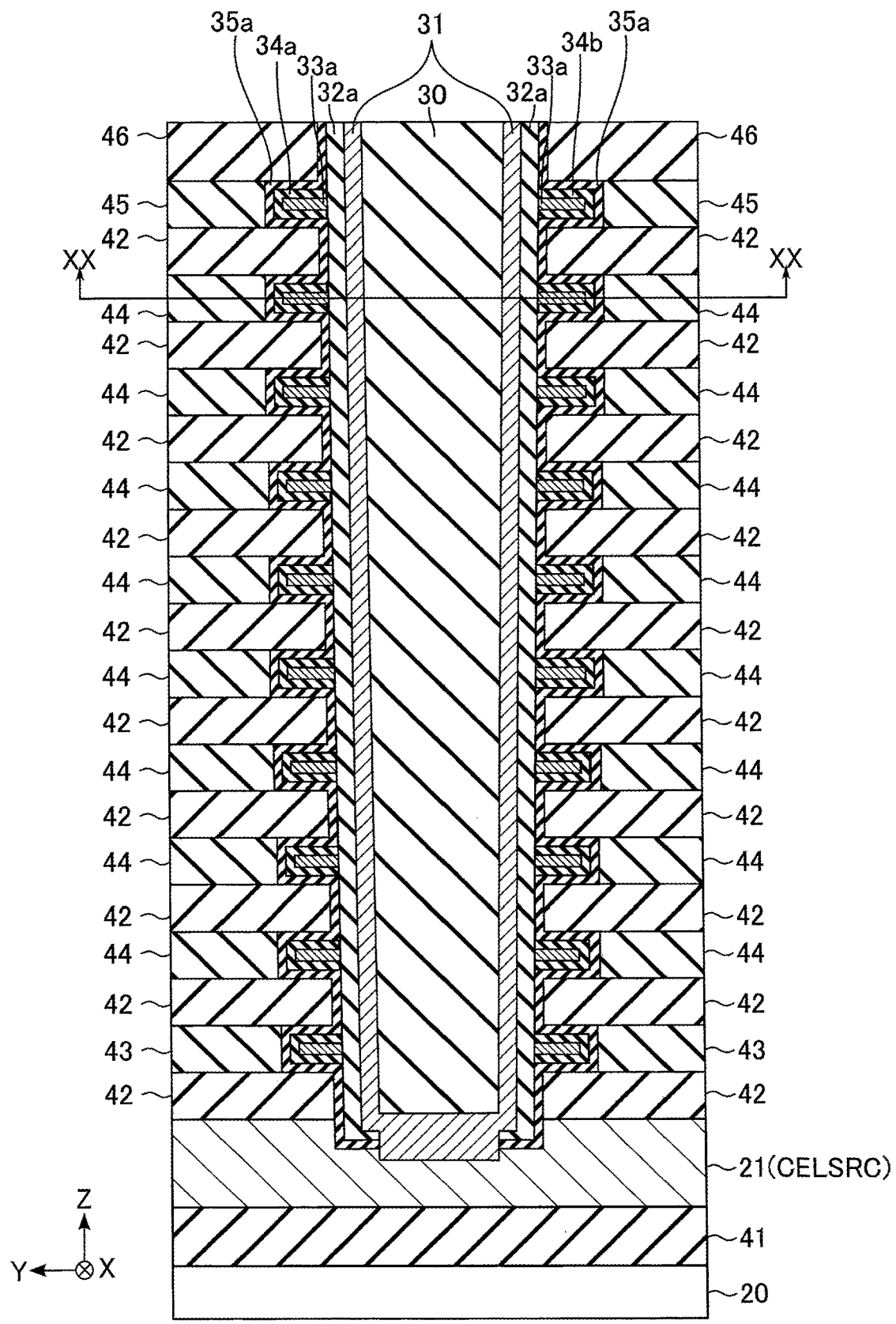
FIG. 19 is a vertical cross-sectional view of the memory cell array for explaining a step of manufacturing the memory device according to the first embodiment.

Next, as shown in FIG. 19, the block insulating film 34a is formed in a space from which the sacrificial members 36a and 37a have been removed via the hole AH and the block insulating film 34b is formed in a space from which the sacrificial members 36b and 37b have been removed via the hole AH in the step shown in FIG. 17. Specifically, after a continuous film including the block insulating films 34a and 34b is formed on inner walls of the holes AH, the continuous film is selectively etched by wet etching via the holes AH. As a result, the core member 30, the semiconductor 31, the tunnel insulating films 32a and 32b, the charge storage films 33a and 33b, the block insulating films 35a and 35b, and the sacrificial members 43, 44, and are exposed, and the continuous film is separated into a plurality of block insulating films 34a and a plurality of block insulating films 34b.

Figure 20:
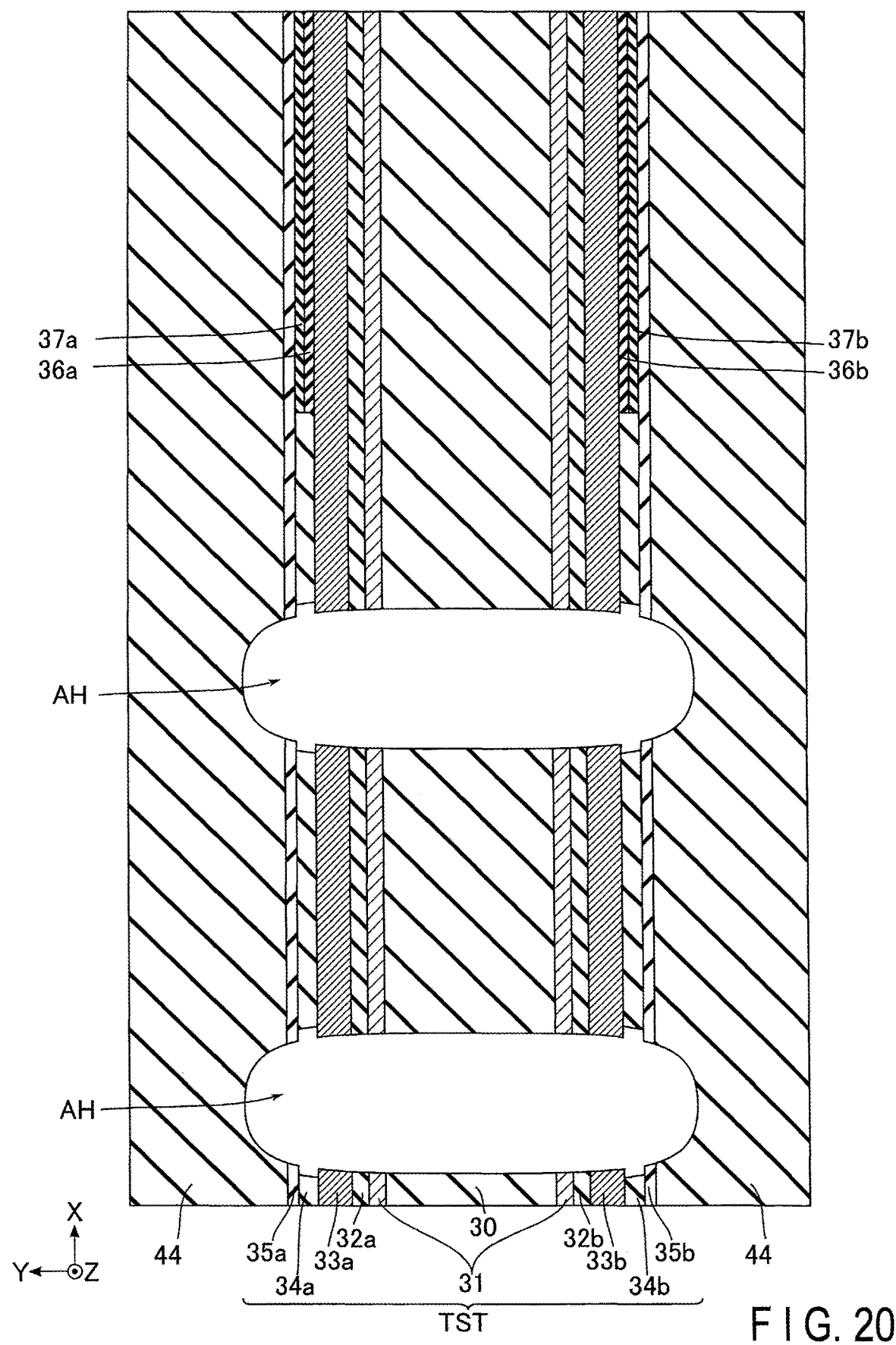
FIG. 20 is a transverse cross-sectional view of the memory cell array, taken along line XX-XX in FIG. 19.

FIG. 20 is a cross-sectional view of the memory cell array 10, taken along line XX-XX in FIG. 19. As shown in FIG. 20, through this step, the space from which the sacrificial members 36a, 36b, 37a, and 37b have been removed via the holes AH is filled with the block insulating films 34a and 34b.

Figure 21:
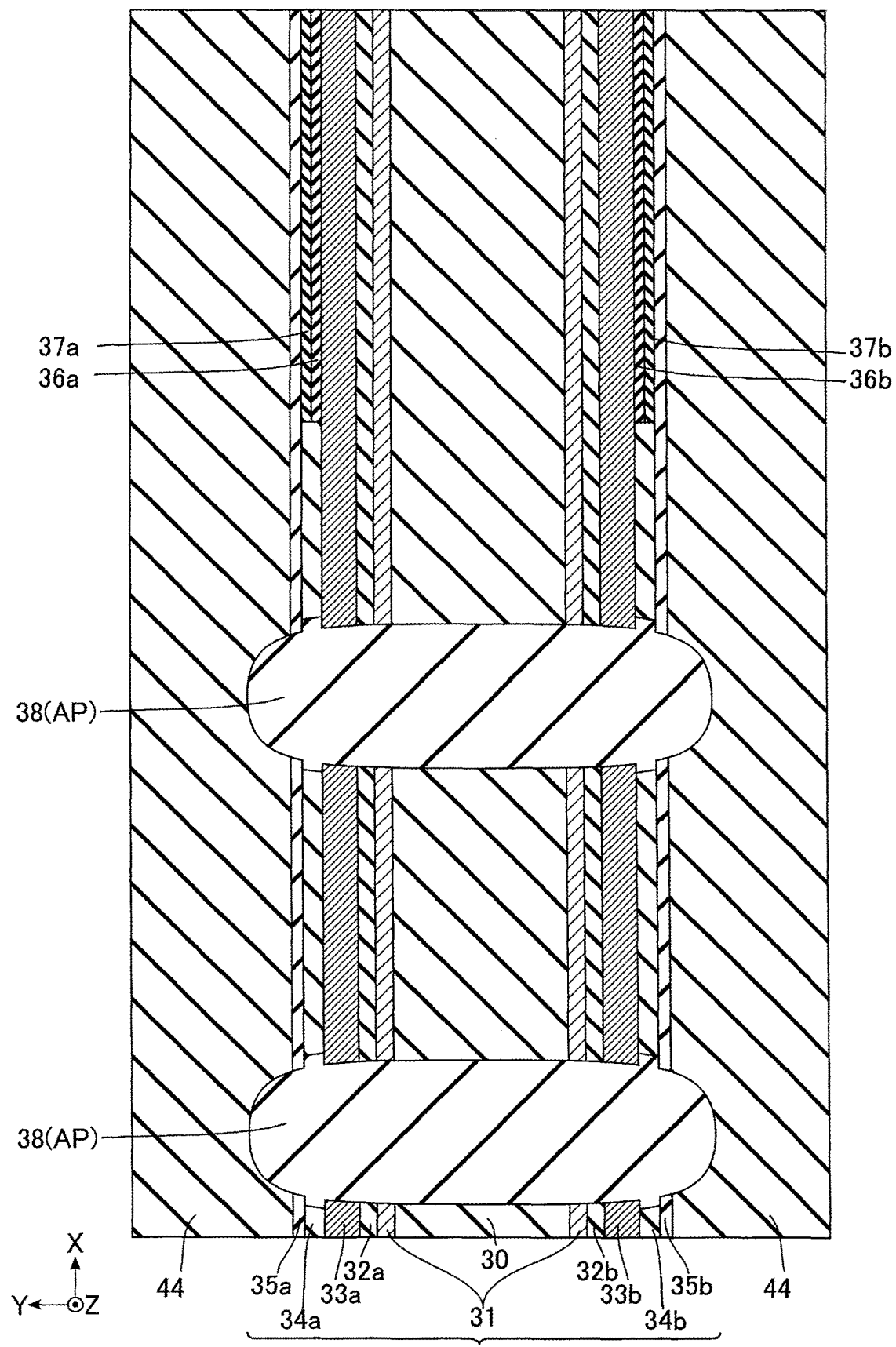
FIG. 21 is a transverse cross-sectional view of the memory cell array for explaining a step of manufacturing the memory device according to the first embodiment.

Next, after the holes AH are filled with the insulators 38 as shown in FIG. 21, the structure is flattened by CMP or the like, thereby removing the portion above the insulator 46.

Figure 22:
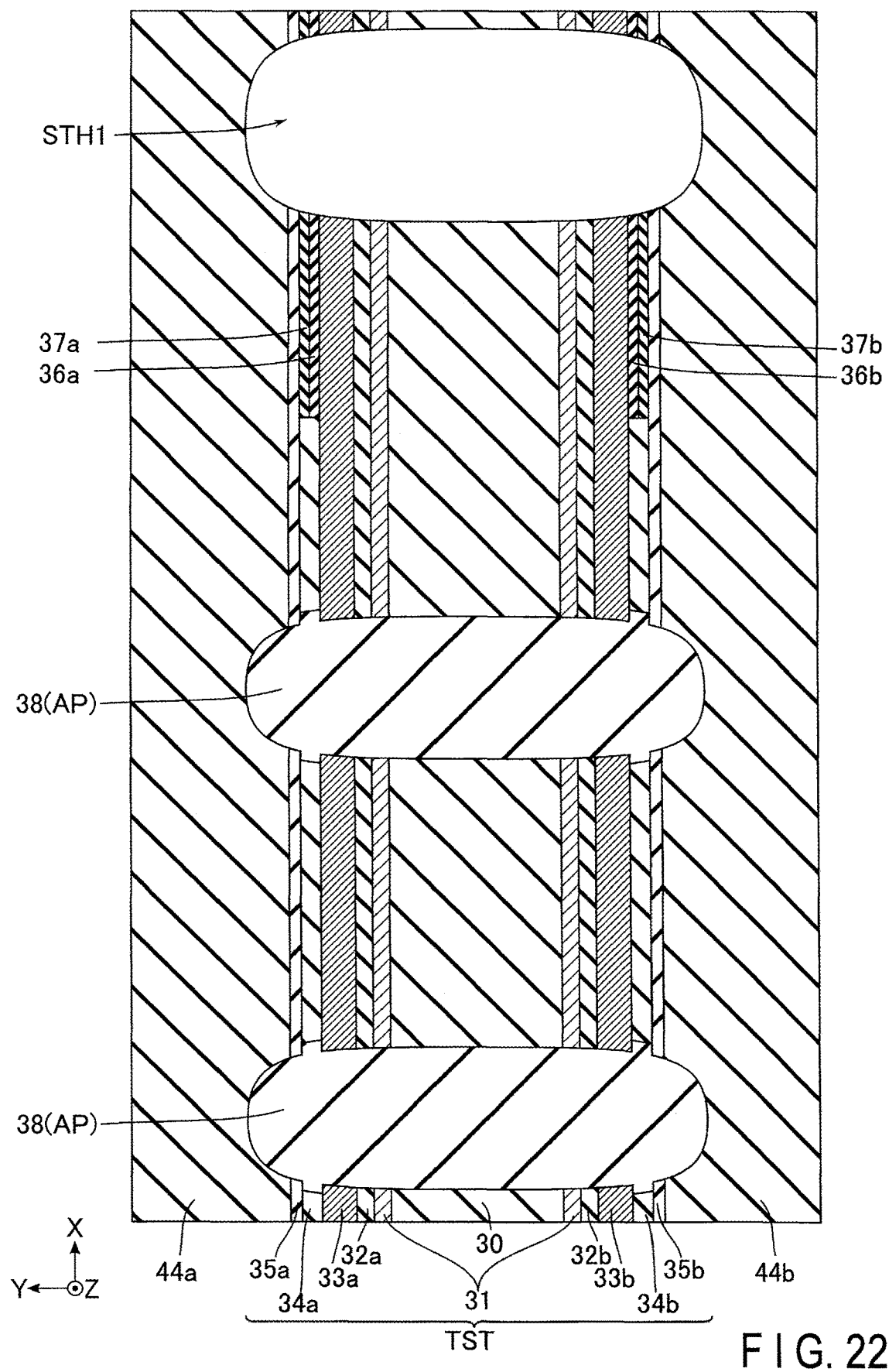
FIG. 22 is a transverse cross-sectional view of the memory cell array for explaining a step of manufacturing the memory device according to the first embodiment.

Next, as shown in FIG. 22, holes STH1 are formed in regions where the pillars STP1 are to be formed so as to separate the structure filling the trench MT in the X direction, and holes STH2 (not shown) are formed in regions where the pillars STP2 are to be formed. The sacrificial members 43, 44, and 45 are respectively separated into two portions of 43a and 43b, 44a and 44b, and 45a and 45b by the holes STH2. In the hole STH1, the sacrificial members 43a and 43b, 44a and 44b, and 45a and 45b are exposed. The etching in this step is anisotropic etching, such as RIE, in which all materials of the structure filling the trench MT are etched at a similar rate.

Figure 23:
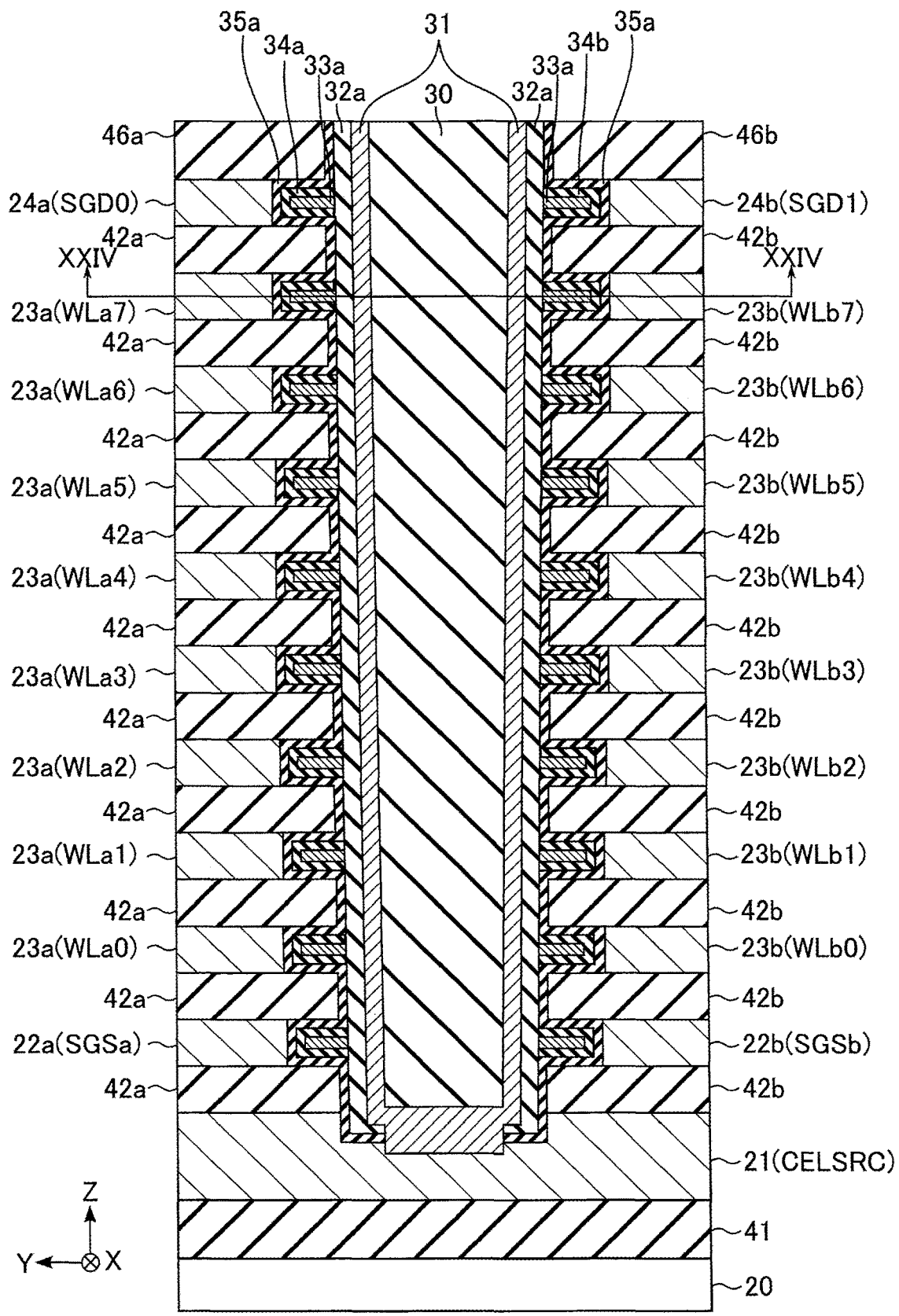
FIG. 23 is a vertical cross-sectional view of the memory cell array for explaining a step of manufacturing the memory device according to the first embodiment.

Next, as shown in FIG. 23, via the hole STH1, the sacrificial members 43a, 44a, and 45a are respectively replaced with the conductors 22a, 23a, and 24a, and the sacrificial members 43b, 44b, and 45b are respectively replaced with the conductors 22b, 23b, and 24b.

Figure 24:
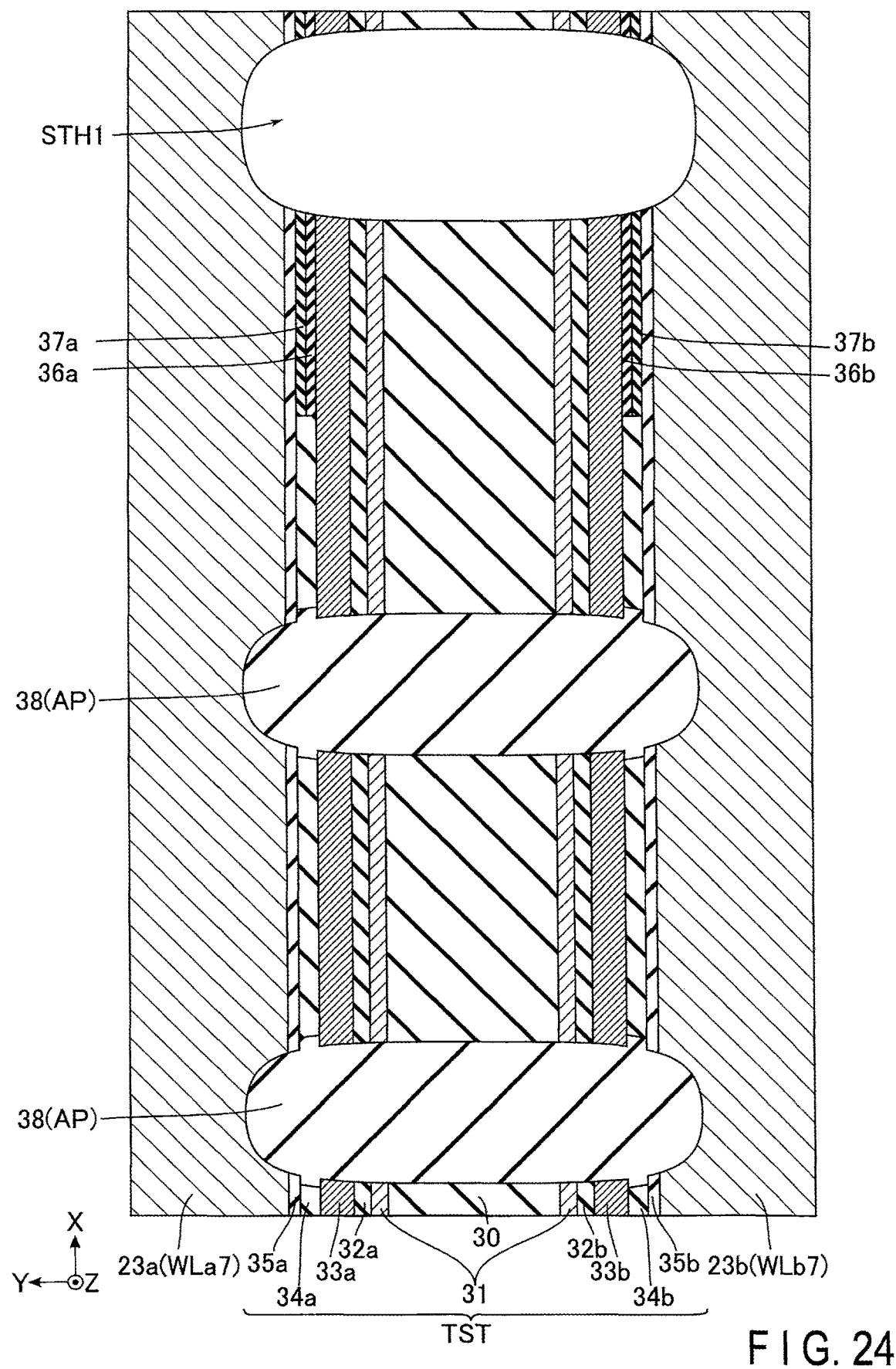
FIG. 24 is a transverse cross-sectional view of the memory cell array, taken along line XXIV-XXIV in FIG. 23.

FIG. 24 is a cross-sectional view of the memory cell array 10, taken along line XXIV-XXIV in FIG. 23. As shown in FIG. 24, through this step, the sacrificial members 43a, 44a, 45a, 43b, 44b, and 45b are selectively removed by either wet etching or dry etching via the hole STH1. Subsequently, the conductors 22a and 22b are respectively formed in the spaces from which the sacrificial members 43a and 43b have been removed, the conductors 23a and 23b are respectively formed in the spaces from which the sacrificial members 44a and 44b have been removed, and the conductors 25a and 25b are formed in the space from which the sacrificial members 45a and 45b have been removed.

Figure 25:
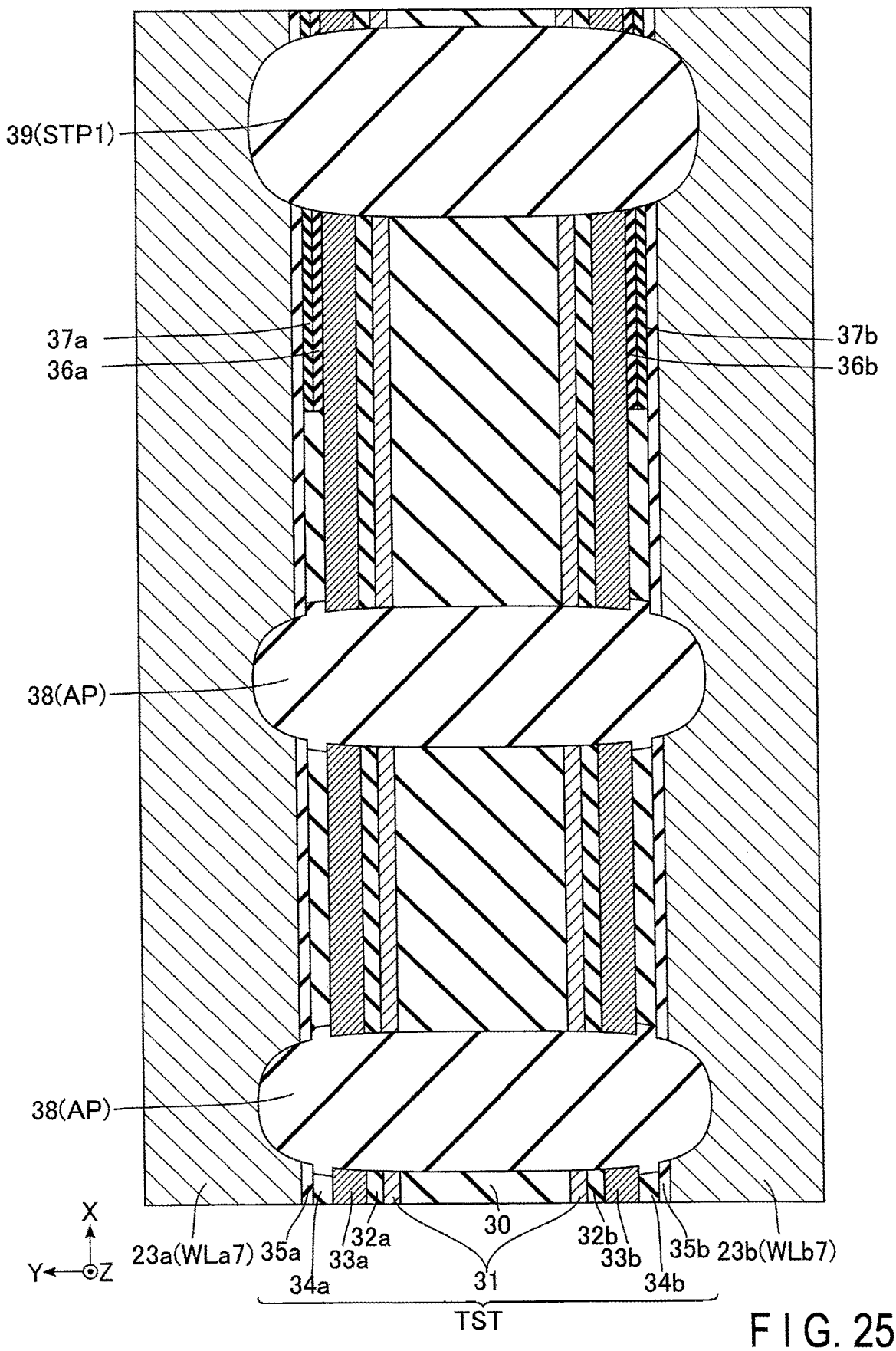
FIG. 25 is a transverse cross-sectional view of the memory cell array for explaining a step of manufacturing the memory device according to the first embodiment.

Next, after the hole STH1 is filled with the insulator 39 as shown in FIG. 25, the structure is flattened by CMP or the like, thereby removing the portion above the insulator 46.

Figure 26:
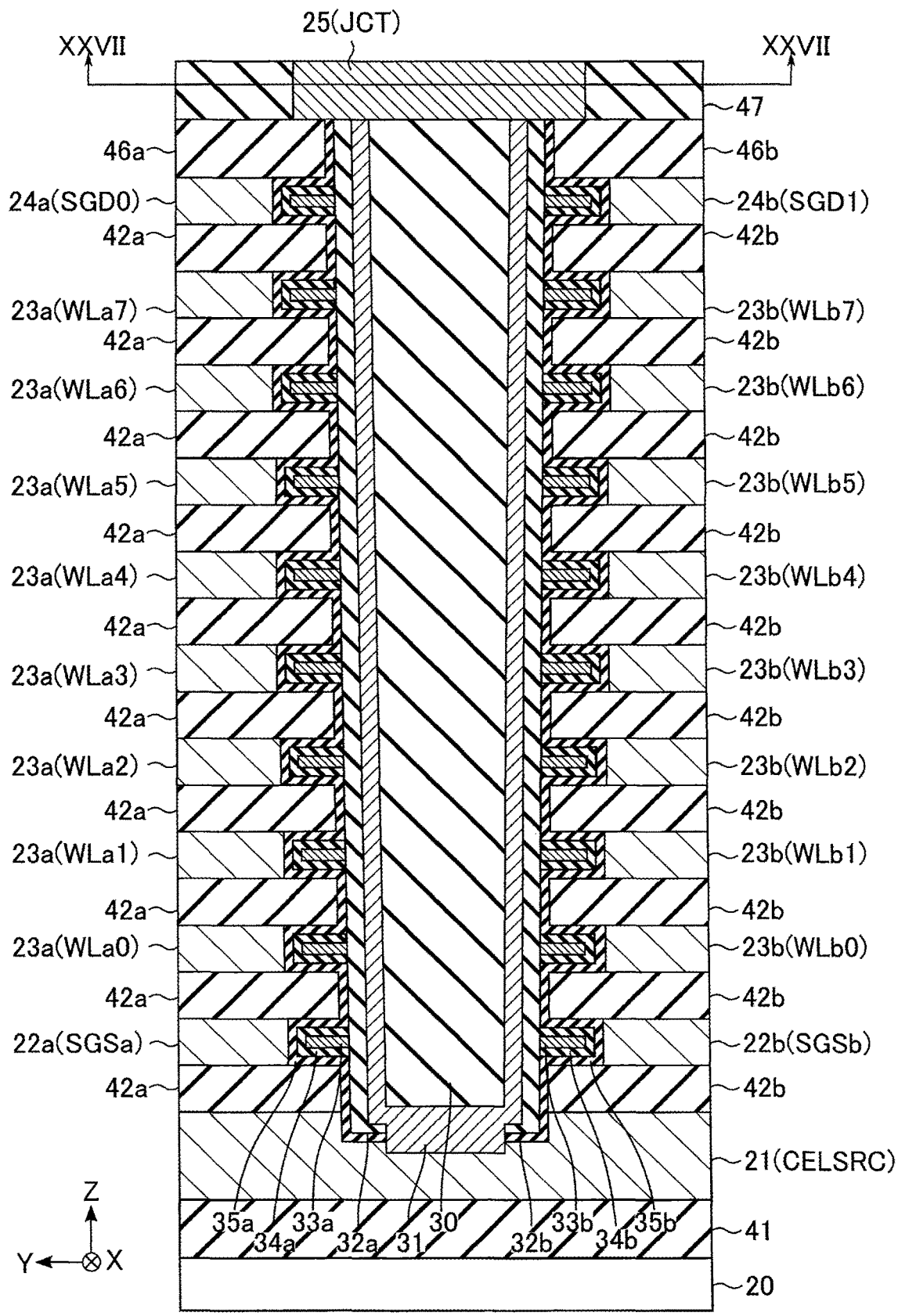
FIG. 26 is a vertical cross-sectional view of the memory cell array for explaining a step of manufacturing the memory device according to the first embodiment.

Next, as shown in FIG. 26, the semiconductor 25 is formed on a top surface of the structure filling the trench MT. Specifically, first, the insulator 47 is formed on the entire surface, and thereafter a mask in which regions corresponding to the semiconductor 25 are opened is formed by lithography. Then, a hole is formed in a region where the semiconductor 25 is to be formed by anisotropic etching using the formed mask, thereby exposing the semiconductor 31. The hole is filled with the semiconductor 25, so that the semiconductor 31 is electrically coupled to the semiconductor 25.

Figure 27:
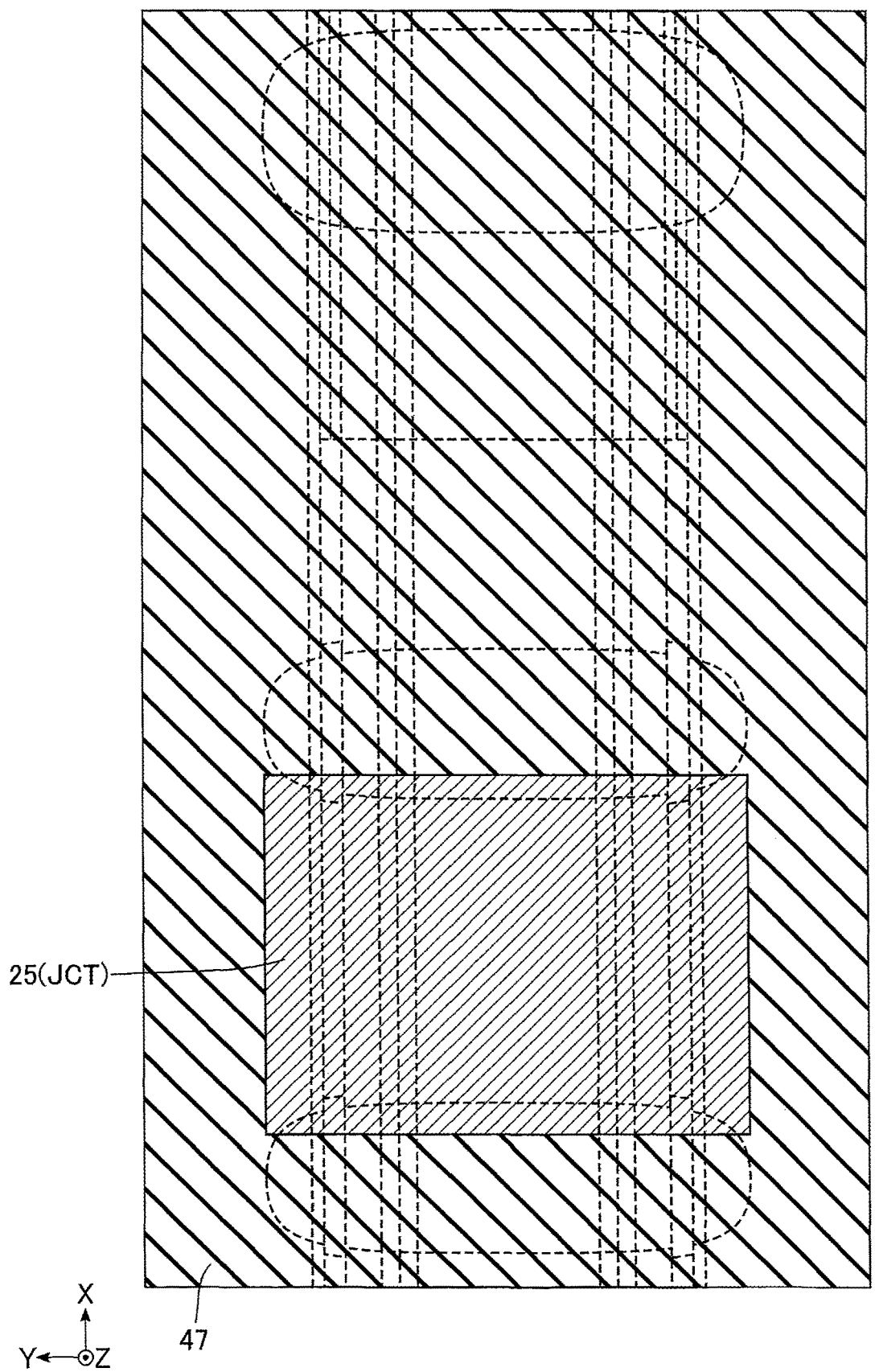
FIG. 27 is a transverse cross-sectional view of the memory cell array, taken along line XXVII-XXVII in FIG. 26.

FIG. 27 is a cross-sectional view of the memory cell array 10, taken along line XXVII-XXVII in FIG. 26. In FIG. 27, a cross-sectional structure of layers provided with, for example, the conductor 22a and 22b, 23a and 23b, or 24a and 24b of the portions below the semiconductor 25 is indicated with broken lines. As shown in FIG. 27, through this step, one semiconductor 25 covers two parts of the semiconductor 31 that are parallel to each other and extend in the X direction in a region sandwiched between the two pillars AP.

Through the steps described above, the memory strings MSa and MSb sandwiched between the two pillars AP are formed. Subsequently, through the step of forming the conductors 26 and 27 and the step of forming contacts coupled to the conductors 22a and 22b, 23a and 23b, and 24a and 24b, etc., the memory cell array 10 is formed.

The manufacturing steps described above are mere examples. Any process may be inserted between the manufacturing steps, or the manufacturing steps may be interchanged as long as no problem arises.

1.3 Advantageous Effects of Present Embodiment

According to the configurations of the first embodiment, the integration density can be improved while suppressing property degradation of the memory cells. This effect will be described below.

The memory structure MST includes two memory strings MSa and MSb coupled in parallel to the same bit line BL. Therefore, the integration density can be improved as compared to a case where one structure includes one memory string.

Furthermore, the memory structure MST is provided between two pillars AP in the trench structure TST. Accordingly, the part of the semiconductor 31 that corresponds to the memory string MSa and the part that corresponds to the memory string MSb are separated from each other. In other words, the semiconductor 31 has no coupling portion that couples the part corresponding to the memory string MSa and the part corresponding to the memory string MSb in the same layer (for example, the portion that couples the two parts of the semiconductor 31 separated from each other in the Y direction shown in FIG. 5). Therefore, it is possible to suppress generation of an electric field that may be generated from the word line WL and reach such a coupling portion of the semiconductor 31 via the charge storage films 33a and 33b, and thereby suppress erroneous reading.

Furthermore, the semiconductor 25 is formed on the top surface of the part corresponding to the memory string MSa of the semiconductor 31 and the top surface of the part corresponding to the memory string MSb of the semiconductor 31. Thus, one end of the memory string MSa and one end of the memory string MSb can be electrically coupled.

The memory cell transistor MCa includes the block insulating film 35a between the conductor 22a and the charge storage film 33a, and the block insulating film 34a between the block insulating film 35a and the charge storage film 33a. The memory cell transistor MCb includes the block insulating film 35b between the conductor 22b and the charge storage film 33b, and the block insulating film 34b between the block insulating film 35b and the charge storage film 33b. The block insulating films 34a and 34b have a dielectric constant higher than that of the block insulating films 35a and 35b. Thus, the properties of the gate insulating film in the memory cell transistor MC can be improved.

Since the block insulating films 34a and 34b include hafnium (Hf), zirconium (Zr) or the like, it is difficult to etch the films by the RIE used for forming holes AH and STH1. According to the first embodiment, when filling the trench MT, the sacrificial members 36a and 37a are provided in the region where the block insulating film 34a is to be formed, and the sacrificial members 36b and 37b are provided in the region where the block insulating film 34b is to be formed. The sacrificial members 36a and 36b include silicon oxide, and the sacrificial members 37a and 37b include silicon nitride. Accordingly, when the holes AH and STH1 are formed, the sacrificial members 36a, 37a, 36b, and 37b can be easily etched by RIE.

Furthermore, the charge storage films 33a respectively corresponding to the memory cell transistors MCa in the same memory string MS (for example, MSa) are physically separated from one another. Therefore, even if each of the charge storage films 33a has a floating gate structure including polysilicon or a metal, it is possible to suppress transfer of charges stored in the charge storage films 33a between the memory cell transistors MC. This results in improvement of the properties of the memory cell transistors MC.

Similarly, the block insulating films 34a respectively corresponding to the memory cell transistors MCa in the same memory string MS (for example, MSa) are physically separated from one another. Therefore, even if each of the block insulating films 34a has an electric charging property by hafnium (Hf) zirconium (Zr) included therein, it is possible to suppress transfer of charges stored in the block insulating films 34a between the memory cell transistors MC. This results in improved properties of the memory cell transistors MC.

Furthermore, the sacrificial members 36a and 37a and the sacrificial members 36b and 37b are removed by etching via the holes AH, and thereafter replaced with the block insulating films 34a and 34b, respectively. Thus, the block insulating films 34a and 34b can be formed in the memory structure MST without etching the block insulating films 34a and 34b by RIE.

Parts of the sacrificial members 36a, 37a, 36b, and 37b that are near a presumptive part where the hole STH1 is to be formed are not removed in the removing step described above but are maintained. Therefore, in the step of forming the hole STH1 subsequent to the removing step, it is possible to avoid etching of the block insulating films 34a and 34b, in the same manner as in the step of forming the holes AH. Accordingly, since the hole STH1 can be formed relatively easily, the load in the manufacturing steps can be reduced.

1.4 Modification

The first embodiment described above can be variously modified.

In the first embodiment described above, the charge storage films 33a and 33b and the semiconductor 31 are formed to have a uniform thickness in the X direction, for example. However, the embodiment is not limited to this example. For example, the charge storage films 33a and 33b and the semiconductor 31 may be formed to have a tapered shape that is gradually thinned from a central portion toward an end portion in the X direction. Hereinafter, the same configurations and manufacturing steps as those of the first embodiment will be omitted, and the configurations and manufacturing steps different from those of the first embodiment will be mainly described.

Figure 28:
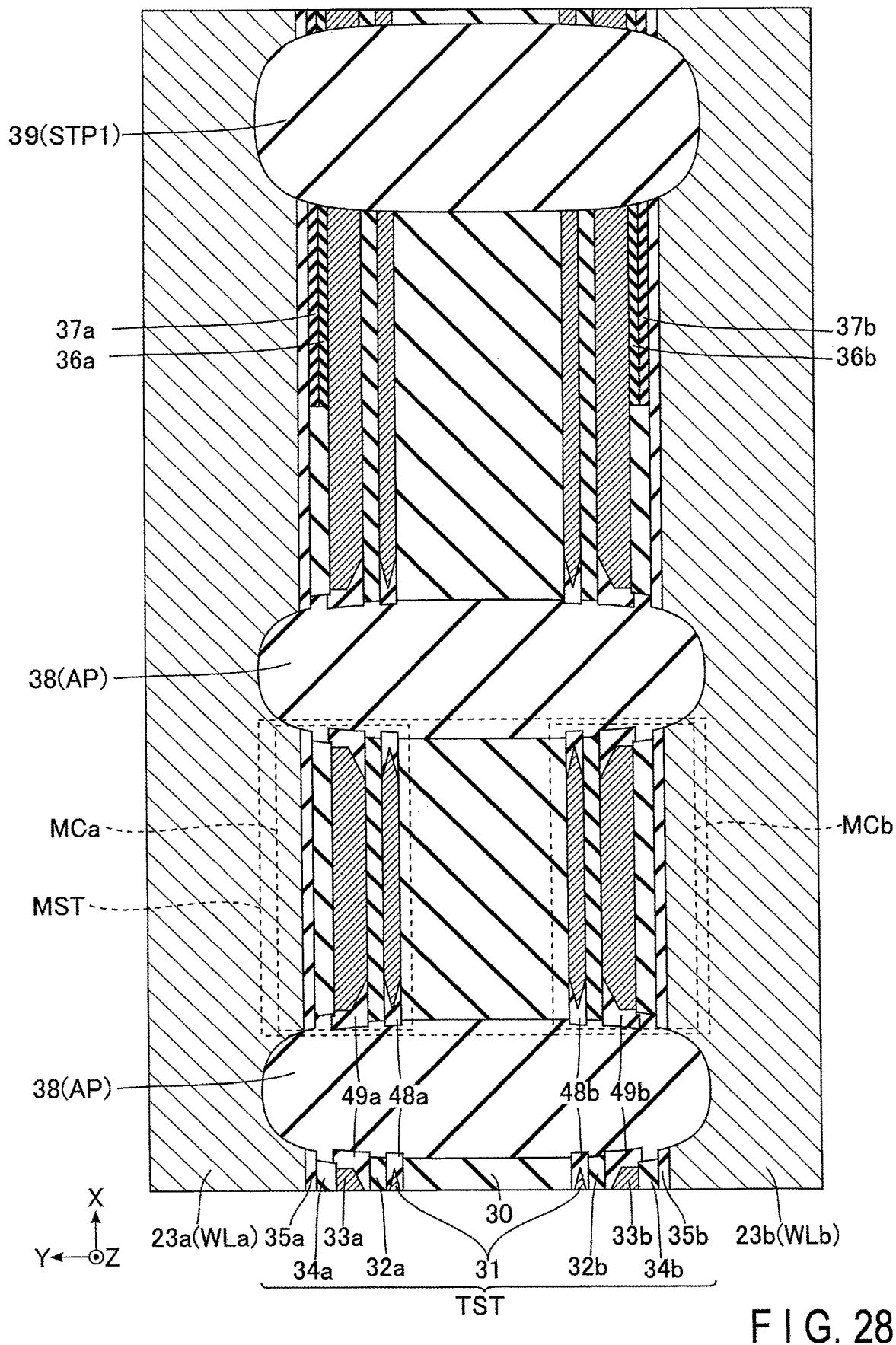
FIG. 28 is a transverse cross-sectional view of a memory cell array in a memory device according to a modification of the first embodiment.

First, a configuration of the trench structures of the memory device according to a modification of the first embodiment will be described with reference to a transverse cross-sectional view shown in FIG. 28. FIG. 28 corresponds to FIG. 5 used in the explanation of the first embodiment.

As shown in FIG. 28, an insulator 48a is formed between the part of the semiconductor 31 that corresponds to the memory cell transistor MCa and the insulator 38, and between the core member 30 and the tunnel insulating film 32a. An insulator 48b is formed between the part of the semiconductor 31 that corresponds to the memory cell transistor MCb and the insulator 38, and between the core member 30 and the tunnel insulating film 32b. An insulator 49a is formed between the charge storage film 33a and the insulator 38, and between the tunnel insulating film 32a and the block insulating film 34a. An insulator 49b is formed between the charge storage film 33b and the insulator 38, and between the tunnel insulating film 32b and the block insulating film 34b. Insulators 48a, 48b, 49a, and 49b include, for example, silicon oxide.

The insulator 48a includes, in an end portion of the semiconductor 31 in the X direction, a portion provided between the semiconductor 31 and the core member 30 and a portion provided between the semiconductor 31 and the tunnel insulating film 32a, and covers the end portion of the semiconductor 31 with those portions. The insulator 48b includes, in an end portion of the semiconductor 31 in the X direction, a portion provided between the semiconductor 31 and the core member 30 and a portion provided between the semiconductor 31 and the tunnel insulating film 32b, and covers the end portion of the semiconductor 31 with those portions. The thickness of the semiconductor 31 at an end portion covered with the insulator 48a or 48b is gradually reduced in a direction away from the central portion not covered with the insulator 48a or 48b. The semiconductor 31 is shorter in the X direction than the block insulating films 34a, 35a, 34b, and 35b.

The insulator 49a includes, in an end portion of the charge storage film 33a in the X direction, a portion provided between the charge storage film 33a and the tunnel insulating film 32a, and covers the end portion of the charge storage film 33a with that portion. The insulator 49b includes, in an end portion of the charge storage film 33b in the X direction, a portion provided between the charge storage film 33b and the tunnel insulating film 32b, and covers the end portion of the charge storage film 33b with that portion. The thickness of each of the charge storage films 33a and 33b at an end portion covered with the insulators 49a and 49b is gradually reduced in a direction away from the central portion not covered with the insulators 49a and 49b. The charge storage films 33a and 33b are respectively shorter in the X direction than the block insulating films 34a and 35a, and 34b and 35b.

Figure 29:
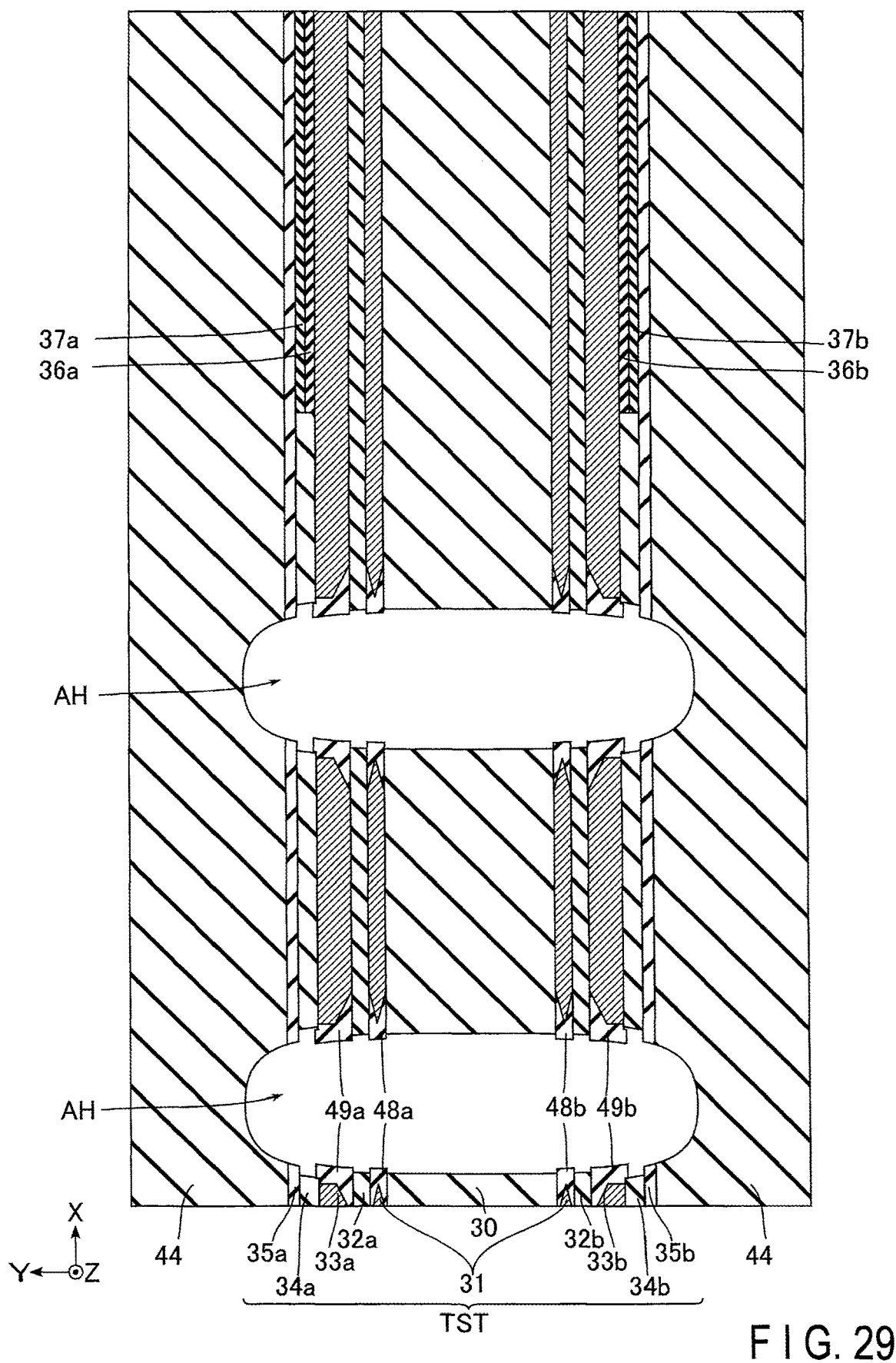
FIG. 29 is a transverse cross-sectional view of the memory cell array for explaining a step of manufacturing the memory device according to the modification of the first embodiment.

First, the manufacturing steps of the memory device according to the modification of the first embodiment will be described with reference to a transverse cross-sectional view shown in FIG. 29. FIG. 29 shows a step subsequent to the step of the first embodiment shown in FIG. 20.

First, the steps shown in FIG. 6 to FIG. 20 used for the first embodiment are executed.

Next, as shown in FIG. 29, the surfaces of the semiconductor 31 and the charge storage films 33a and 33b that are exposed via the holes AH are thermally oxidized. As a result, the exposed portion of the semiconductor 31 becomes the insulators 48a and 48b, and the exposed portions of the charge storage films 33a and 33b respectively become the insulators 49a and 49b. Since the semiconductor 31 is in contact with the core member 30 and the tunnel insulating films 32a and 32b, which include silicon oxide, it is oxidized relatively faster near the boundary with films including silicon oxide than in the other portions. Therefore, the semiconductor 31 has a tapered shape that is thinned toward an end portion. Since the charge storage films 33a and 33b are respectively in contact with the tunnel insulating films 32a and 32b, which include silicon oxide, they are oxidized relatively faster near the boundary with films including silicon oxide than in the other portions. Therefore, the charge storage films 33a and 33b have a tapered shape that is thinned toward an end portion.

Subsequently, the steps similar to those of the first embodiment shown in FIG. 21 to FIG. 27 are executed, thereby forming a trench structure TST.

According to the modification of the first embodiment, the semiconductor 31 is oxidized at an end portion along the X direction. As a result, the semiconductor 31 is gradually thinned toward the end portion, and the length in the X direction is shorter than the block insulating films 34a, 35a, 34b, and 35b. Therefore, the gate controllability of the memory cell transistor MC can be improved. Accordingly, property degradation of the memory cell transistors MC can be suppressed.

2. Second Embodiment

Next, a memory device according to the second embodiment will be described. The second embodiment differs from the first embodiment in that, before the holes AH are filled, the exposed portions of the semiconductor 31 and the charge storage films 33a and 33b are partially removed and receded in the X direction. Hereinafter, the same configurations and manufacturing method as those of the first embodiment will be omitted, and the configurations and manufacturing method different from those of the first embodiment will be mainly described.

2.1 Trench Structure

Figure 30:
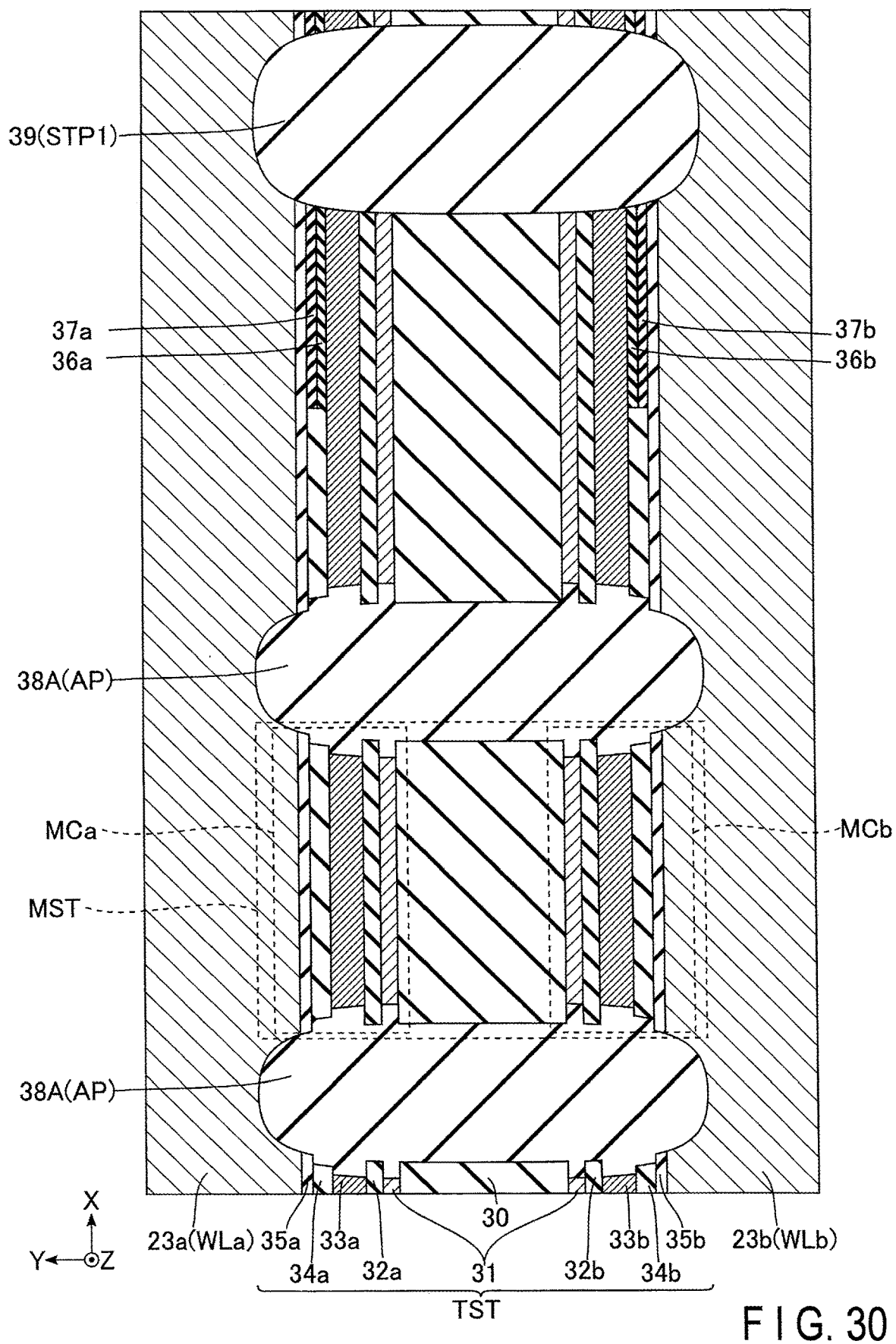
FIG. 30 is a transverse cross-sectional view of a memory cell array in a memory device according to a second embodiment.

FIG. 30 is a cross-sectional view for explaining a configuration of the trench structure of the memory device according to the second embodiment, and corresponds to FIG. 4 used in the explanation of the first embodiment.

As shown in FIG. 30, the memory structure MST is formed between two insulators 38A each functioning as a pillar AP. The insulator 38A is longer in the X direction at portions in contact with the semiconductor 31 and the charge storage films 33a and 33b than at portions in contact with the core member 30, the tunnel insulating films 32a and 32b, the block insulating films 34a and 34b, and the block insulating films 35a and 35b. In other words, the semiconductor 31 and the charge storage films 33a and 33b are shorter in the X direction than the block insulating films 34a, 35a, 34b, and 35b.

2.2 Method of Manufacturing Memory Device

Figure 31:
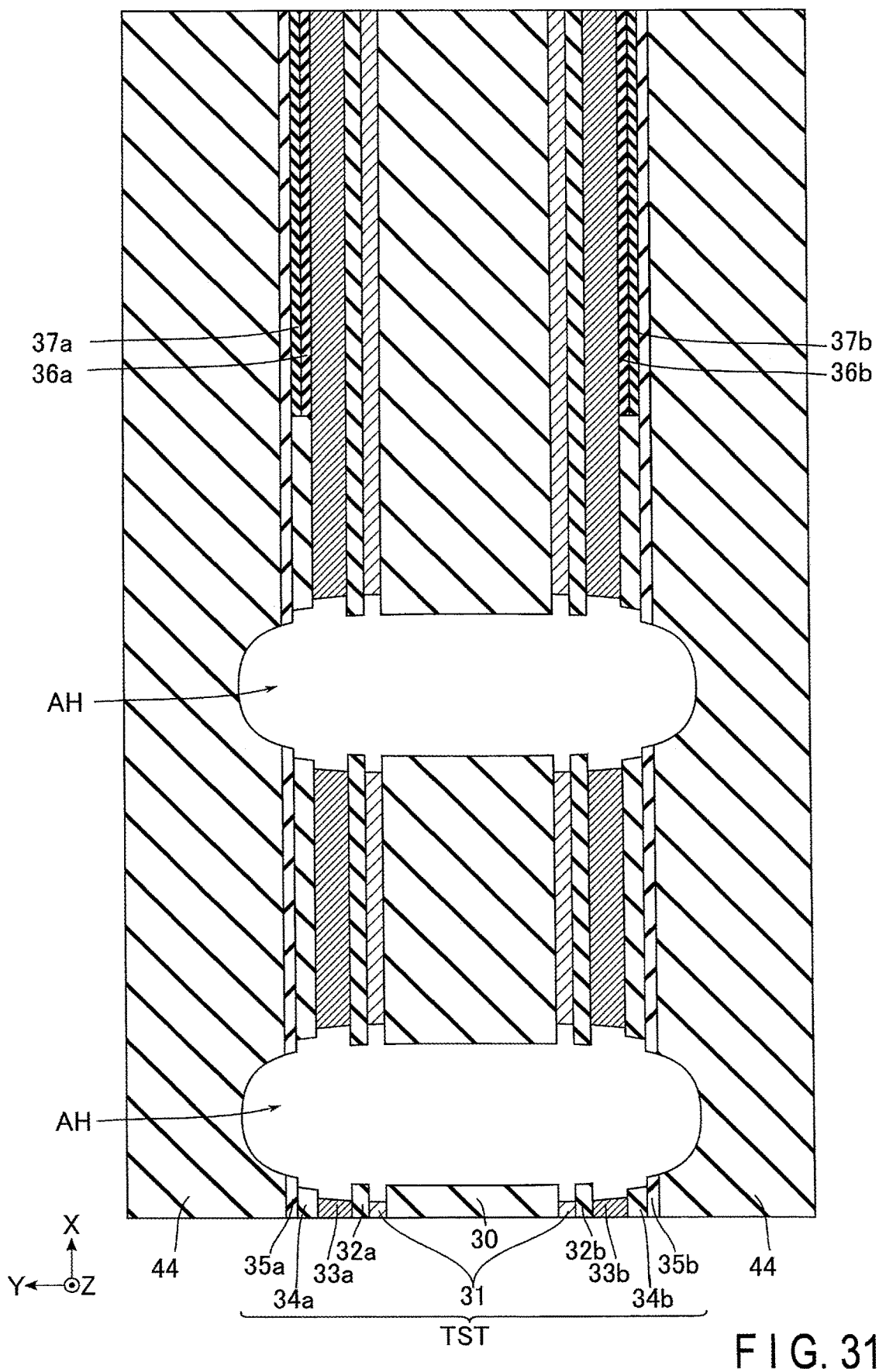
FIG. 31 is a transverse cross-sectional view of the memory cell array for explaining a step of manufacturing the memory device according to the second embodiment.

FIG. 31 is a transverse cross-sectional view for explaining a step of manufacturing the memory device of the second embodiment. FIG. 31 shows a step subsequent to the step of the first embodiment shown in FIG. 20.

First, the steps shown in FIG. 6 to FIG. 20 used for the first embodiment are executed.

Next, as shown in FIG. 31, exposed portions of the semiconductor 31 and the charge storage films 33a and 33b are selectively removed by wet etching via the holes AH. As a result, the end portions in the X direction of the semiconductor 31 and the charge storage films 33a and 33b are receded from the end portions in the X direction of the block insulating films 34a, 34b, 35a, and 35b.

Subsequently, the steps similar to those of the first embodiment shown in FIG. 21 to FIG. 27 are executed, Thereby Forming a Trench Structure TST.

2.3 Advantageous Effect of Present Embodiment

According to the second embodiment, the end portions in the X direction of the semiconductor 31 and the charge storage films 33a and 33b are selectively removed. As a result, the lengths of the semiconductor 31 and the charge storage films 33a and 33b are shorter in the X direction than the block insulating films 34a, 35a, 34b, and 35b. Therefore, the gate controllability of the memory cell transistor MC can be improved. Accordingly, property degradation of the memory cell transistors MC can be suppressed.

2.4 Modification

Configurations similar to those of the modification of the first embodiment are applicable to the second embodiment. In the second embodiment, the charge storage films 33a and 33b and the semiconductor 31 may be formed to have a tapered shape that is gradually thinned from a central portion toward an end portion in the X direction.

Figure 32:
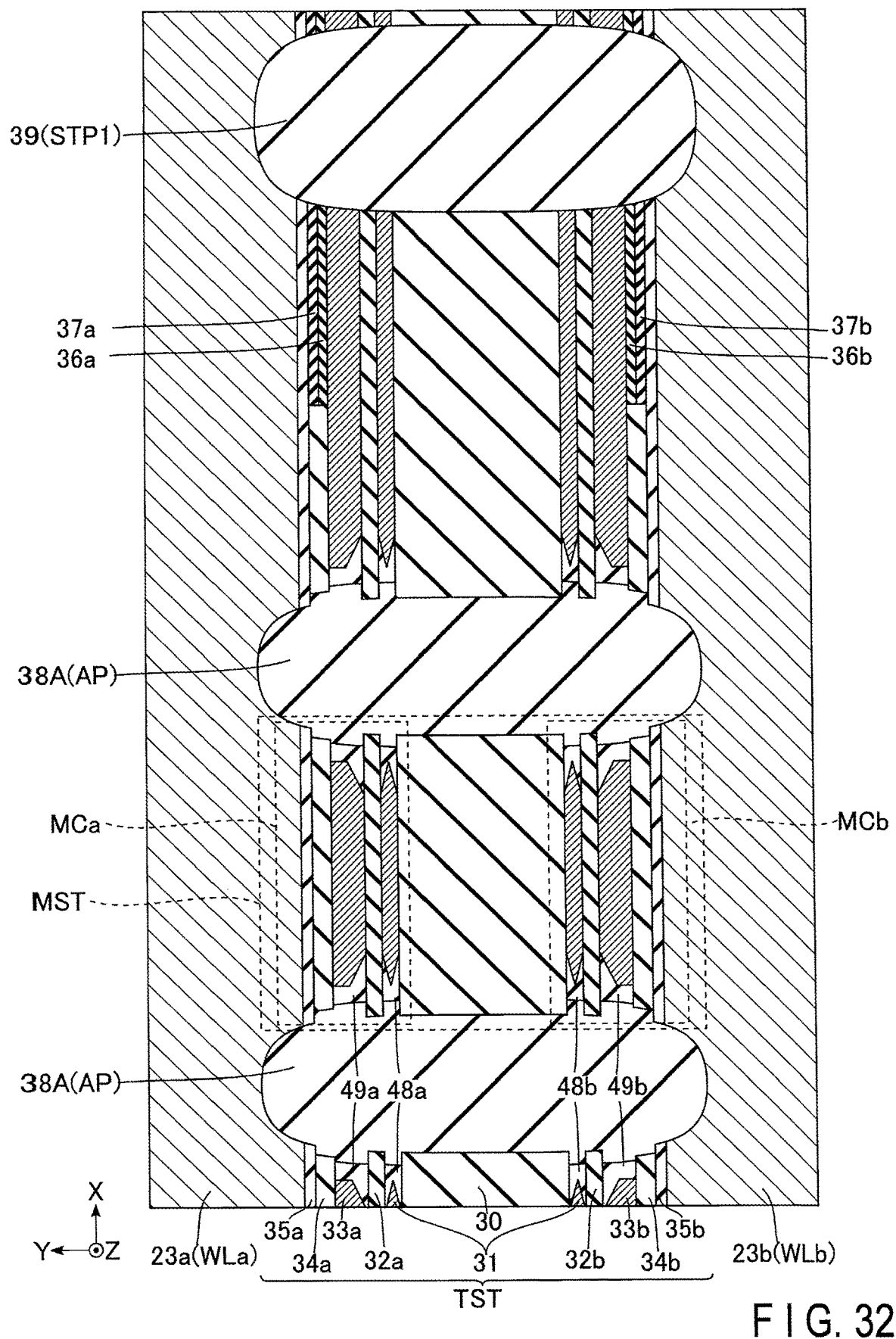
FIG. 32 is a transverse cross-sectional view of a memory cell array according to a modification of the second embodiment.

FIG. 32 is a cross-sectional view for explaining a configuration of the trench structure of the memory device according to the modification of the second embodiment, and corresponds to FIG. 28 used in the explanation of the modification of the first embodiment.

As shown in FIG. 32, an insulator 48a is formed between the part of the semiconductor 31 that corresponds to the memory cell transistor MCa and the insulator 38A, and between the core member 30 and the tunnel insulating film 32a. An insulator 48b is formed between the part of the semiconductor 31 that corresponds to the memory cell transistor MCb and the insulator 38A, and between the core member 30 and the tunnel insulating film 32b. An insulator 49a is formed between the charge storage film 33a and the insulator 38A, and between the tunnel insulating film 32a and the block insulating film 34a. An insulator 49b is formed between the charge storage film 33b and the insulator 38A, and between the tunnel insulating film 32b and the block insulating film 34b. Since the configurations of the insulators 48a, 48b, 49a, and 49b are the same as those in the modification of the first embodiment, description thereof is omitted.

According to the modification of the second embodiment, the end portions in the X direction of the semiconductor 31 and the charge storage films 33a and 33b are partially removed by etching that allows polysilicon to be selectively removed, and thereafter oxidized. As a result, the semiconductor 31 is etched until the length in the X direction becomes shorter than the block insulating films 34a, 35a, 34b, and 35b and thereafter gradually thinned toward the end portions. Therefore, the gate controllability of the memory cell transistor MC can be further improved.

3. Third Embodiment

Next, a memory device according to the third embodiment will be described. The third embodiment differs from the second embodiment in that, when removing the exposed portions of the semiconductor 31 and the charge storage films 33a and 33b in the X direction, the semiconductor 31 has a greater amount removed than the charge storage films 33a and 33b. Hereinafter, the same configurations and manufacturing method as those of the second embodiment will be omitted, and the configurations and manufacturing method different from those of the second embodiment will be mainly described.

3.1 Trench Structure

Figure 33:
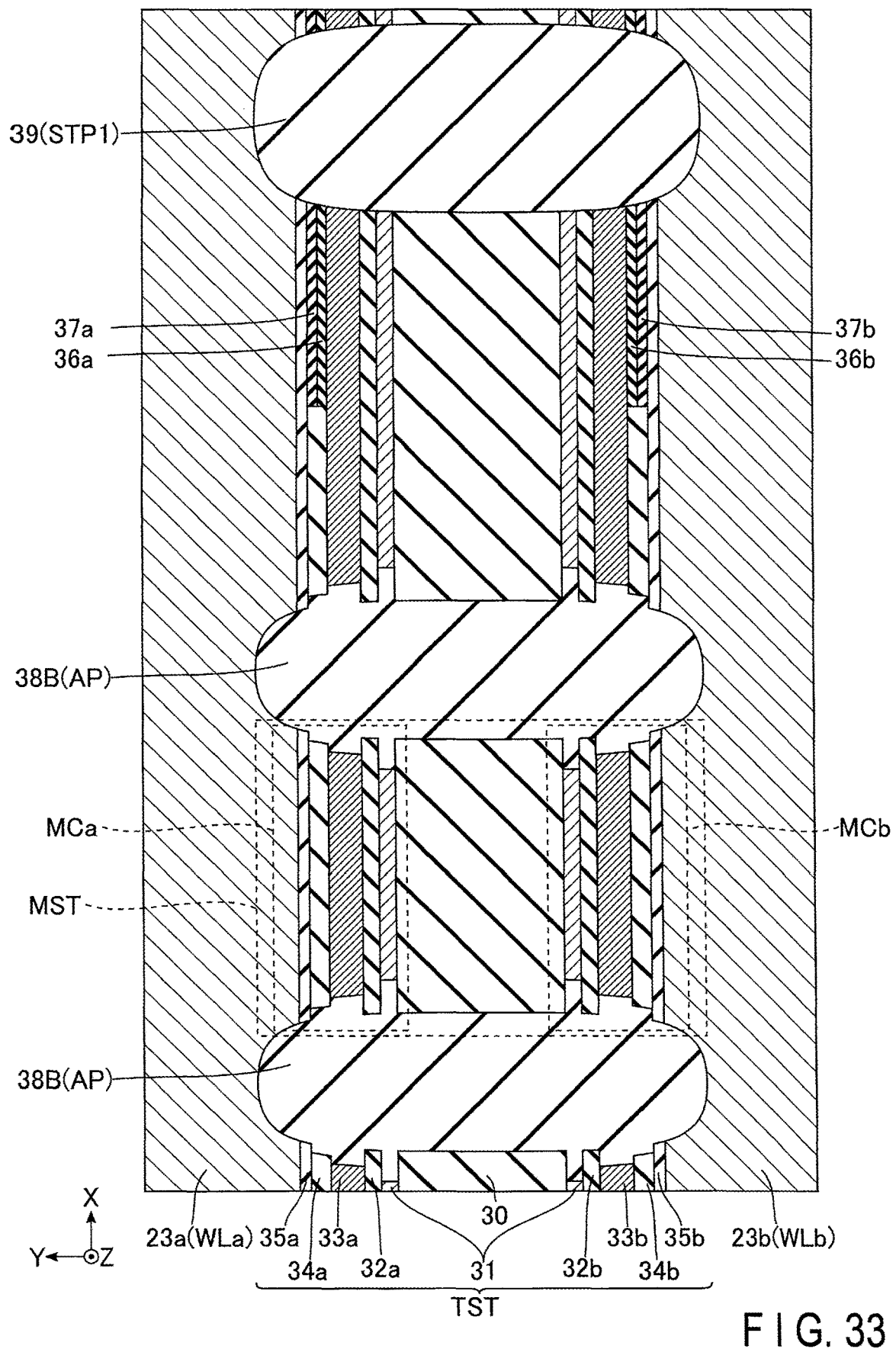
FIG. 33 is a transverse cross-sectional view of a memory cell array in a memory device according to a third embodiment.

FIG. 33 is a cross-sectional view for explaining a configuration of the trench structure of the memory device according to the third embodiment, and corresponds to FIG. used in the explanation of the second embodiment.

As shown in FIG. 33, the memory structure MST is formed between two insulators 38B each functioning as a pillar AP. The insulator 38B is longer in the X direction at portions in contact with the charge storage films 33a and 33b than at portions in contact with the core member 30, the tunnel insulating films 32a and 32b, the block insulating films 34a and 34b, and the block insulating films 35a and 35b. The insulator 38B is longer in the X direction at portions in contact with the semiconductor 31 than at portions in contact with the charge storage films 33a and 33b. In other words, the charge storage films 33a and 33b are shorter in the X direction than the block insulating films 34a, 35a, and 34b, and 35b, and the semiconductor 31 is shorter in the X direction than the charge storage films 33a and 33b.

3.2 Method of Manufacturing Memory Device

Figure 34:
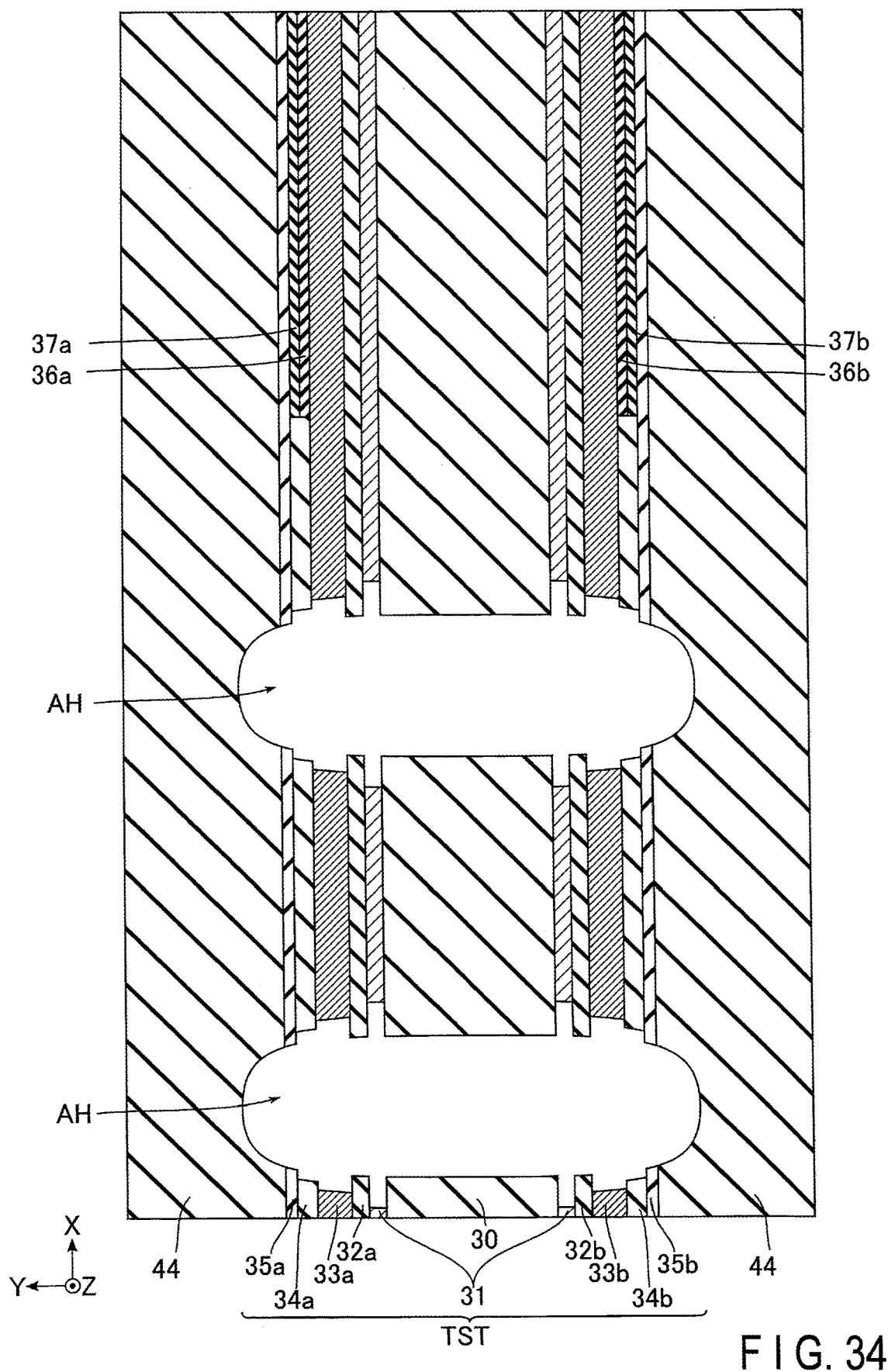
FIG. 34 is a transverse cross-sectional view of the memory cell array for explaining a step of manufacturing the memory device according to the third embodiment.

FIG. 34 is a transverse cross-sectional view for explaining a step of manufacturing the memory device of the third embodiment. FIG. 34 shows a step subsequent to the step of the second embodiment shown in FIG. 31.

First, the steps shown in FIG. 6 to FIG. 20 used for the first embodiment are executed.

Next, as shown in FIG. 34, exposed portions of the semiconductor 31 and the charge storage films 33a and 33b are selectively removed by wet etching via the holes AH. As a result, the end portions in the X direction of the semiconductor 31 and the charge storage films 33a and 33b are receded from the end portions in the X direction of the block insulating films 34a, 34b, 35a, and 35b.

In the third embodiment, the charge storage films 33a and 33b further include boron or carbon (C) in addition to polysilicon. This can be realized by, for example, diffusing boron included in the sacrificial members 36a and 36b respectively into the charge storage films 33a and 33b.

The method to allow the charge storage films 33a and 33b to further include boron or carbon (C) is not limited to the above example. For example, when the charge storage film 33 is formed in the step shown in FIG. 11 used in the explanation of the first embodiment, a film doped with boron or carbon may be formed. Alternatively, for example, when the charge storage films 33a and 33b in each layer are exposed in the trench MT in the step shown in FIG. 12 used in the explanation of the first embodiment, the charge storage films 33a and 33b may be doped with boron or carbon by vapor-phase diffusion.

Accordingly, in the step of selectively etching polysilicon, the etching rate of the charge storage films 33a and 33b is lower than the etching rate of the semiconductor 31. Therefore, in the step shown in FIG. 34, the end portions in the X direction of the semiconductor 31 are receded from the end portions in the X direction of the charge storage films 33a and 33b.

Subsequently, the steps similar to those of the first embodiment shown in FIG. 21 to FIG. 27 are executed, thereby forming a trench structure TST.

3.3 Advantageous Effects of Present Embodiment

According to the third embodiment, the end portions in the X direction of the semiconductor 31 and the charge storage films 33a and 33b are selectively removed. As a result, the lengths of the semiconductor 31 and the charge storage films 33a and 33b are shorter in the X direction than the block insulating films 34a, 35a, 34b, and 35b. Also, the semiconductor 31 is shorter in the X direction than the charge storage films 33a and 33b. Therefore, the gate controllability of the memory cell transistor MC can be improved. Accordingly, property degradation of the memory cell transistors MC can be suppressed.

3.4 Modification

Figure 35:
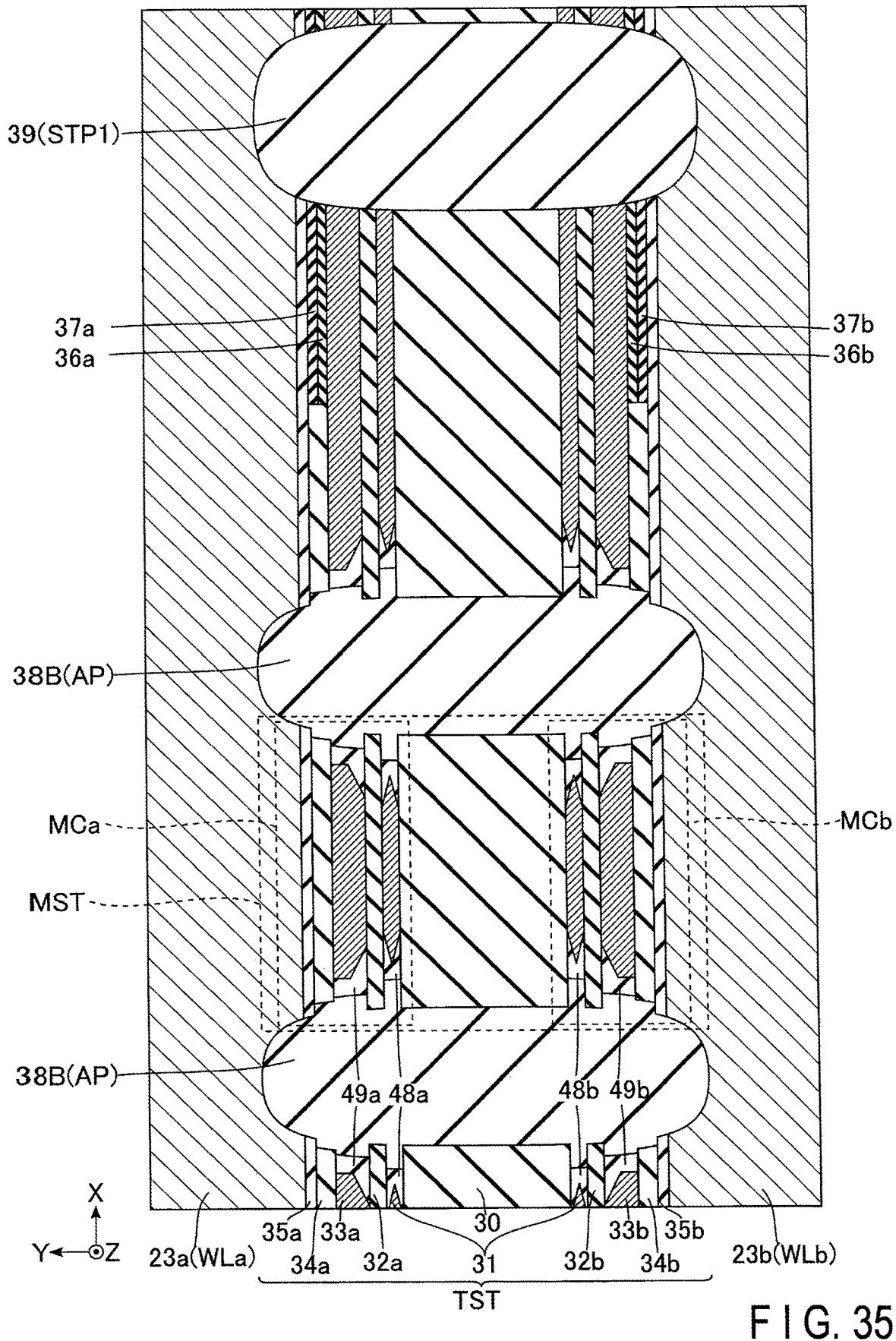
FIG. 35 is a transverse cross-sectional view of a memory cell array according to a modification of the third embodiment.

Configurations similar to those of the modification of the first embodiment and the modification of the second embodiment are applicable to the third embodiment. Specifically, in the third embodiment, the charge storage films 33a and 33b and the semiconductor 31 may be formed to have a tapered shape that is gradually thinned from a central portion toward an end portion in the X direction. FIG. 35 is a cross-sectional view for explaining a configuration of the trench structure of the memory device according to the modification of the third embodiment, and corresponds to FIG. 28 used in the explanation of the modification of the first embodiment.

As shown in FIG. 35, an insulator 48a is formed between the part of the semiconductor 31 that corresponds to the memory cell transistor MCa and the insulator 38B, and between the core member 30 and the tunnel insulating film 32a. An insulator 48b is formed between the part of the semiconductor 31 that corresponds to the memory cell transistor MCb and the insulator 38B, and between the core member 30 and the tunnel insulating film 32b. An insulator 49a is formed between the charge storage film 33a and the insulator 38B, and between the tunnel insulating film 32a and the block insulating film 34a. An insulator 49b is formed between the charge storage film 33b and the insulator 38B, and between the tunnel insulating film 32b and the block insulating film 34b. Since the configurations of the insulators 48a, 48b, 49a, and 49b are the same as those in the modification of the first embodiment, description thereof is omitted.

According to the modification of the third embodiment, the end portions in the X direction of the semiconductor 31 and the charge storage films 33a and 33b are partially removed by etching that allows polysilicon to be selectively removed, and thereafter oxidized. As a result, the charge storage films 33a and 33b are shorter in the X direction than the block insulating films 34a, 35a, 34b, and 35b, and the semiconductor 31 is shorter in the X direction than the charge storage films 33a and 33b. Furthermore, the semiconductor 31 and the charge storage films 33a and 33b are gradually thinned toward the end portions. Therefore, the gate controllability of the memory cell transistor MC can be further improved.

4. Fourth Embodiment

Next, a memory device according to the fourth embodiment will be described. The fourth embodiment differs from the first to third embodiments in that, before the holes AH are filled, the exposed portions of the sacrificial members 43, 44, and 45 are partially removed and receded. Hereinafter, the same configurations and manufacturing method as those of the first embodiment will be omitted, and the configurations and manufacturing method different from those of the first embodiment will be mainly described.

4.1 Trench Structure

Figure 36:
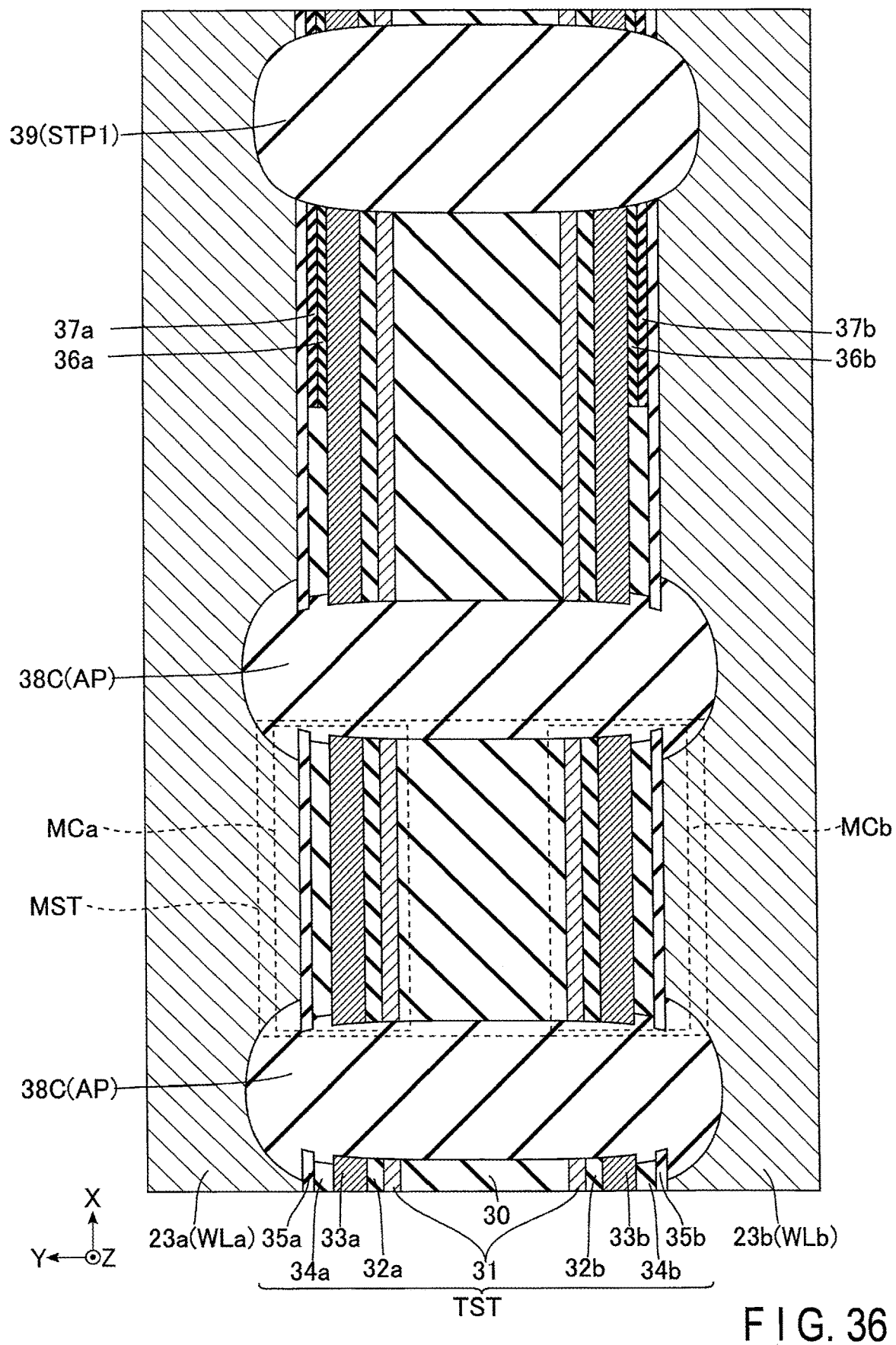
FIG. 36 is a transverse cross-sectional view of the memory cell array in a memory device according to a fourth embodiment.

FIG. 36 is a cross-sectional view for explaining a configuration of the trench structure of the memory device according to the fourth embodiment, and corresponds to FIG. 4 used in the explanation of the first embodiment.

As shown in FIG. 36, the trench structure TST is separated by insulators 38C each functioning as a pillar AP. The memory structure MST is formed in a portion of the trench structure TST sandwiched between two insulators 38C adjacent to each other in the X direction.

A portion of the conductor 23a sandwiched along the X direction between the two insulators 38C is shorter in the X direction than the charge storage film 33a. A portion of the conductor 23b sandwiched along the X direction between the two insulators 38C is shorter in the X direction than the charge storage film 33b.

4.2 Method of Manufacturing Memory Device

Figure 37:
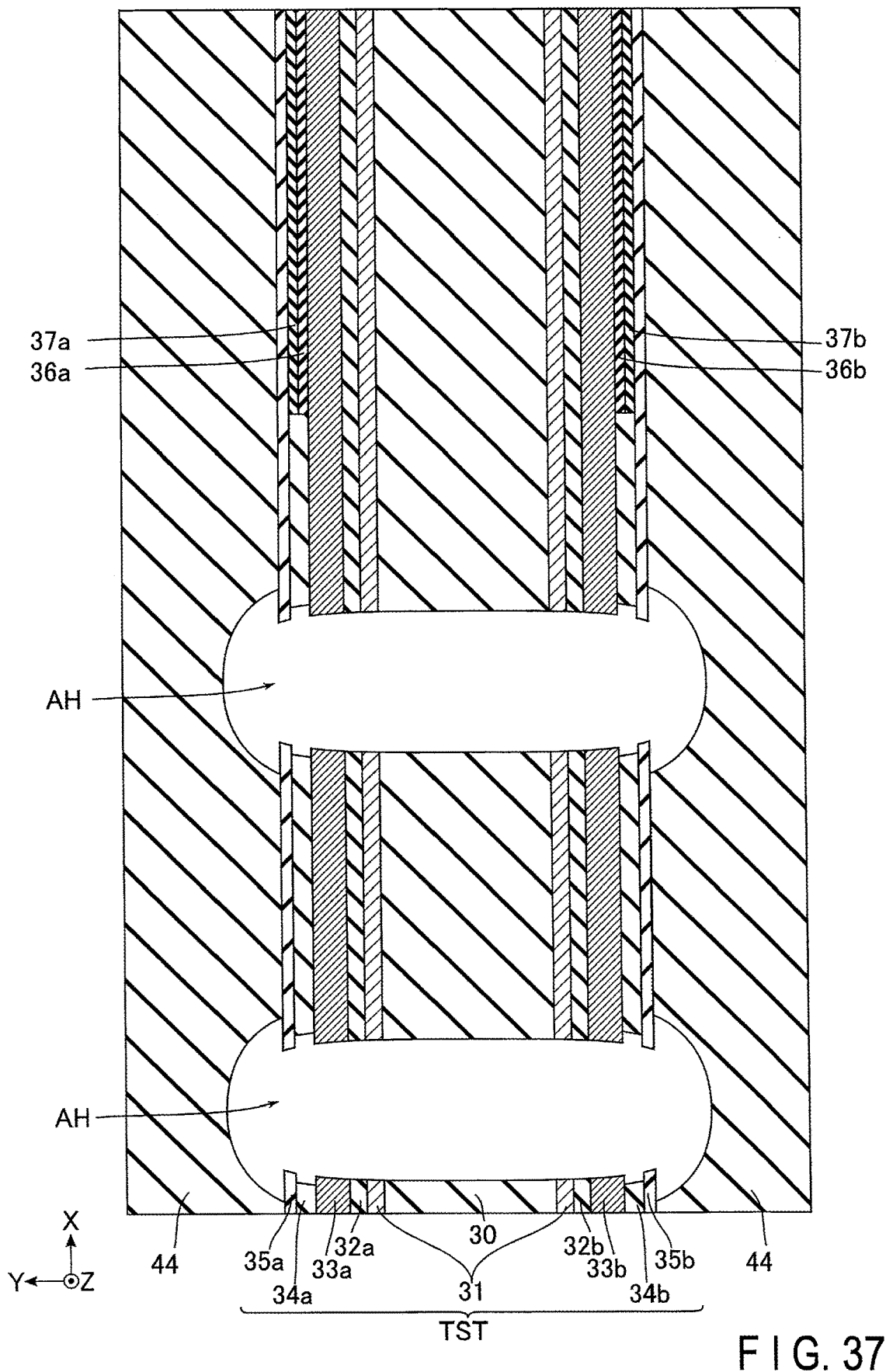
FIG. 37 is a transverse cross-sectional view of the memory cell array for explaining a step of manufacturing the memory device according to the fourth embodiment.

FIG. 37 is a transverse cross-sectional view for explaining a step of manufacturing the memory device of the fourth embodiment. FIG. 37 shows a step subsequent to the step of the first embodiment shown in FIG. 20.

First, the steps shown in FIG. 6 to FIG. 20 used in the explanation of the first embodiment are executed.

Next, as shown in FIG. 37, the sacrificial members 43, 44, and 45 to be exposed are selectively removed by wet etching via the holes AH. Accordingly, the parts of the sacrificial members 43, 44, and 45 that are exposed in the holes AH are isotropically removed in the XY plane. As a result, the parts of the sacrificial members 43, 44, and 45 sandwiched along the X direction between two holes AH that are adjacent along the X direction are shorter in the X direction than the charge storage films 33a and 33b.

Subsequently, the steps similar to those of the first embodiment shown in FIG. 21 to FIG. 27 are executed, thereby forming a trench structure TST.

4.3 Advantageous Effect of Present Embodiment

According to the fourth embodiment, the sacrificial members 43, 44, and 45 are replaced with the insulator 38 via the holes AH, before they are respectively replaced with the conductors 23, 24, and 25 via the hole STH1. The portions that are replaced with the insulator 38C are not replaced with the conductors 23, 24, and 25 even through the step of replacing the sacrificial members 43, 44, and with the conductors 23, 24, and 25 via the hole STH1. Accordingly, the portion sandwiched between the insulators 38C of each of the conductors 23, 24, and 25 is shorter in the X direction than the charge storage films 33a and 33c. Therefore, the gate controllability of the memory cell transistor MC can be improved. Accordingly, property degradation of the memory cell transistors MC can be suppressed.

5. Others

The first to fourth embodiments described above can be modified in various manners.

For example, in the description of the fourth embodiment, the example of the charge storage films 33a and 33b and the semiconductor 31 being formed to have a uniform thickness in the X direction is described; however, the embodiments are not limited thereto. As in the modification of the first embodiment, the end portions may be formed to have a tapered shape in which thicknesses are gradually reduced toward the end portions thereof.

Furthermore, in the description of the fourth embodiment, the example of the charge storage films 33a and 33b and the semiconductor 31 being the same in length in the X direction as the block insulating films 34a, 35a, 34b, and 35b is described; however, the embodiments are not limited thereto. For example, as in the second embodiment, the charge storage films 33a and 33b and the semiconductor 31 may be formed to be shorter in the X direction than the block insulating films 34a, 35a, 34b, and 35b. Furthermore, as in the third embodiment, the semiconductor 31 may be formed to be shorter in the X direction than the charge storage films 33a and 33b.

Moreover, in the description of the first to fourth embodiments, the example of the block insulating films 35a and 35b being formed as continuous films in the memory strings MSa and MSb respectively is described; however, the embodiments are not limited thereto. For example, the block insulating film 35a may be separately provided for each of the memory cell transistors MCa in the memory string MSa, and the block insulating film 35b may be separately provided for each of the memory cell transistors MCb in the memory string MSb. In this case, for example, after recesses are formed in the layers in which the sacrificial members 43, 44, and 45 are formed in the step shown in FIG. 9, the block insulating film 35 is formed over all to fill the recesses. Thereafter, the block insulating film 35 is selectively removed to expose the side surfaces of the insulators 42 and 46 in the trench MT. As a result, the block insulating films 35a and 35b can be left in the recesses to have a predetermined thickness in the Y direction from the side surfaces of the sacrificial members 43, 44, and 45.

Furthermore, in the description of the first to fourth embodiments, the example of forming the layer stack including the sacrificial members 43 to 45 and thereafter replacing these members with the conductors 22 to 24 is described; however, the embodiments are not limited thereto. For example, the layer stack may be formed to further include the conductors 22 to 24. In this case, the step of replacing the sacrificial members with the conductors can be omitted, and the step of forming the pillar STP1 can also be omitted. When the conductors 22 to 24 are stacked in advance, the conductors 22 to 24 may have a configuration including polysilicon to promote etching when forming the trench MT and the like.

While certain embodiments have been described, these embodiments have been presented by way of example only, and are not intended to limit the scope of the inventions. Indeed, the embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit.

What is claimed is:

1. A memory device comprising:
   a first conductor included in a first layer stack that is stacked in a first direction;
   a second conductor included in a second layer stack that is stacked in the first direction and included in a layer that includes the first conductor, the second layer stack being separated from the first layer stack;
   a first semiconductor between the first layer stack and the second layer stack, the first semiconductor including:
      a first portion and a second portion, each extending in the first direction, and being separated from each other in same layer; and
      a third portion electrically coupling the first portion and the second portion below the first conductor and the second conductor;
   a first charge storage film between the first conductor and the first portion of the first semiconductor;
   a second charge storage film between the second conductor and the second portion of the first semiconductor;
   a first insulator between the first conductor and the first charge storage film;
   a second insulator between the second conductor and the second charge storage film;
   a third insulator between the first insulator and the first charge storage film; and
   a fourth insulator between the second insulator and the second charge storage film,
   wherein
   the third insulator and the fourth insulator have a dielectric constant higher than that of the first insulator and the second insulator,
   the first layer stack, the first insulator, the third insulator, the first charge storage film, the first portion of the first semiconductor, the second portion of the first semiconductor, the second charge storage film, the fourth insulator, the second insulator, and the second layer stack are arranged in this order in a second direction in a stack surface of the first layer stack and the second layer stack, and
   the first insulator, the third insulator, the first charge storage film, the first portion of the first semiconductor, the second portion of the first semiconductor, the second charge storage film, the fourth insulator, and the second insulator extend in a third direction intersecting the second direction in the stack surface.

2. The memory device according to claim 1, further comprising
   a third conductor stacked above the first conductor in the first direction;
   a fourth conductor stacked above the second conductor in the first direction, and separated from the third conductor in same layer;
   a third charge storage film between the third conductor and the first portion of the first semiconductor;
   a fourth charge storage film between the fourth conductor and the second portion of the first semiconductor;
   a fifth insulator between the third conductor and the third charge storage film;
   a sixth insulator between the fourth conductor and the fourth charge storage film;
   a seventh insulator between the fifth insulator and the third charge storage film; and
   an eighth insulator between the sixth insulator and the fourth charge storage film,
   wherein
   the seventh insulator and the eighth insulator have a dielectric constant higher than that of the fifth insulator and the sixth insulator.

3. The memory device according to claim 2, wherein
   the third insulator and the seventh insulator are separated from each other; and
   the fourth insulator and the eighth insulator are separated from each other.

4. The memory device according to claim 1, further comprising a second semiconductor on a top surface of the first portion of the first semiconductor and on a top surface of the second portion of the first semiconductor above the first conductor and the second conductor.

5. The memory device according to claim 1, wherein the first charge storage film and the second charge storage film include polysilicon or metal.

6. The memory device according to claim 5, wherein the third insulator and the fourth insulator include hafnium (Hf) or zirconium (Zr).

7. The memory device according to claim 1, further comprising:
   a first sacrificial member arranged alongside the third insulator between the first insulator and the first charge storage film; and
   a second sacrificial member arranged alongside the fourth insulator between the second insulator and the second charge storage film;
   wherein
   the first sacrificial member includes a first oxide film being in contact with the first charge storage film, and a first nitride film being in contact with the first insulator; and
   the second sacrificial member includes a second oxide film being in contact with the second charge storage film, and a second nitride film being in contact with the second insulator.

8. The memory device according to claim 7, further comprising:
   a ninth insulator separating, into two portions, each of the first semiconductor, the first charge storage film, the second charge storage film, the first insulator, the second insulator, the third insulator, and the fourth insulator; and
   a tenth insulator separating, into two portions, each of the first semiconductor, the first charge storage film, the second charge storage film, the first insulator, the second insulator, the first sacrificial member, and the second sacrificial members.

9. The memory device according to claim 7, wherein the first oxide film and the second oxide film include boron (B) or phosphorus (P).

10. The memory device according to claim 1, wherein the first semiconductor, the first charge storage film, and the second charge storage film are shorter in the third direction than the third insulator and the fourth insulator.

11. The memory device according to claim 10, wherein the first semiconductor is shorter in the third direction than the first charge storage film and the second charge storage film.

12. The memory device according to claim 11, wherein the first charge storage film and the second charge storage film include boron (B) or carbon (C).

13. The memory device according to claim 1, further comprising two ninth insulators each extending in the third direction, and separating, into two portions, each of the first semiconductor, the first charge storage film, the second charge storage film, the first insulator, the second insulator, the third insulator, and the fourth insulator, wherein
 a portion of the first conductor sandwiched between the two ninth insulators has a length in the third direction shorter than that of the first charge storage film and the second charge storage film in the third direction.

14. The memory device according to claim 1, wherein each of the first semiconductor, the first charge storage film, and the second charge storage film are gradually thinned toward an end in the third direction.

* * * * *